(12) United States Patent
Parham et al.

(10) Patent No.: US 11,296,281 B2
(45) Date of Patent: *Apr. 5, 2022

(54) MATERIALS FOR ORGANIC ELECTROLUMINESCENT DEVICES

(71) Applicant: Merck Patent GmbH, Darmstadt (DE)

(72) Inventors: Amir Parham, Frankfurt am Main (DE); Thomas Eberle, Landau (DE); Anja Jatsch, Frankfurt am Main (DE); Tobias Grossmann, Darmstadt (DE); Jonas Valentin Kroeber, Frankfurt am Main (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/492,820

(22) PCT Filed: Mar. 12, 2018

(86) PCT No.: PCT/EP2018/055998
§ 371 (c)(1),
(2) Date: Sep. 10, 2019

(87) PCT Pub. No.: WO2018/166934
PCT Pub. Date: Sep. 20, 2018

(65) Prior Publication Data
US 2020/0152883 A1     May 14, 2020

(30) Foreign Application Priority Data
Mar. 15, 2017   (EP) .................................. 17160998

(51) Int. Cl.
| C07D 405/10 | (2006.01) |
| H01L 51/00 | (2006.01) |
| C07D 409/10 | (2006.01) |
| H01L 51/50 | (2006.01) |

(52) U.S. Cl.
CPC ........ *H01L 51/0061* (2013.01); *C07D 405/10* (2013.01); *C07D 409/10* (2013.01); *H01L 51/006* (2013.01); *H01L 51/0067* (2013.01); *H01L 51/0073* (2013.01); *H01L 51/0074* (2013.01); *H01L 51/5016* (2013.01); *H01L 51/5056* (2013.01); *H01L 51/5072* (2013.01); *H01L 51/5096* (2013.01)

(58) Field of Classification Search
CPC .......................... C07D 313/00; H01L 51/0061
USPC .................................................. 549/269, 46
See application file for complete search history.

(56) References Cited

U.S. PATENT DOCUMENTS

| 9,133,119 B2 | 9/2015 | Parham et al. |
| 9,209,406 B2 | 12/2015 | Mizutani et al. |
| 9,620,722 B2* | 4/2017 | Martynova .......... C07D 495/04 |
| 10,135,002 B2 | 11/2018 | Ono et al. |
| 10,529,930 B2* | 1/2020 | Parham ................... C07F 5/025 |
| 10,600,970 B2* | 3/2020 | Parham ............... H01L 51/0074 |
| 10,622,565 B2* | 4/2020 | Parham ............... H01L 51/0067 |
| 2014/0158992 A1 | 6/2014 | Xia et al. |
| 2016/0141508 A1 | 5/2016 | Jatsch et al. |
| 2016/0181548 A1 | 6/2016 | Parham et al. |
| 2017/0207399 A1 | 7/2017 | Parham et al. |
| 2018/0226585 A1* | 8/2018 | Park .................... H01L 51/0074 |

FOREIGN PATENT DOCUMENTS

| CN | 106459018 A | | 2/2017 | |
| JP | 2009021336 A | | 1/2009 | |
| KR | 2016208862 | * | 12/2016 | ............ H01L 51/50 |
| TW | 201022401 A | | 6/2010 | |
| TW | 201619152 A | | 6/2016 | |
| WO | WO-2011088877 A1 | | 7/2011 | |
| WO | WO-2012143080 A2 | | 10/2012 | |
| WO | WO-2013077352 A1 | | 5/2013 | |
| WO | WO-2013088973 A1 | | 6/2013 | |
| WO | WO-2014157618 A1 | | 10/2014 | |
| WO | WO-2015000549 A1 | | 1/2015 | |
| WO | WO-2015014434 A1 | | 2/2015 | |
| WO | 2015169412 | * | 11/2015 | ............ H01L 51/50 |
| WO | 2016015810 | * | 2/2016 | ............ H01L 51/50 |
| WO | WO-2016015810 A1 | | 2/2016 | |
| WO | 2016198144 | * | 12/2016 | ............ H01L 51/50 |
| WO | 2017016667 | * | 2/2017 | ............ H01L 51/50 |

OTHER PUBLICATIONS

Chen, Dyes and Pigments, vol. 175, Apr. 2020, 108143.*
Dorwald F. A. Side Reactions in Organic Synthesis, 2005, Wiley: VCH, Weinheim p. IX of Preface p. 1-15.*
International Search Report for PCT/EP2018/055998 dated May 24, 2018.
Written Opinion of the International Searching Authority for PCT/EP2018/055998 dated May 24, 2018.

\* cited by examiner

*Primary Examiner* — Nizal S Chandrakumar
(74) *Attorney, Agent, or Firm* — Faegre Drinker Biddle & Reath LLP

(57) ABSTRACT

The present invention relates to dibenzofuran and dibenzothiophene derivatives, especially for use as triplet matrix materials in organic electroluminescent devices. The invention further relates to a process for preparing the compounds of the invention and to electronic devices comprising these.

8 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2018/055998, filed Mar. 12, 2018, which claims benefit of European Application No. 17160998.5, filed Mar. 15, 2017, both of which are incorporated herein by reference in their entirety.

The present invention relates to dibenzofuran and dibenzothiophene derivatives, especially for use as triplet matrix materials in organic electroluminescent devices. The invention further relates to a process for preparing the compounds of the invention and to electronic devices comprising these compounds.

Emitting materials used in organic electroluminescent devices (OLEDs) are frequently organometallic complexes which exhibit phosphorescence rather than fluorescence. For quantum-mechanical reasons, up to four times the energy efficiency and power efficiency is possible using organometallic compounds as phosphorescent emitters. In general terms, there is still a need for improvement in OLEDs, especially also in OLEDs which exhibit triplet emission (phosphorescence), for example with regard to efficiency, operating voltage and lifetime.

The properties of phosphorescent OLEDs are not just determined by the triplet emitters used. More particularly, the other materials used, for example matrix materials, are also of particular significance here. Improvements to these materials can thus also lead to distinct improvements in the OLED properties.

According to the prior art, a multitude of different material classes can be used as matrix materials for phosphorescent emitters, including carbazole derivatives, dibenzofuran derivatives and triazine derivatives.

In general terms, in the case of materials for use as matrix materials, there is still need for improvement, particularly in relation to the lifetime, but also in relation to the efficiency and operating voltage of the device.

It is an object of the present invention to provide compounds suitable for use in a phosphorescent or fluorescent OLED, especially as matrix material. More particularly, it is an object of the present invention to provide matrix materials which are suitable for red-, yellow- and green-phosphorescing OLEDs and possibly also for blue-phosphorescing OLEDs, and which lead to long lifetime, good efficiency and low operating voltage.

It has been found that, surprisingly, electroluminescent devices containing compounds of the formula (1) below have improvements over the prior art, especially when used as matrix material for phosphorescent dopants.

The present invention therefore provides a compound of the following formula (1):

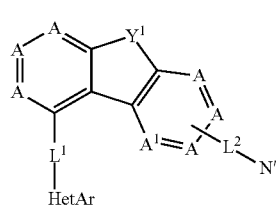

Formula (1)

where the symbols used are as follows:

A, $A^1$ is the same or different at each instance and is $CR^1$ or N, where, of all A and $A^1$, not more than two A and/or $A^1$ groups per cycle are N and that A to which $L^2$ is bonded is C;

$Y^1$ is O, S, NR or $C(R)_2$, where the R radical bonded to N is not H or D;

$L^1$ is a single bond or an aromatic or heteroaromatic ring system which has 5 to 30 aromatic ring atoms and may be substituted by one or more $R^3$ radicals;

$L^2$ is a single bond or an aromatic or heteroaromatic ring system which has 5 to 30 aromatic ring atoms and may be substituted by one or more $R^3$ radicals;

N' is a group of the formula (L-1)

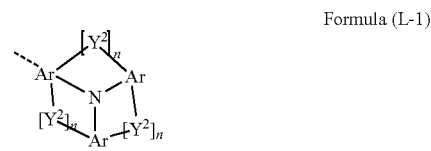

Formula (L-1)

where the dotted bond represents the linkage to $L^2$;

$Y^2$ is the same or different at each instance and is selected from a single bond, $C(R)_2$, C=O, O, S, S=O, $SO_2$, $Si(R)_2$, NR, where the R radical bonded to N is not H or D;

n is the same or different at each instance and is 0 or 1, where, when at least one $Y^2$ is a single bond, at least two n are 1; n=0 here means that the corresponding $Y^2$ group is absent;

Ar is the same or different at each instance and is an aromatic or heteroaromatic ring system which has 5 to 30 aromatic ring atoms and may be substituted by one or more $R^3$ radicals;

HetAr is a group of the formula (2), (3) or (4)

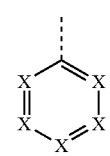

Formula(2)

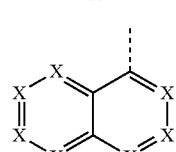

Formula (3)

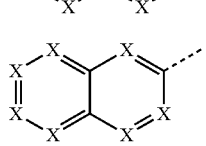

Formula (4)

where the dotted bond represents the linkage of this group;

X is the same or different at each instance and is $CR^2$ or N, with the proviso that at least one X symbol is N;

R, $R^1$, $R^2$, $R^3$ is the same or different at each instance and is selected from the group consisting of H, D, F, Cl, Br, I, CN, $NO_2$, $N(Ar^1)_2$, $N(R^4)_2$, C(=O)$Ar^1$, C(=O)$R^4$, P(=O)$(Ar^1)_2$, P$(Ar^1)_2$, B$(Ar^1)_2$, Si$(Ar^1)_3$, Si$(R^4)_3$, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to 20 carbon atoms, each of which may be substituted by one or more $R^4$ radicals, where one or more nonadjacent $CH_2$ groups may be replaced by $R^4C=CR^4$, $Si(R^4)_2$, C=O, C=NR$^4$, P(=O)(R$^4$), SO, $SO_2$, NR$^4$, O, S or CONR$^4$ and where one or more hydrogen atoms may be replaced by D, F, Cl, Br, I, CN or $NO_2$, an aromatic or heteroaromatic ring system which has 5 to 40 aromatic ring atoms and may be substituted in each case by one or more $R^4$ radicals, an aryloxy or heteroaryloxy group which has 5 to 40 aromatic ring atoms and may be substituted by one or more $R^4$ radicals, and an aralkyl or heteroaralkyl group which has 5 to 40 aromatic ring atoms and may be substituted by one or more $R^4$ radicals; at the same time, it is optionally possible for two adjacent R substituents, or two adjacent $R^1$ substituents, or two adjacent $R^2$ substituents, or two adjacent $R^3$ substituents to form an aliphatic, heteroaliphatic, aromatic or heteroaromatic ring system which may be substituted by one or more $R^4$ radicals;

$Ar^1$ is the same or different at each instance and is an aromatic or heteroaromatic ring system which has 5 to 30 aromatic ring atoms and may be substituted by one or more nonaromatic $R^4$ radicals; at the same time, two $Ar^1$ radicals bonded to the same nitrogen atom, phosphorus atom or boron atom may also be bridged to one another by a single bond or a bridge selected from N(R$^4$), C(R$^4$)$_2$, O and S;

$R^4$ is the same or different at each instance and is selected from the group consisting of H, D, F, Cl, Br, I, CN, $NO_2$, N(R$^5$)$_2$, C(=O)R$^5$, Si(R$^5$)$_3$, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to 20 carbon atoms, each of which may be substituted by one or more $R^5$ radicals, where one or more nonadjacent $CH_2$ groups may be replaced by $R^5C=CR^5$, Si(R$^5$)$_2$, C=O, C=NR$^5$, P(=O)(R$^5$), SO, $SO_2$, NR$^5$, O, S or CONR$^5$ and where one or more hydrogen atoms may be replaced by D, F, Cl, Br, I, CN or $NO_2$, an aromatic or heteroaromatic ring system which has 5 to 40 aromatic ring atoms and may be substituted in each case by one or more $R^5$ radicals, an aryloxy or heteroaryloxy group which has 5 to 40 aromatic ring atoms and may be substituted by one or more $R^5$ radicals, and an aralkyl or heteroaralkyl group which has 5 to 40 aromatic ring atoms and may be substituted by one or more $R^5$ radicals; at the same time, it is optionally possible for two adjacent $R^4$ substituents to form an aliphatic or aromatic or heteroaromatic ring system which may be substituted by one or more $R^5$ radicals;

$R^5$ is the same or different at each instance and is selected from the group consisting of H, D, F, CN, an aliphatic hydrocarbyl radical having 1 to 20 carbon atoms, and an aromatic or heteroaromatic ring system having 5 to 30 aromatic ring atoms in which one or more hydrogen atoms may be replaced by D, F, Cl, Br, I or CN and which may be substituted by one or more alkyl groups each having 1 to 4 carbon atoms; at the same time, it is possible for two or more adjacent $R^5$ substituents together to form an aliphatic ring system;

where the following compounds are excluded from the invention:

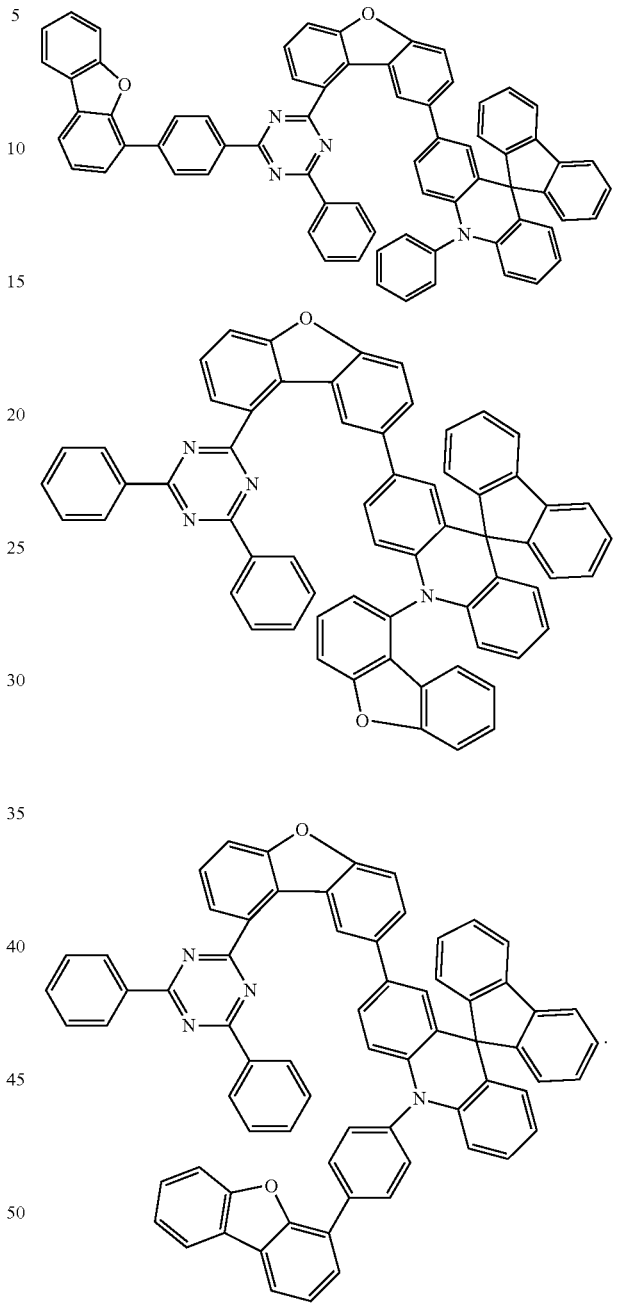

In the compounds of formula (1), $L^2$ is always bonded to an A group, not to an $A^1$ group.

Adjacent substituents in the context of the present invention are substituents bonded to carbon atoms that are in turn bonded directly to one another, or bonded to the same carbon atom.

The wording that two or more radicals together may form a ring, in the context of the present application, shall be understood to mean, inter alia, that the two radicals are joined to one another by a chemical bond. This is illustrated by the following scheme:

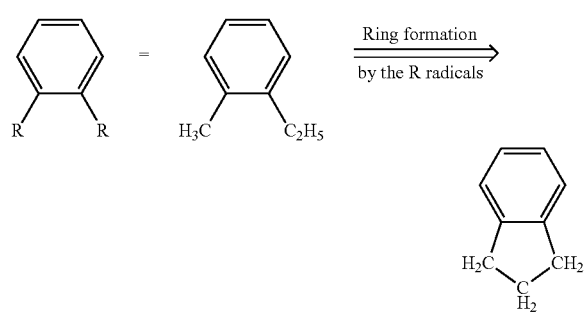

In addition, the abovementioned wording shall also be understood to mean that, if one of the two radicals is hydrogen, the second radical binds to the position to which the hydrogen atom was bonded, forming a ring.

A fused aryl group in the context of the present invention is a group in which two or more aromatic groups are fused, i.e. annellated, to one another along a common edge, as, for example, in naphthalene. By contrast, for example, fluorene is not a fused aryl group in the context of the present invention, since the two aromatic groups in fluorene do not have a common edge.

An aromatic ring system in the context of this invention contains 6 to 40 carbon atoms in the ring system. An aromatic ring system in the context of this invention is understood to mean a system which does not necessarily contain only aryl or heteroaryl groups, but in which it is also possible for two or more aryl or heteroaryl groups to be joined by a nonaromatic unit (preferably less than 10% of the atoms other than H), for example a carbon, nitrogen or oxygen atom. For example, systems such as fluorene, 9,9'-spirobifluorene, 9,9-diarylfluorene, triarylamine, etc. shall also be regarded as aromatic ring systems in the context of this invention, and likewise systems in which two or more aryl groups are joined, for example, by a short alkyl group. In addition, aromatic rings joined to one another by a single bond, i.e. oligoarylenes or oligoheteroarylenes, for example biphenyl, terphenyl or quaterphenyl, are referred to as aromatic ring systems in the context of this application.

In the context of the present invention, an aliphatic hydrocarbyl radical or an alkyl group or an alkenyl or alkynyl group which may contain 1 to 40 carbon atoms and in which individual hydrogen atoms or $CH_2$ groups may also be substituted by the abovementioned groups are preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy or 2,2,2-trifluoroethoxy. A thioalkyl group having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups according to the present invention may be straight-chain, branched or cyclic, where one or more nonadjacent $CH_2$ groups may be replaced by the abovementioned groups; in addition, it is also possible for one or more hydrogen atoms to be replaced by D, F, Cl, Br, I, CN or $NO_2$, preferably F, Cl or CN, further preferably F or CN, especially preferably CN.

An aromatic or heteroaromatic ring system having 5-40 aromatic ring atoms is especially understood to mean groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, quinoxaline, quinazoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or groups derived from a combination of these systems.

In a preferred embodiment of the invention, not more than one A or $A^1$ group per cycle is N, and the other A or $A^1$ groups are $CR^1$. More preferably, A and $A^1$ are $CR^1$, and so the compound of the formula (1) is a compound of the following formula (1a):

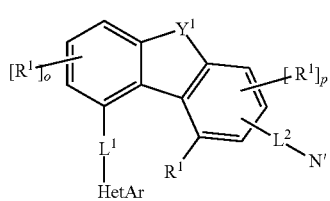

Formula (1a)

where the symbols used have the definitions given above, o is 0, 1, 2 or 3 and p is 0, 1 or 2.

In a preferred embodiment of the invention, the indices p and o in formula (1a) are the same or different and are 0, 1 or 2, more preferably 0 or 1 and most preferably 0.

Preferred embodiments of the formula (L-1) are the structures of the formulae (L-2) to (L-7)

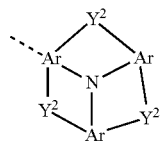

Formula (L-2)

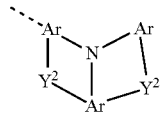

Formula (L-3)

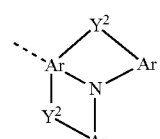

Formula (L-4)

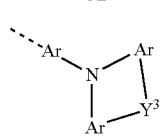

Formula (L-5)

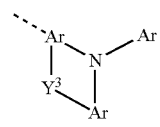

Formula (L-6)

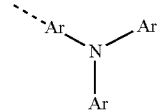

Formula (L-7)

where the symbols that occur have the definitions given above and in addition:
$Y^3$ is the same or different at each instance and is selected from $C(R)_2$, C=O, O, S, S=O, $SO_2$, $Si(R)_2$ and NR, where the R radical bonded to N is not H or D.

In formula (L-2), preferably not all three $Y^2$ groups are a single bond.

In a further embodiment of the invention, $Y^3$ in formula (L-5) is not $C(Ph)_2$ where the two phenyl groups are bonded to one another via a single bond.

In a further embodiment of the invention, $Y^3$ is the same or different at each instance and is selected from C=O, O, S, S=O, $SO_2$, $Si(R)_2$, NR, where the R radical bonded to N is not H or D.

In a further embodiment, $Y^3$ is selected from C=O, O, S, S=O, $SO_2$, $Si(R)_2$ and NR, where the R radical bonded to N is not H or D, and $Y^2$ is the same or different at each instance and is selected from a single bond, C=O, O, S, S=O, $SO_2$, $Si(R)_2$ and NR, where the R radical bonded to N is not H or D.

In a further embodiment, $Y^3$ is selected from O and S, and $Y^2$ is the same or different at each instance and is selected from a single bond, O, S and $SiR_2$.

In a preferred embodiment of the invention, N' is a group of the formula (L-7).

Preferred embodiments of the formula (1a) are the compounds of the formulae (1b) to (1d):

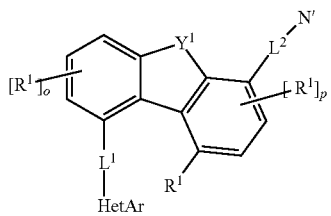

Formula (1b)

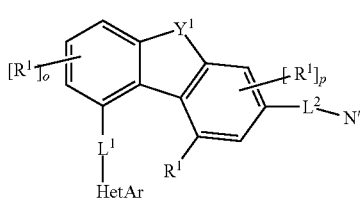

Formula (1c)

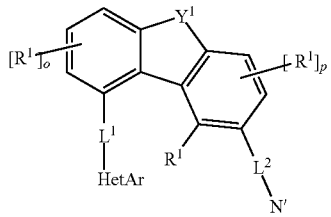

Formula (1d)

where the symbols and indices that occur have the definitions above.

A particularly preferred embodiment is the compound of the formula (1d). Preferred embodiments of the HetAr group are described hereinafter.

Preferred embodiments of the groups of the formulae (2), (3) and (4) are the groups of the following formulae (2-1) to (2-10), (3-1) and (4-1):

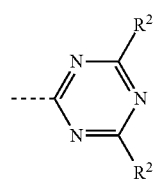

Formula (2-1)

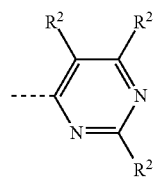

Formula (2-2)

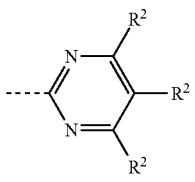

Formula (2-3)

Formula (2-4)
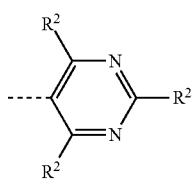

Formula (2-5)
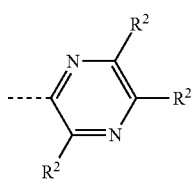

Formula (2-6)
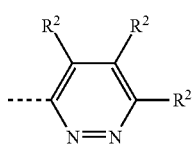

Formula (2-7)
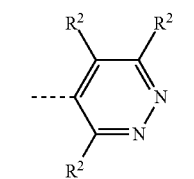

Formula (2-8)
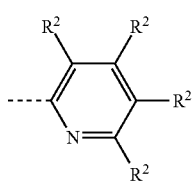

Formula (2-9)
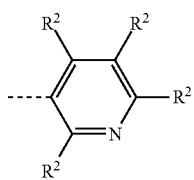

Formula (2-10)
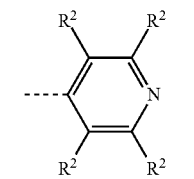

Formula (3-1)
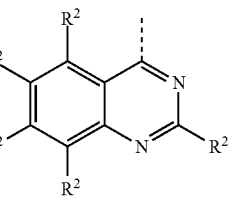

Formula (4-1)
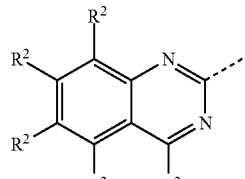

where the dotted bond represents the linkage of these groups and $R^2$ has the definitions given above.

Preference is given to the groups of the formulae (2-1) to (2-3), (3-1) and (4-1), and particular preference to the group of the formula (2-1).

Preferred embodiments of the abovementioned groups are the groups of the following formulae (2-1a) to (4-1a):

Formula (2-1a)
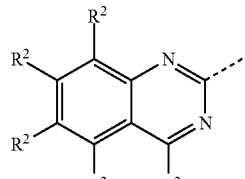

Formula (2-2a)
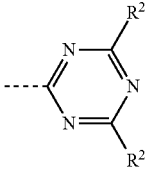

Formula (2-3a)
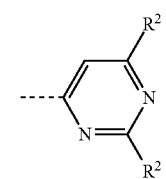

Formula (2-4a)
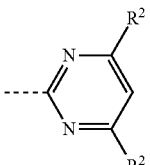

Formula (2-5a)
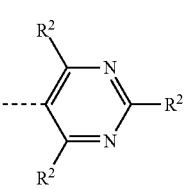

Formula (2-6a)
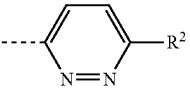

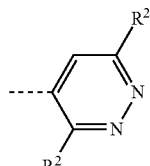 Formula (2-7a)

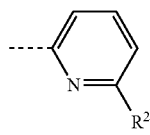 Formula (2-8a)

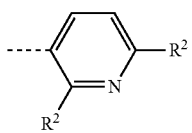 Formula (2-9a)

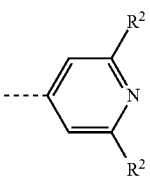 Formula (2-10a)

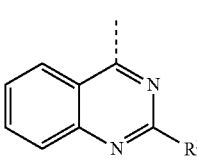 Formula (3-1a)

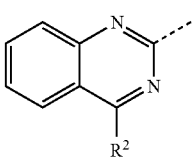 Formula (4-1a)

where the dotted bond represents the linkage of these groups and $R^2$ represents a substituent according to the abovementioned definition other than hydrogen.

The $R^2$ substituent on the HetAr group is preferably the same or different at each instance and is H or an aromatic or heteroaromatic ring system which has 6 to 24 aromatic ring atoms and may be substituted in each case by one or more $R^4$ radicals. At the same time, $R^2$ in the groups of the formulae (2-1a) to (4-1a) is not hydrogen. The aromatic or heteroaromatic ring system preferably has 6 to 18 aromatic ring atoms. It is more preferably an aromatic ring system having 6 to 12 aromatic ring atoms or a heteroaromatic ring system having 6 to 13 aromatic ring atoms, each of which may be substituted by one or more $R^4$ radicals, but is preferably unsubstituted. Examples of suitable $R^2$ groups are selected from the group consisting of phenyl, biphenyl, especially ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^4$ radicals, but are preferably unsubstituted.

Examples of suitable $R^2$ groups are the structures $R^2$-1 to $R^2$-29 listed below:

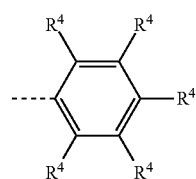 $R^2$-1

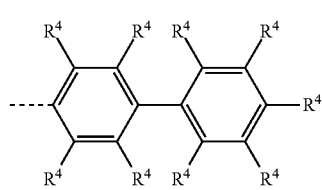 $R^2$-2

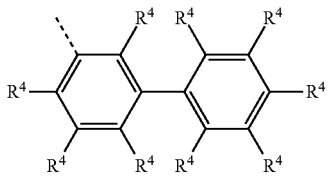 $R^2$-3

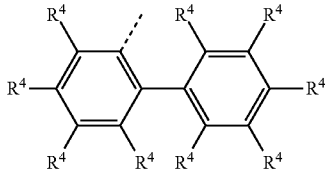 $R^2$-4

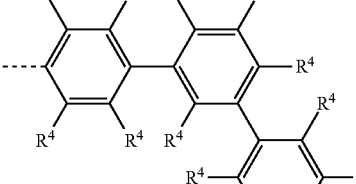 $R^2$-5

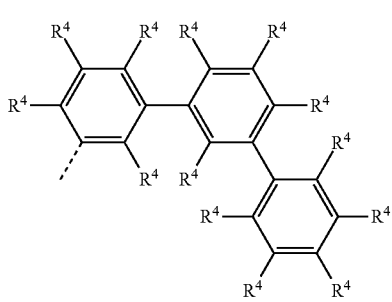 $R^2$-6

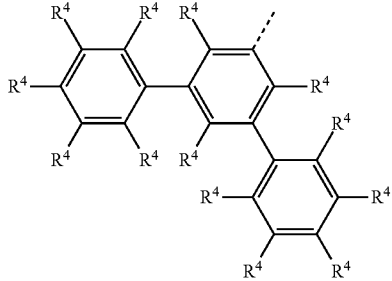 $R^2$-7

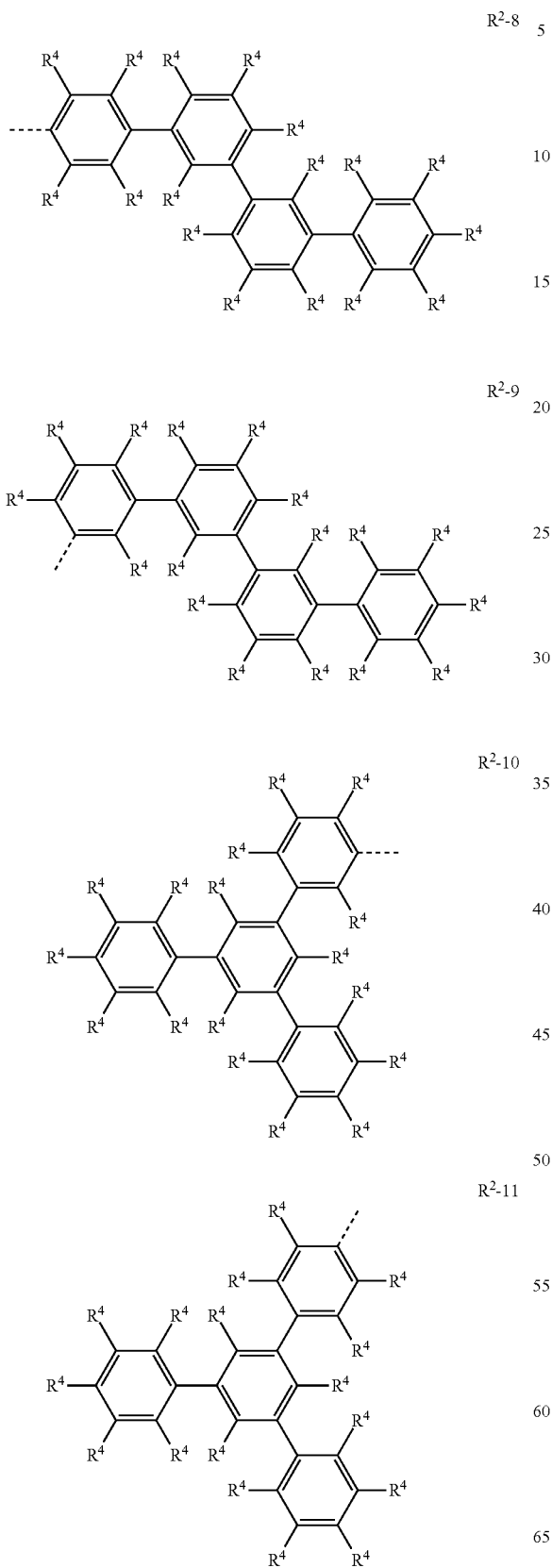
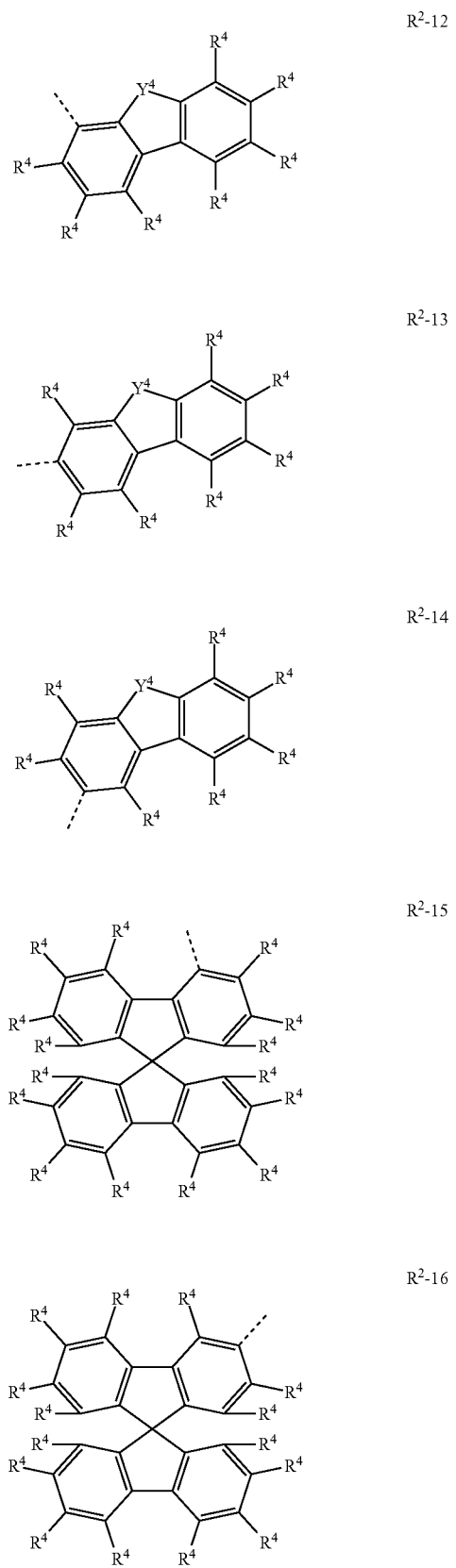

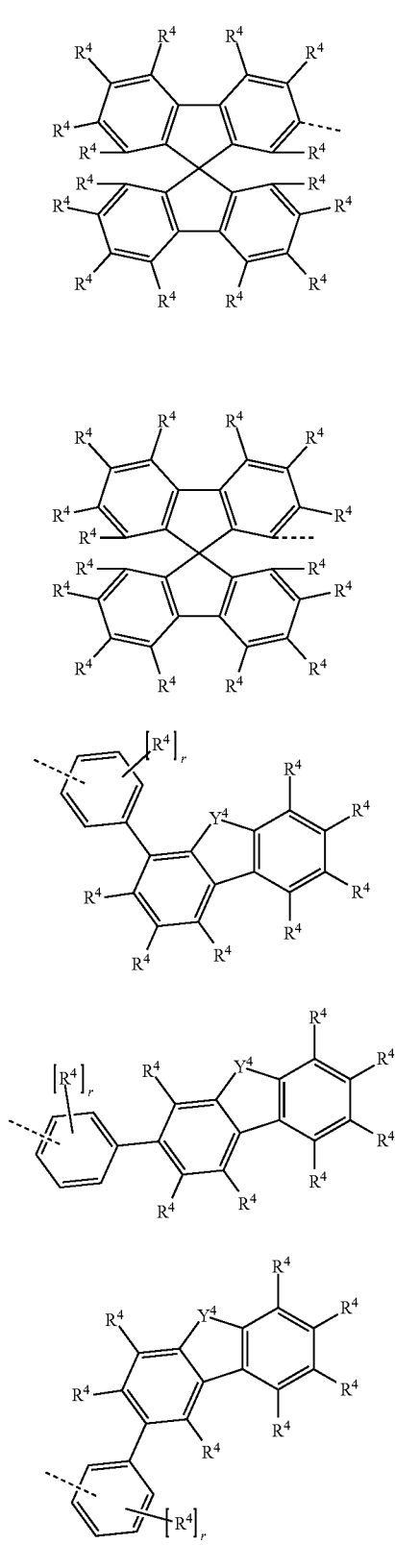

-continued

R²-28

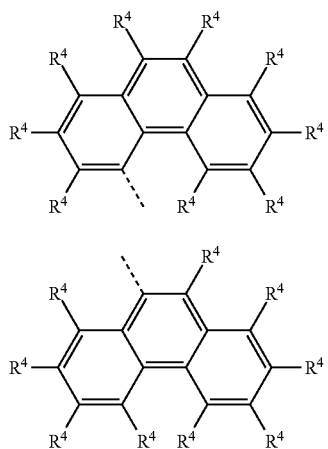

R²-29 where R⁴ has the definitions given above and the dotted bond represents the bond to the heteroaryl group and r is 0, 1, 2, 3 or 4 and in addition:

Y⁴ is the same or different at each instance and is selected from $C(R^4)_2$, $C=O$, O, S, $S=O$, $SO_2$, $Si(R^4)_2$, $NR^4$, where the R⁴ radical bonded to N is not H or D.

Preferred embodiments of the N' group are stated hereinafter. As described above, the N' group is a group of the formula (L-1) or preferably of the formula (L-2) to (L-7).

In a preferred embodiment of the invention, the Ar group in the group of the formula (L-1) or the preferred embodiments is the same or different at each instance and is an aromatic or heteroaromatic ring system having 6 to 24 aromatic ring atoms, preferably having 6 to 18 aromatic ring atoms, more preferably an aromatic ring system having 6 to 12 aromatic ring atoms or a heteroaromatic ring system having 6 to 13 aromatic ring atoms, each of which may be substituted by one or more R³ radicals, but is preferably unsubstituted. Examples of suitable Ar groups are selected from the group consisting of phenyl, biphenyl, especially ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more R³ radicals, but are preferably unsubstituted.

Particularly preferred Ar groups are the groups of the following formulae (Ar-1) to (Ar-29):

Ar-1

Ar-2

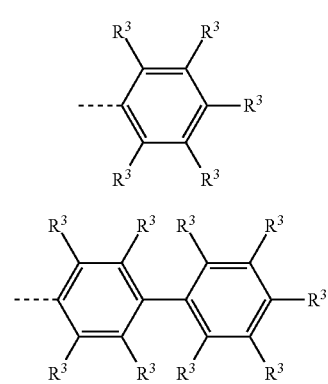

Ar-3

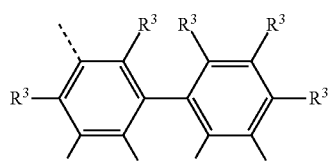

Ar-4

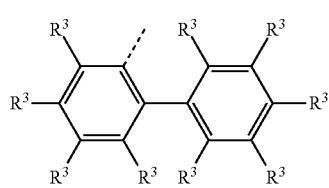

Ar-5

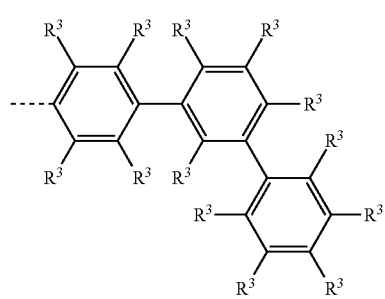

Ar-6

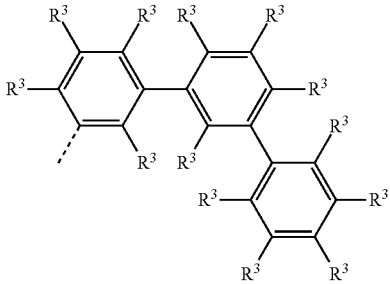

Ar-7

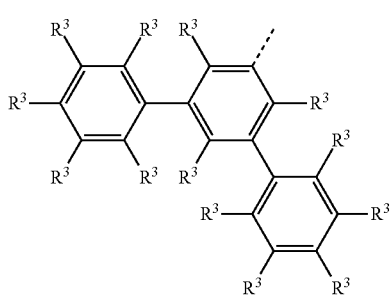

Ar-8

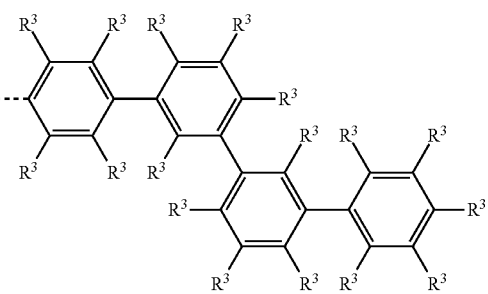

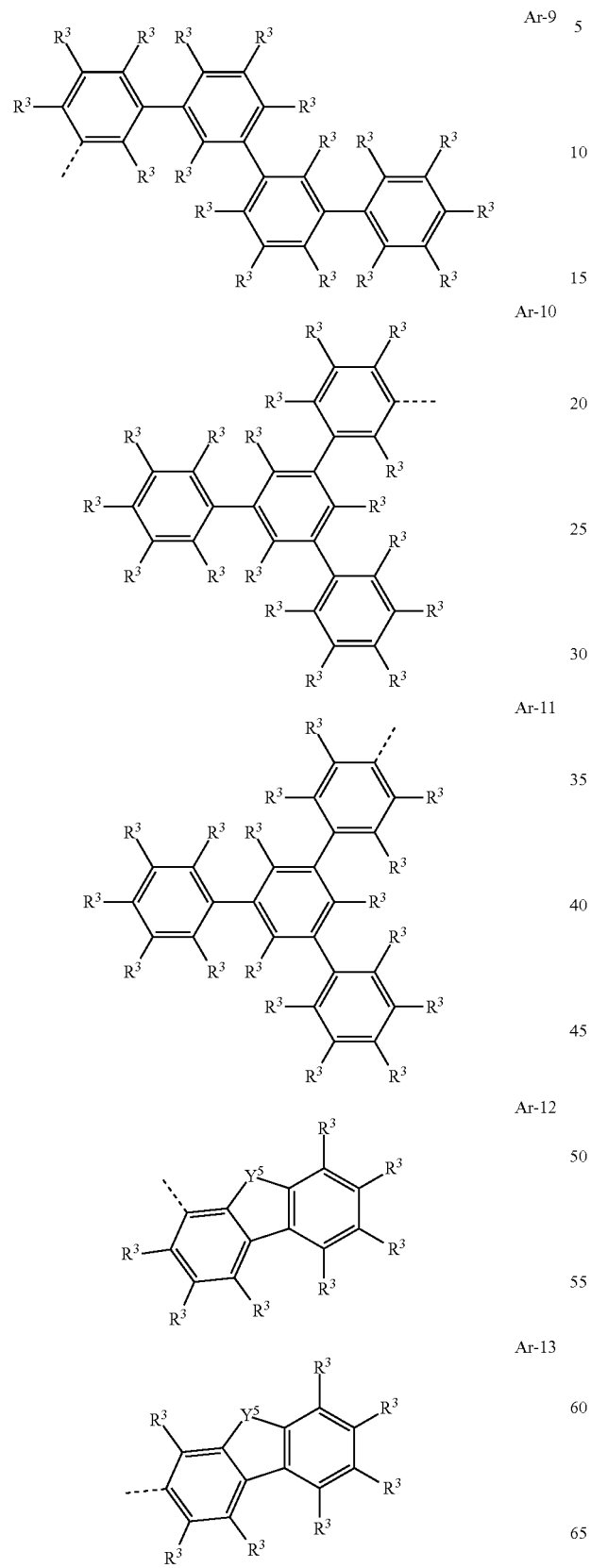
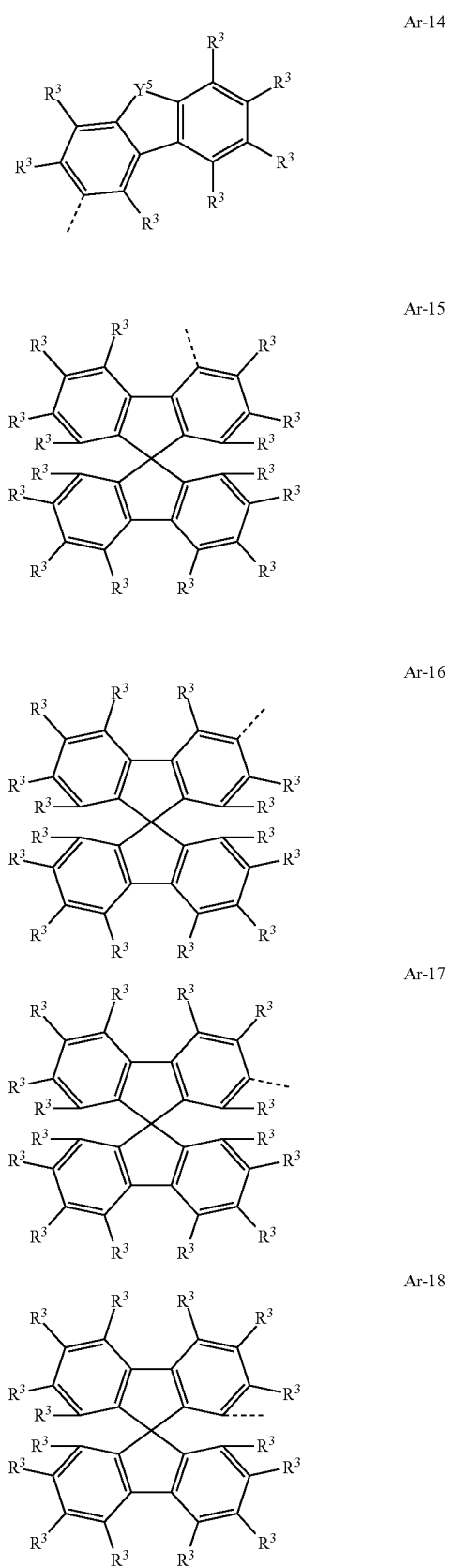

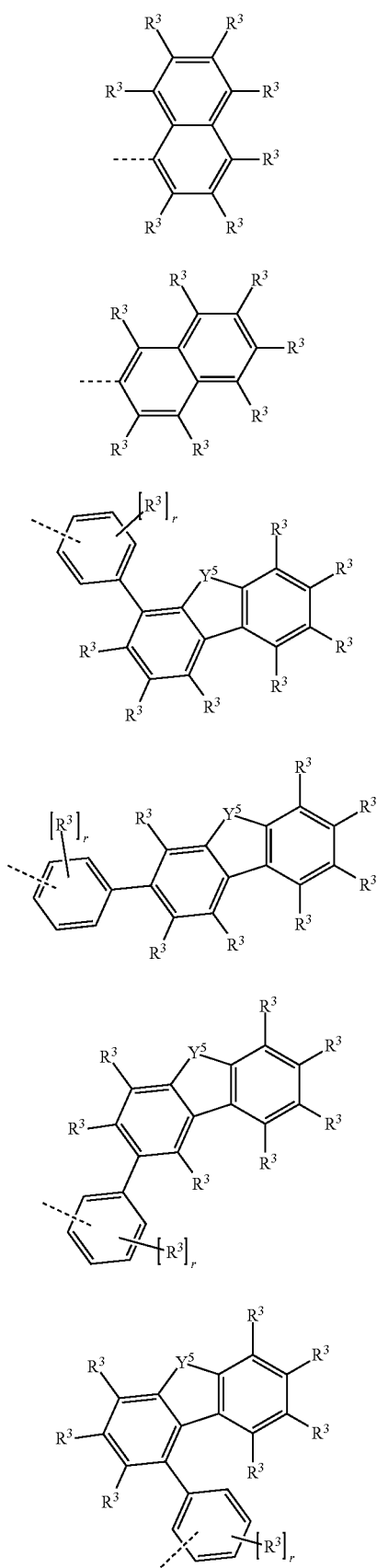

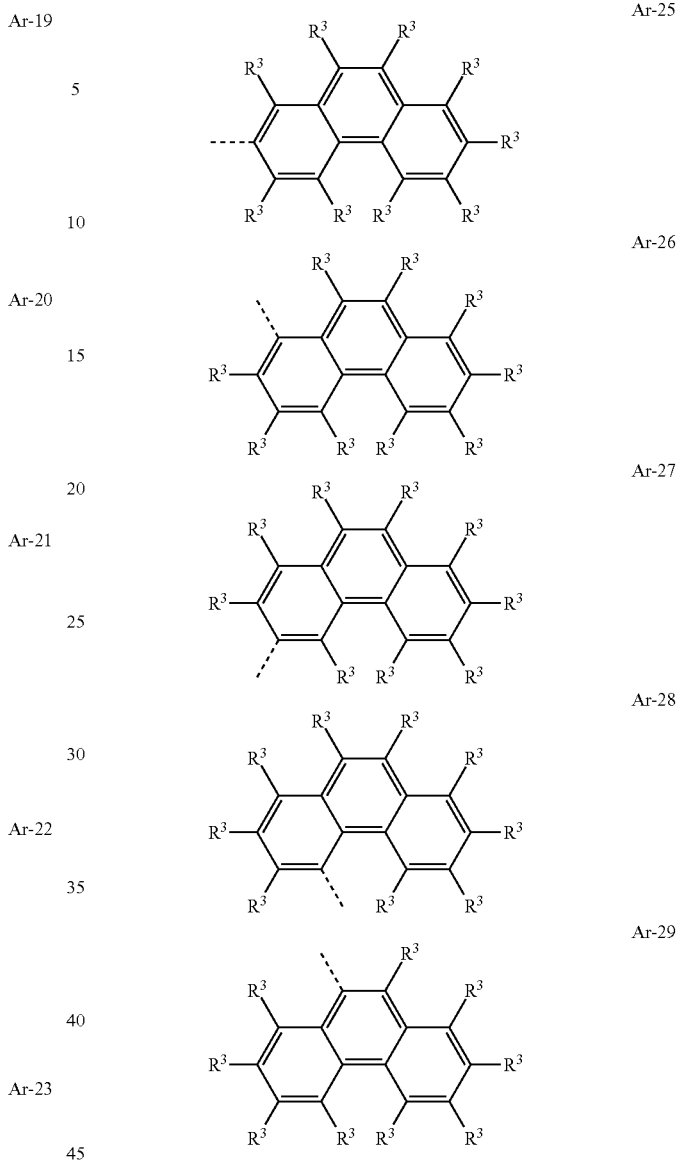

where R³ and r have the definitions given above and the dotted bond represents the bond to the nitrogen and, if required, there may be a bond to L², Y² or Y³ in place of R³, and in addition:

Y⁵ is the same or different at each instance and is selected from $C(R^3)_2$, C=O, O, S, S=O, $SO_2$, $Si(R^3)_2$, $NR^3$, where the R³ radical bonded to N is not H or D.

In a preferred embodiment of the invention, R³ which is not bonded to a nitrogen atom is the same or different at each instance and is H, an alkyl group having 1 to 4 carbon atoms or an aromatic or heteroaromatic ring system having 5 to 14 aromatic ring atoms. More preferably, R³ is the same or different at each instance and is H or an alkyl group having 1 to 4 carbon atoms.

In a further preferred embodiment of the invention, Y¹ is the same or different at each instance and is O or S, more preferably O.

In a further preferred embodiment of the invention, Y² and Y³ are the same or different at each instance and are O or S.

When Y² or Y³, Y⁴ or Y⁵ is NR, or NR³ or NR⁴, it is preferable when this R, R³ or R⁴ radical is the same or different at each instance and is an aromatic or heteroaromatic ring system which has 5 to 24 aromatic ring atoms and may be substituted in each case by one or more $R^4$ or $R^5$ radicals, more preferably an aromatic or heteroaromatic ring system which has 6 to 18 aromatic ring atoms and may be substituted by one or more $R^4$ or $R^5$ radicals. Examples of suitable R, $R^3$ or $R^4$ substituents are selected from the group consisting of phenyl, biphenyl, especially ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1,3,5-triazinyl, 4,6-diphenyl-1,3,5-triazinyl, 1-, 2-, 3- or 4-dibenzofuranyl, 1-, 2-, 3- or 4-dibenzothienyl and 1-, 2-, 3- or 4-carbazolyl, where the carbazolyl group is substituted on the nitrogen atom by an $R^4$ or $R^5$ radical other than H or D. These groups may each be substituted by one or more $R^5$ radicals, but are preferably unsubstituted. Suitable structures R, $R^3$ or $R^4$ are the same structures as depicted before for $R^2$-1 to $R^2$-29, where the $R^4$ radicals in the case of $R^4$ are $R^5$.

When $Y^2$ or $Y^3$, $Y^4$ or $Y^5$ is $C(R)_2$, or $C(R^3)_2$ or $C(R^4)_2$, it is preferable when these R, $R^3$ or $R^4$ radicals are the same or different at each instance and are a straight-chain alkyl group having 1 to 10 carbon atoms or a branched or cyclic alkyl group having 3 to 10 carbon atoms or an alkenyl group having 2 to 10 carbon atoms, each of which may be substituted by one or more $R^4$ or $R^5$ radicals, where one or more nonadjacent $CH_2$ groups may be replaced by O and where one or more hydrogen atoms may be replaced by D or F, or are an aromatic or heteroaromatic ring system which has 5 to 24 aromatic ring atoms and may optionally be substituted in each case by one or more $R^4$ or $R^5$ radicals; at the same time, the two R, $R^3$ or $R^4$ substituents may optionally form a monocyclic or polycyclic, aliphatic, aromatic or heteroaromatic ring system which may be substituted by one or more $R^4$ or $R^5$ radicals. Ring formation between the two R, $R^3$ or $R^4$ substituents forms a spiro system, for example a spirobifluorene or a derivative of a spirobifluorene, when the R, $R^3$ or $R^4$ groups are phenyl groups.

In a further preferred embodiment of the invention, $L^1$ is a single bond or an aromatic or heteroaromatic ring system which has 5 to 24 aromatic ring atoms and may be substituted by one or more $R^3$ radicals. $L^1$ is more preferably a single bond, an aromatic ring system having 6 to 12 aromatic ring atoms or a heteroaromatic ring system having 6 to 13 aromatic ring atoms, each of which may be substituted by one or more $R^3$ radicals, but is preferably unsubstituted. More preferably, $L^1$ is a single bond or an aromatic ring system having 6 to 12 aromatic ring atoms, especially a single bond. Examples of suitable aromatic or heteroaromatic ring systems $L^1$ are selected from the group consisting of phenylene, biphenyl, fluorene, pyridine, pyrimidine, triazine, dibenzofuran, dibenzothiophene and carbazole, each of which may be substituted by one or more $R^3$ radicals, but are preferably unsubstituted.

In a further preferred embodiment of the invention, $L^2$ is a single bond or an aromatic or heteroaromatic ring system which has 5 to 24 aromatic ring atoms and may be substituted by one or more $R^3$ radicals. $L^2$ is more preferably a single bond, an aromatic ring system having 6 to 12 aromatic ring atoms or a heteroaromatic ring system having 6 to 13 aromatic ring atoms, each of which may be substituted by one or more $R^3$ radicals, but is preferably unsubstituted. Most preferably, $L^2$ is a single bond or an aromatic ring system having 6 to 12 aromatic ring atoms, especially a single bond. Examples of suitable aromatic or heteroaromatic ring systems $L^2$ are selected from the group consisting of phenylene, biphenyl, fluorene, pyridine, pyrimidine, triazine, dibenzofuran, dibenzothiophene and carbazole, each of which may be substituted by one or more $R^3$ radicals, but are preferably unsubstituted, especially selected from the group consisting of phenylene, biphenyl, fluorene, pyridine, pyrimidine, triazine, dibenzofuran and dibenzothiophene.

When the compounds of the invention have R, $R^1$, $R^2$ or $R^3$ substituents, these are preferably selected from the group consisting of H, D, F, CN, $N(Ar^1)_2$, $C(=O)Ar^1$, $P(=O)(Ar^1)_2$, a straight-chain alkyl or alkoxy group having 1 to 10 carbon atoms or a branched or cyclic alkyl or alkoxy group having 3 to 10 carbon atoms or an alkenyl group having 2 to 10 carbon atoms, each of which may be substituted by one or more $R^4$ radicals, where one or more nonadjacent $CH_2$ groups may be replaced by O and where one or more hydrogen atoms may be replaced by D or F, an aromatic or heteroaromatic ring system which has 5 to 24 aromatic ring atoms and may be substituted in each case by one or more $R^4$ radicals, or an aralkyl or heteroaralkyl group which has 5 to 25 aromatic ring atoms and may be substituted by one or more $R^4$ radicals; at the same time, it is optionally possible for two R substituents, or two $R^1$ substituents, or two $R^2$ substituents, or two $R^3$ substituents, bonded to adjacent carbon atoms to form a monocyclic or polycyclic, aliphatic ring system which may be substituted by one or more $R^4$ radicals.

When the compounds of the invention have $R^4$ substituents, these are preferably selected from the group consisting of H, D, F, CN, $N(R^5)_2$, $C(=O)R^5$, a straight-chain alkyl or alkoxy group having 1 to 10 carbon atoms or a branched or cyclic alkyl or alkoxy group having 3 to 10 carbon atoms or an alkenyl group having 2 to 10 carbon atoms, each of which may be substituted by one or more $R^5$ radicals, where one or more nonadjacent $CH_2$ groups may be replaced by O and where one or more hydrogen atoms may be replaced by D or F, an aromatic or heteroaromatic ring system which has 5 to 24 aromatic ring atoms and may be substituted in each case by one or more $R^5$ radicals, or an aralkyl or heteroaralkyl group which has 5 to 25 aromatic ring atoms and may be substituted by one or more $R^5$ radicals; at the same time, it is optionally possible for two $R^4$ substituents bonded to adjacent carbon atoms to form a monocyclic or polycyclic, aliphatic ring system which may be substituted by one or more $R^5$ radicals.

Most preferably, the R, $R^1$, $R^2$ or $R^3$ substituents are selected from the group consisting of H and an aromatic or heteroaromatic ring system which has 6 to 18 aromatic ring atoms, preferably 6 to 13 aromatic ring atoms, and may be substituted in each case by one or more nonaromatic $R^4$ radicals, but is preferably unsubstituted. Examples of suitable R, $R^1$, $R^2$ or $R^3$ substituents are selected from the group consisting of phenyl, biphenyl, especially ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^4$ radicals, but are preferably unsubstituted. Suitable structures R, $R^1$, $R^2$ or $R^3$ here are the same structures as depicted above for $R^2$-1 to $R^2$-29.

In a further preferred embodiment of the invention, $R^5$ is the same or different at each instance and is selected from the group consisting of H, D, F, CN, an aliphatic hydrocarbyl radical having 1 to 10 carbon atoms, preferably having 1, 2, 3 or 4 carbon atoms, or an aromatic or heteroaromatic ring system having 5 to 30 aromatic ring atoms, preferably having 5 to 13 aromatic ring atoms, which may be substituted by one or more alkyl groups each having 1 to 4 carbon atoms, but is preferably unsubstituted.

When the compound of the invention is substituted by aromatic or heteroaromatic groups, it is preferable when these do not have any aryl or heteroaryl groups having more than two aromatic six-membered rings fused directly to one another. More preferably, the substituents do not have any aryl or heteroaryl groups having six-membered rings fused directly to one another at all. The reason for this preference is the low triplet energy of such structures. Fused aryl groups which have more than two aromatic six-membered rings fused directly to one another but are nevertheless also suitable in accordance with the invention are phenanthrene and triphenylene, since these also have a high triplet level.

The abovementioned preferences can occur individually or together. It is preferable when the abovementioned preferences occur together.

Preference is thus given to compounds of the abovementioned formula (1a) for which:

$L^1$ is a single bond or an aromatic or heteroaromatic ring system which has 5 to 30 aromatic ring atoms and may be substituted by one or more $R^3$ radicals;

$L^2$ is a single bond or an aromatic or heteroaromatic ring system which has 5 to 30 aromatic ring atoms and may be substituted by one or more $R^3$ radicals;

N' is a group of the formula (L-5), (L-6) or (L-7);

HetAr is a group of one of the above-listed formulae (2-1) to (2-10), (3-1) or (4-1);

Ar is the same or different at each instance and is an aromatic or heteroaromatic ring system which has 5 to 30 aromatic ring atoms and may be substituted by one or more $R^3$ radicals;

$Y^1$ is the same or different at each instance and is O or S;

R, $R^1$, $R^2$ or $R^3$ are the same or different at each instance and are selected from the group consisting of H, D, F, CN, $N(Ar^1)_2$, $C(=O)Ar^1$, $P(=O)(Ar^1)_2$, a straight-chain alkyl or alkoxy group having 1 to 10 carbon atoms or a branched or cyclic alkyl or alkoxy group having 3 to 10 carbon atoms or an alkenyl group having 2 to 10 carbon atoms, each of which may be substituted by one or more $R^4$ radicals, where one or more nonadjacent $CH_2$ groups may be replaced by O and where one or more hydrogen atoms may be replaced by D or F, an aromatic or heteroaromatic ring system which has 5 to 24 aromatic ring atoms and may be substituted in each case by one or more $R^4$ radicals, or an aralkyl or heteroaralkyl group which has 5 to 25 aromatic ring atoms and may be substituted by one or more $R^4$ radicals; at the same time, it is optionally possible for two R substituents, or two $R^1$ substituents, or two $R^2$ substituents, or two $R^3$ substituents, bonded to adjacent carbon atoms to form a monocyclic or polycyclic, aliphatic ring system which may be substituted by one or more $R^4$ radicals;

$R^4$ is the same or different at each instance and is selected from the group consisting of H, D, F, CN, $N(R^5)_2$, $C(=O)R^5$, a straight-chain alkyl or alkoxy group having 1 to 10 carbon atoms or a branched or cyclic alkyl or alkoxy group having 3 to 10 carbon atoms or an alkenyl group having 2 to 10 carbon atoms, each of which may be substituted by one or more $R^5$ radicals, where one or more nonadjacent $CH_2$ groups may be replaced by O and where one or more hydrogen atoms may be replaced by D or F, an aromatic or heteroaromatic ring system which has 5 to 24 aromatic ring atoms and may be substituted in each case by one or more $R^5$ radicals, or an aralkyl or heteroaralkyl group which has 5 to 25 aromatic ring atoms and may be substituted by one or more $R^5$ radicals; at the same time, it is optionally possible for two $R^4$ substituents bonded to adjacent carbon atoms to form a monocyclic or polycyclic, aliphatic ring system which may be substituted by one or more $R^5$ radicals;

the further symbols used have the definitions given above.

Examples of suitable compounds of the invention are the structures shown below.

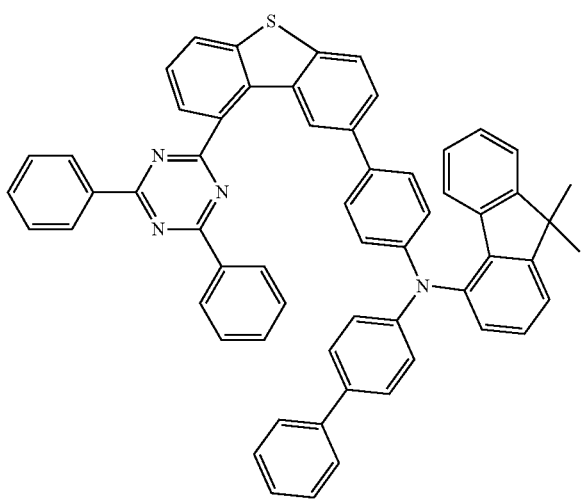
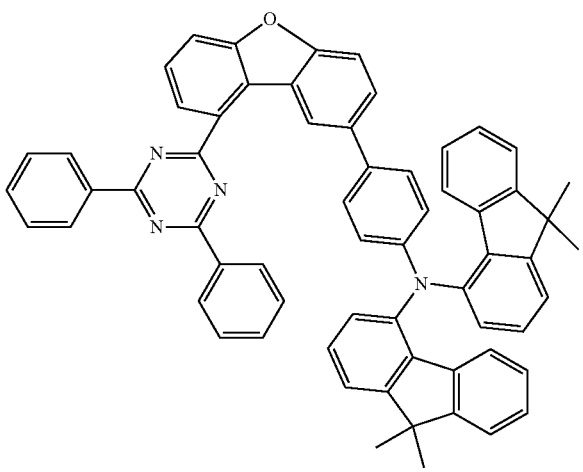

27 28
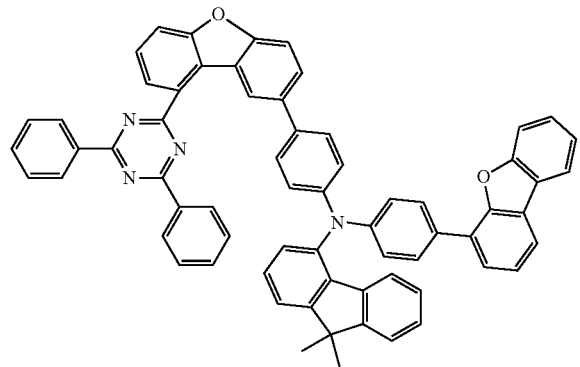
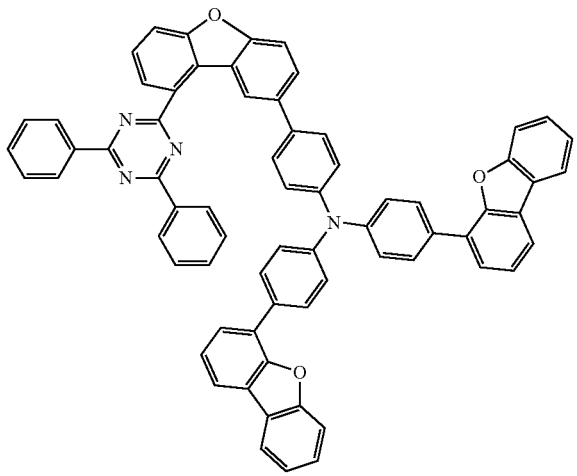
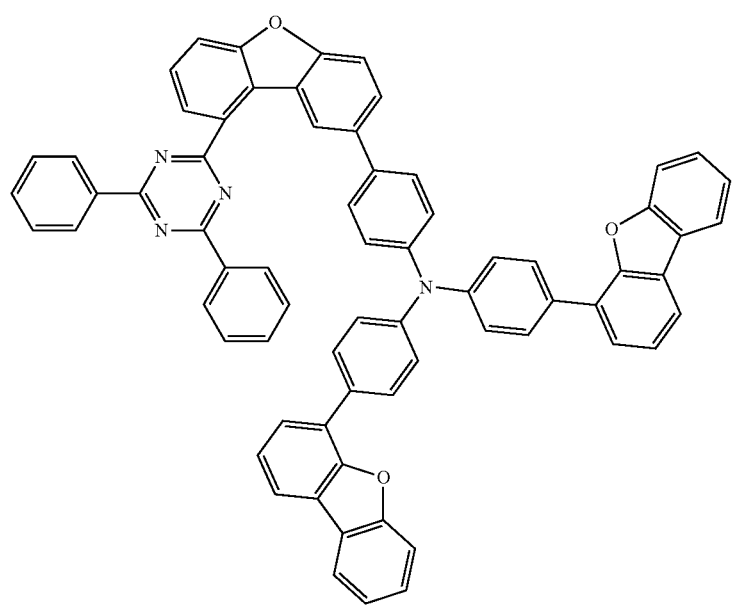
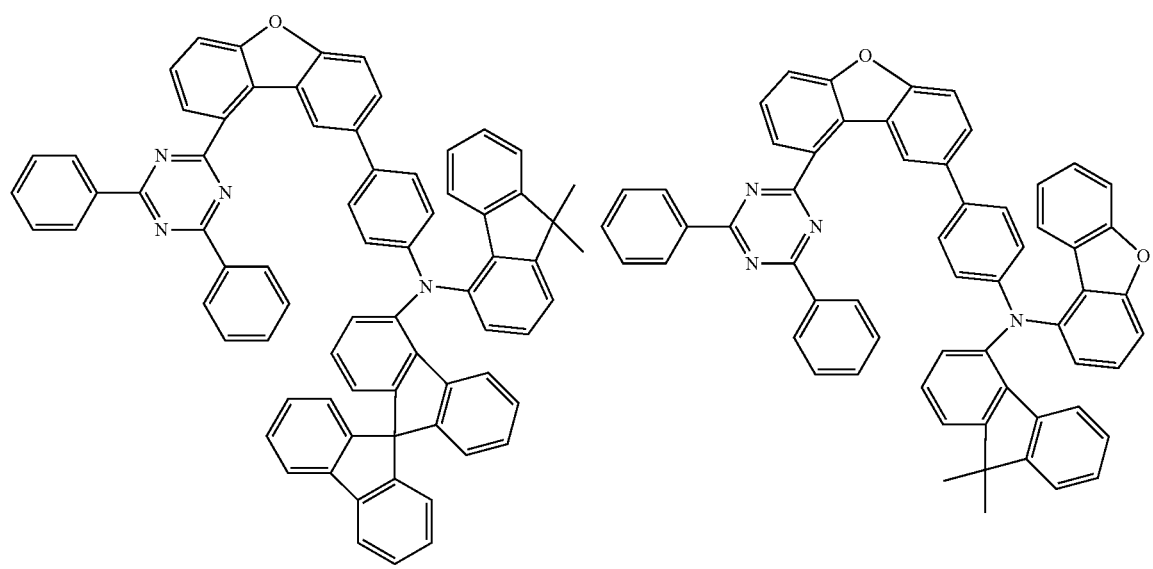

-continued
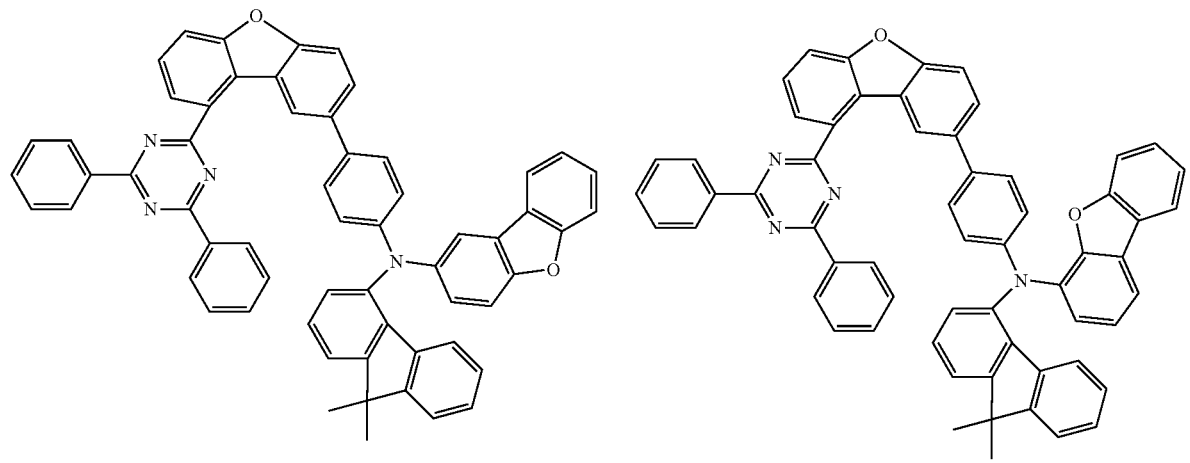
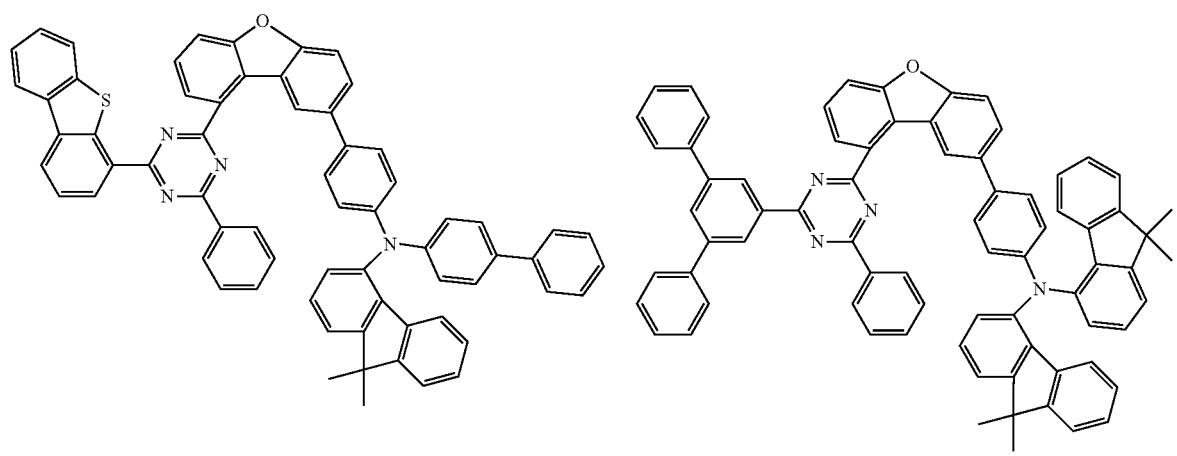
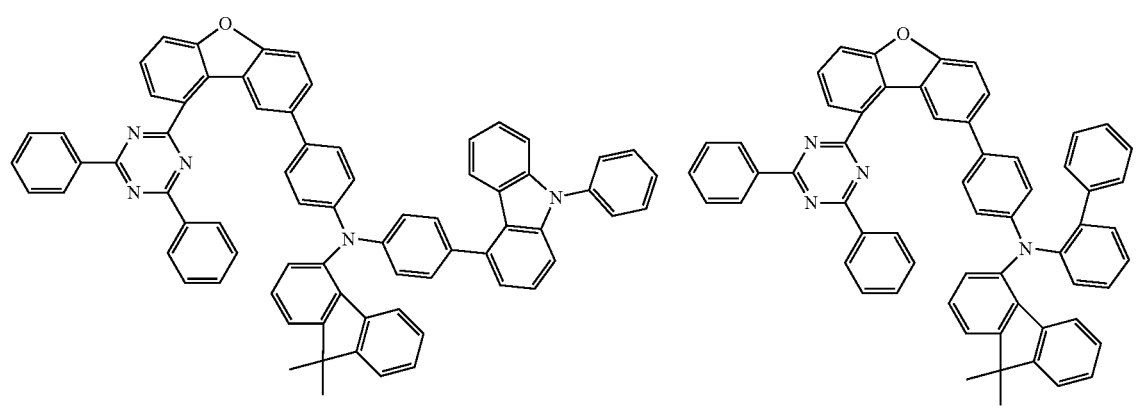

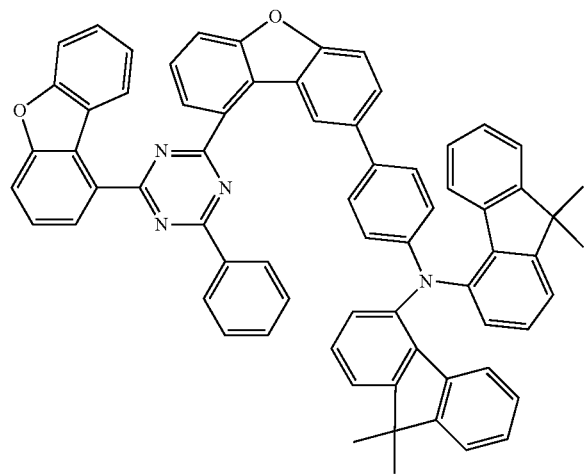
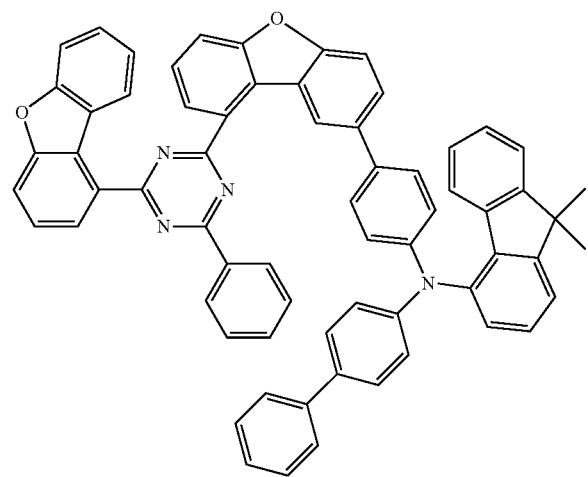
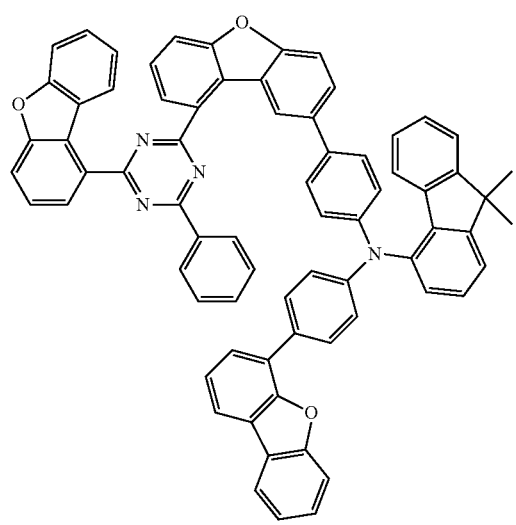
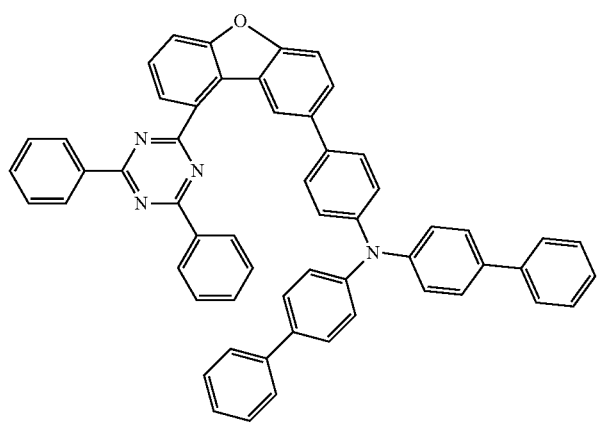
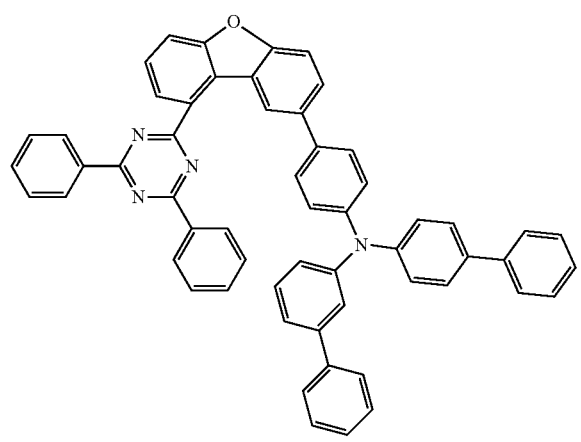
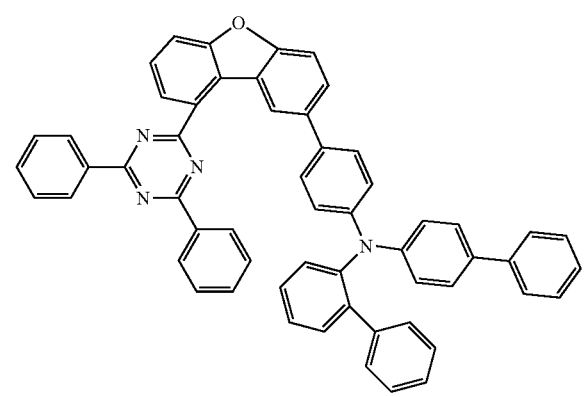

-continued
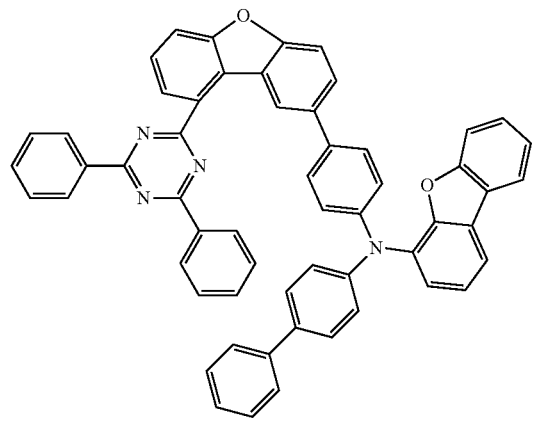
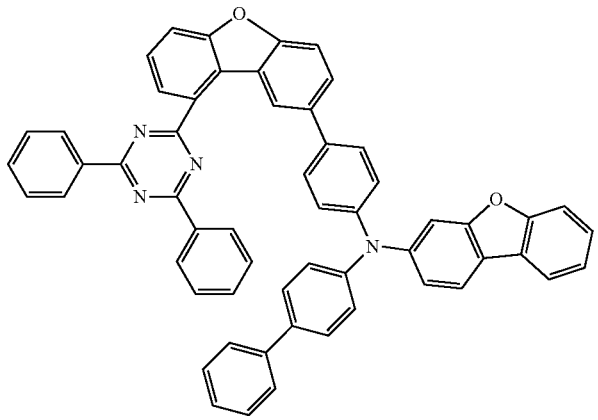
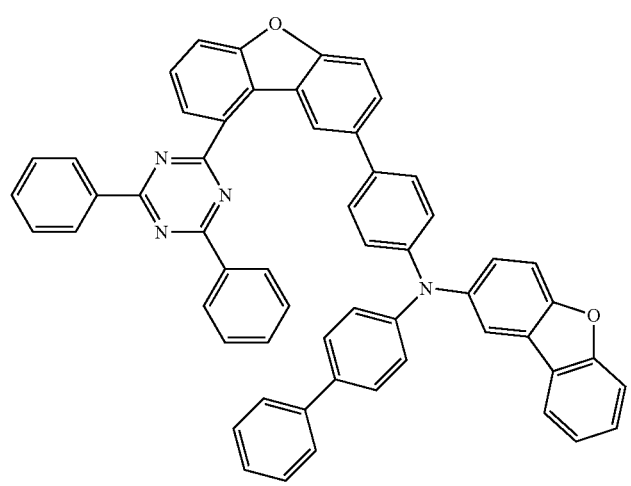
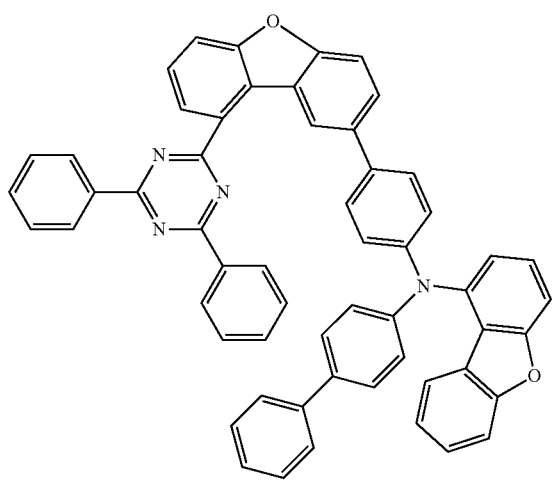
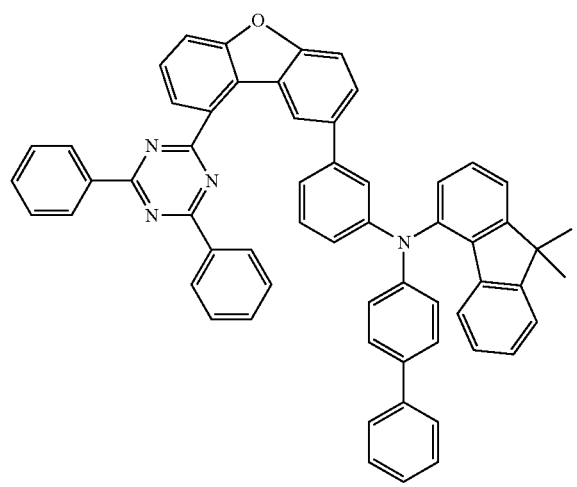
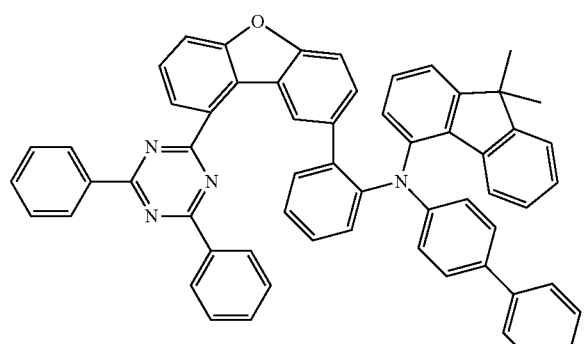

-continued
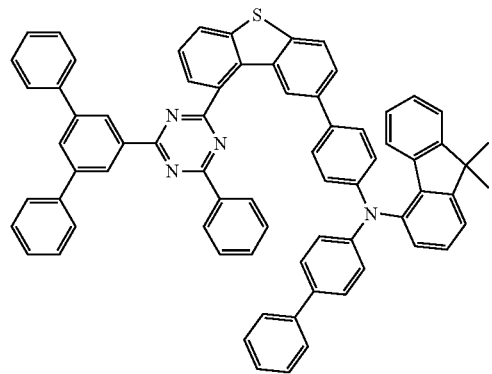
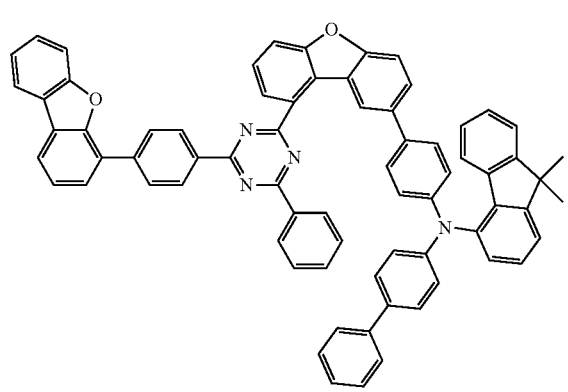
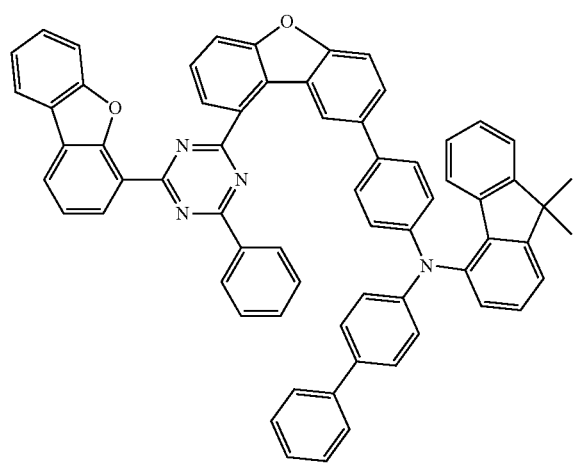
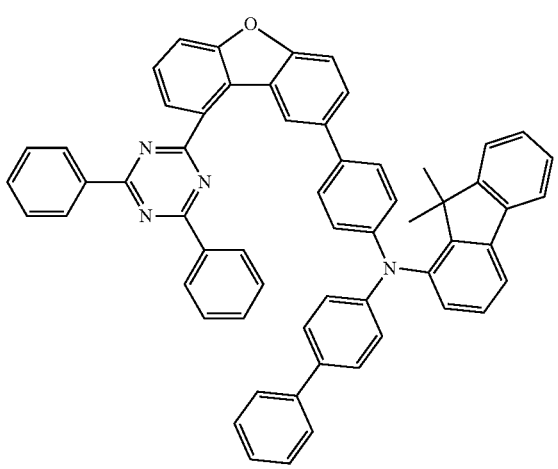
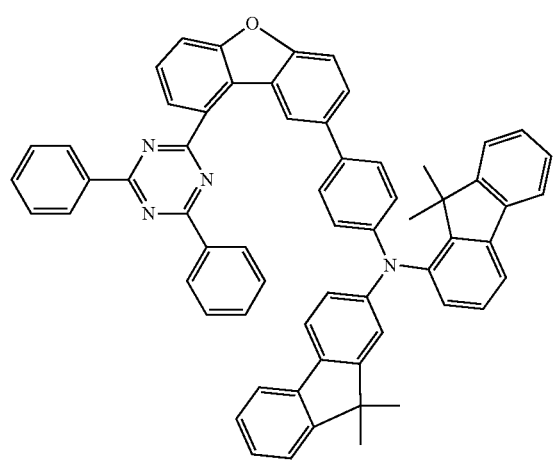

-continued
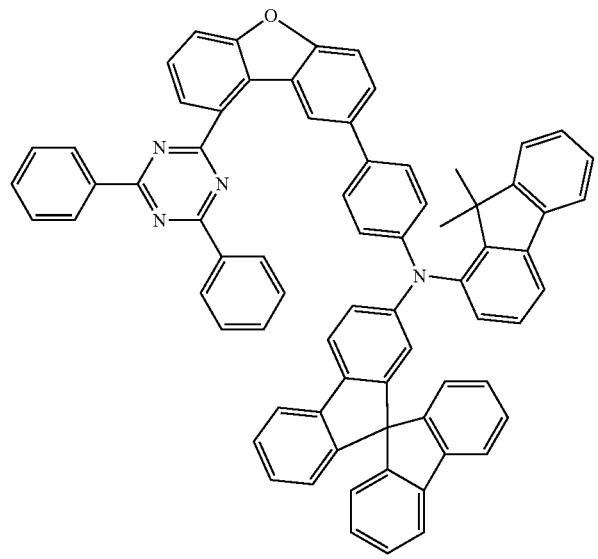
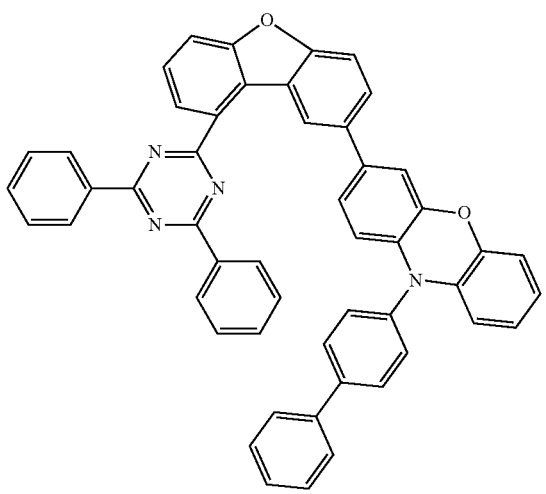
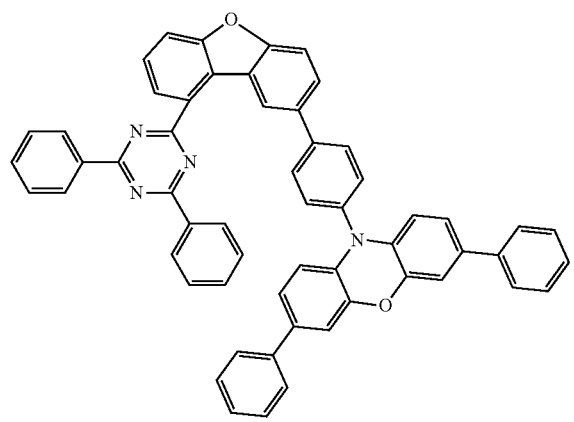
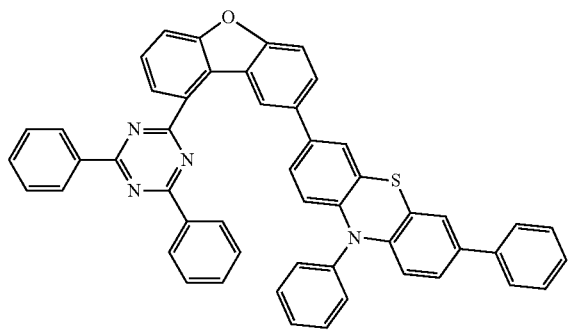
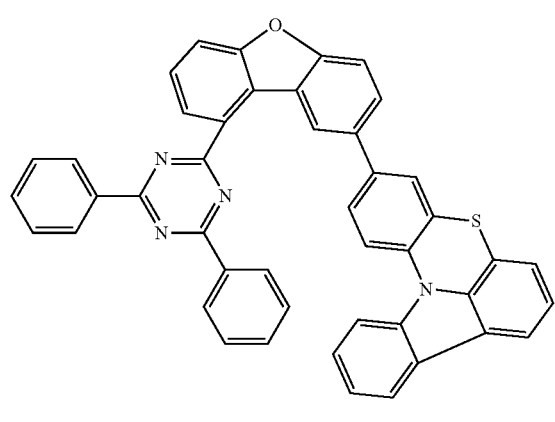
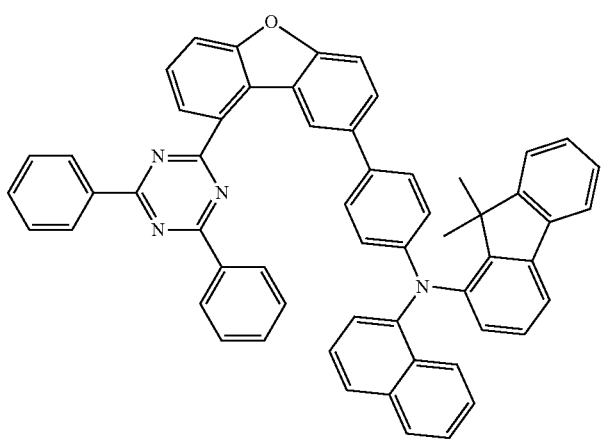

-continued
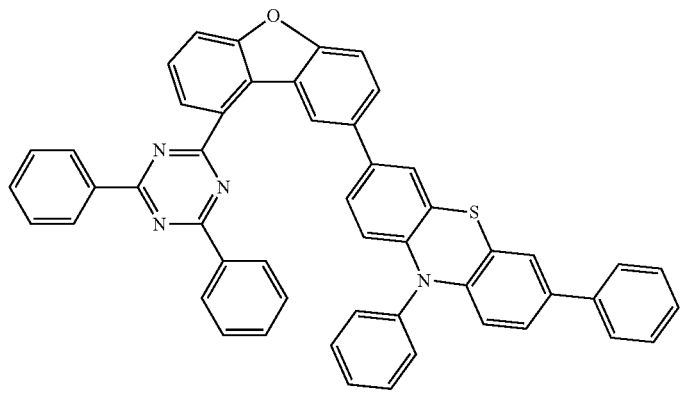
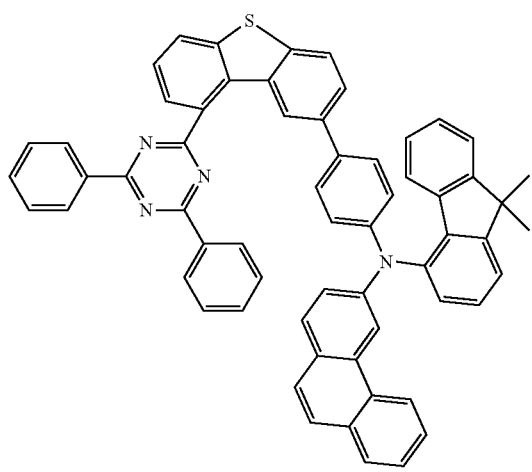
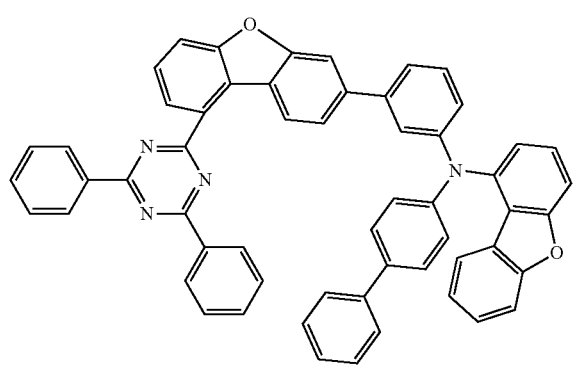
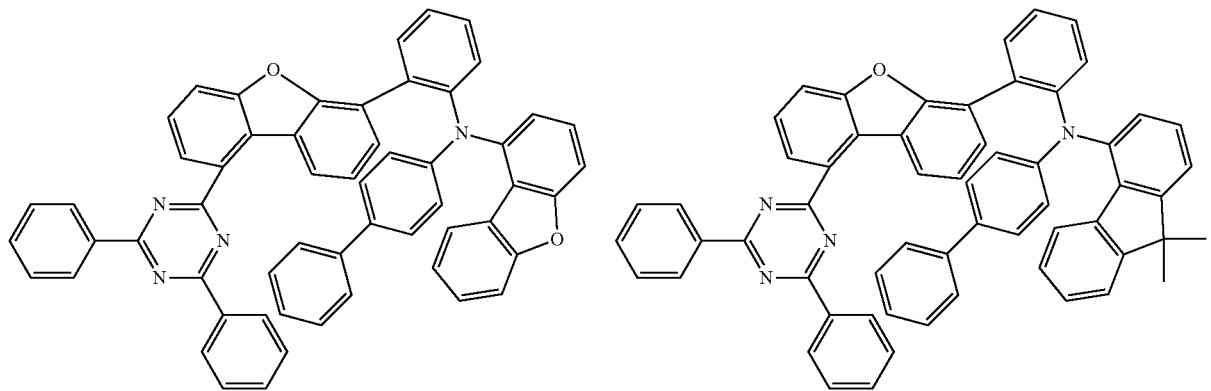

-continued
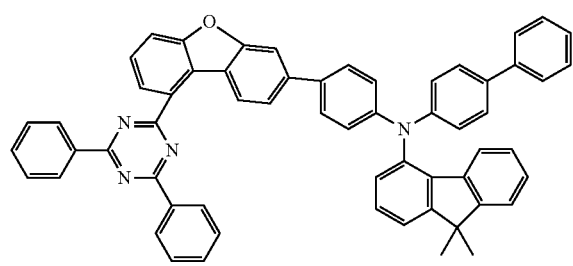
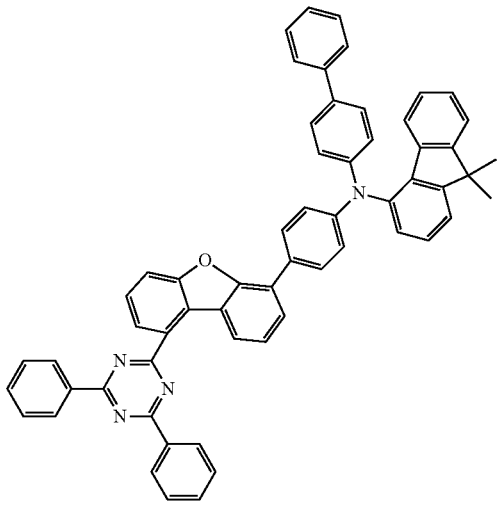
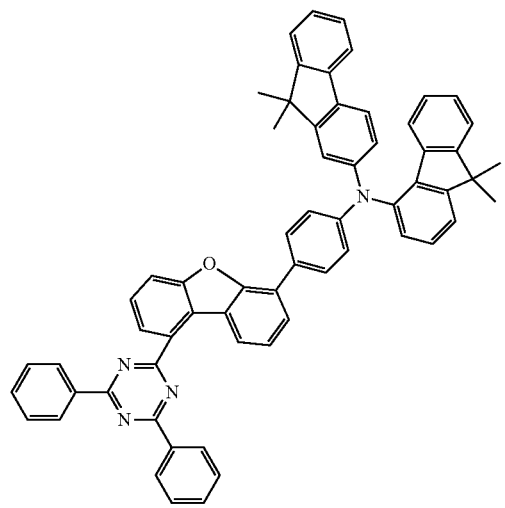
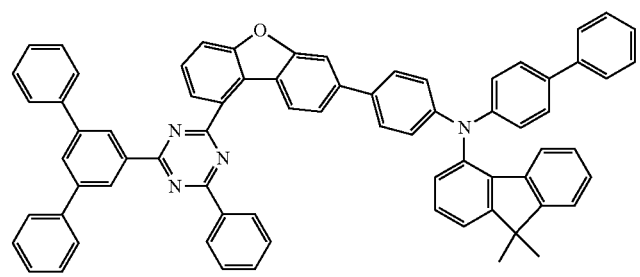
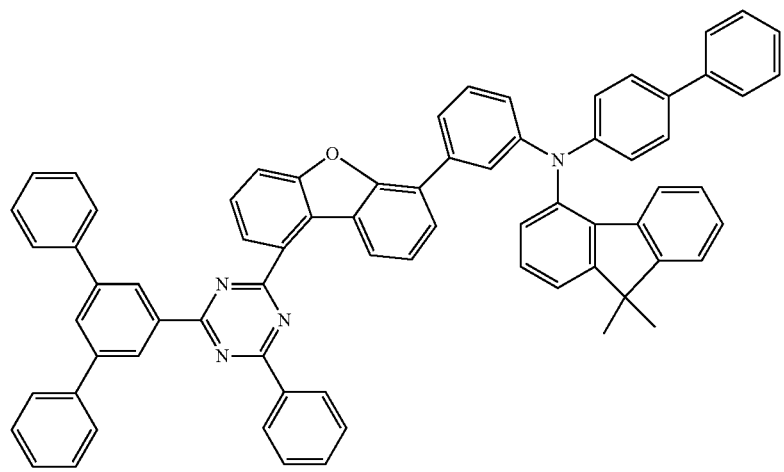

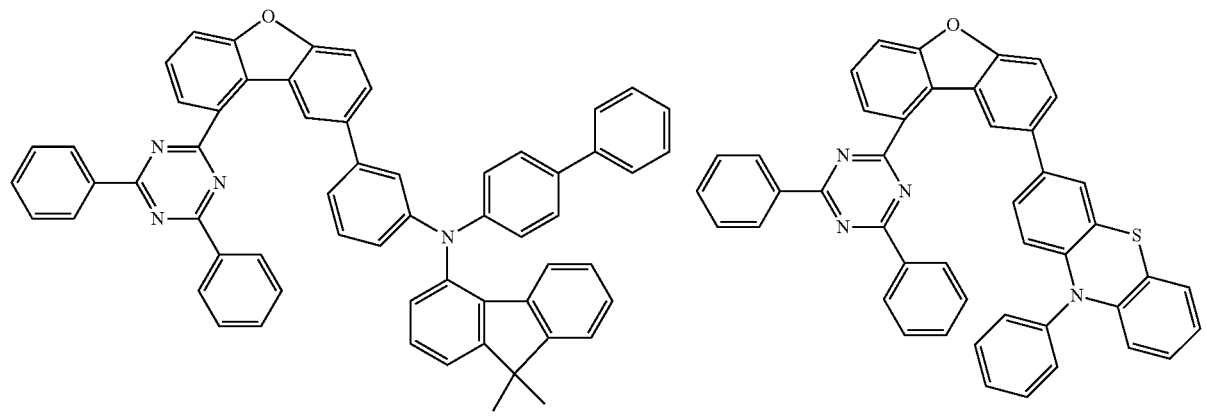
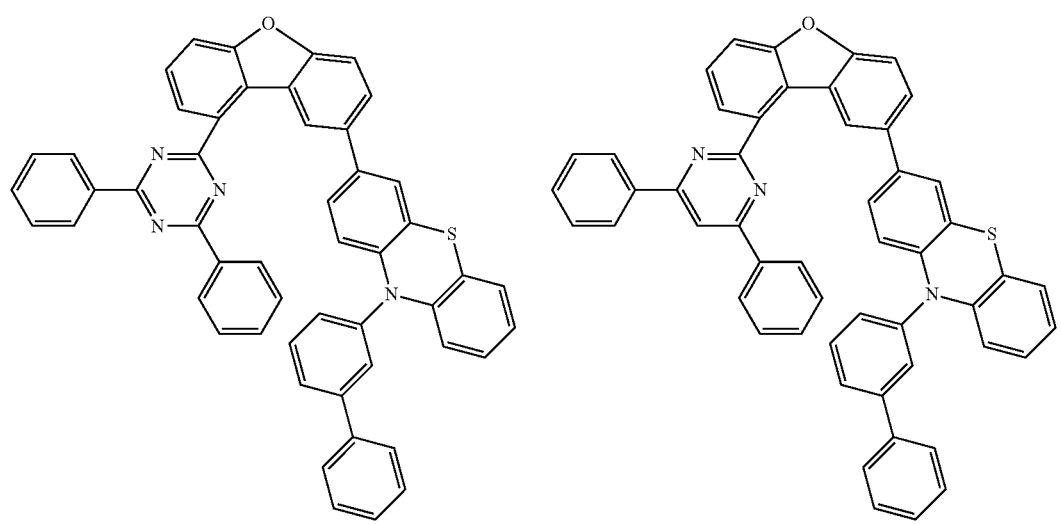
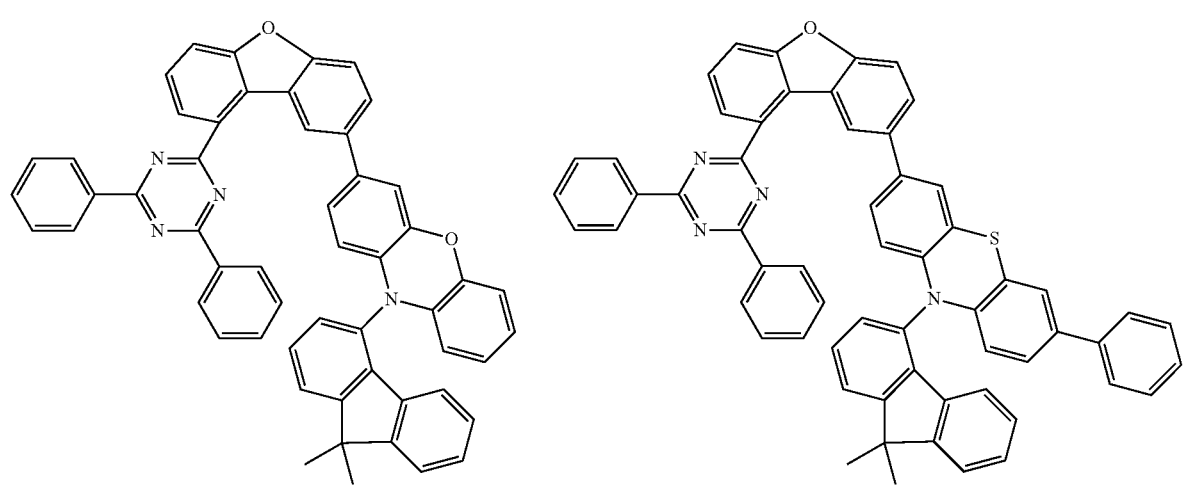

-continued
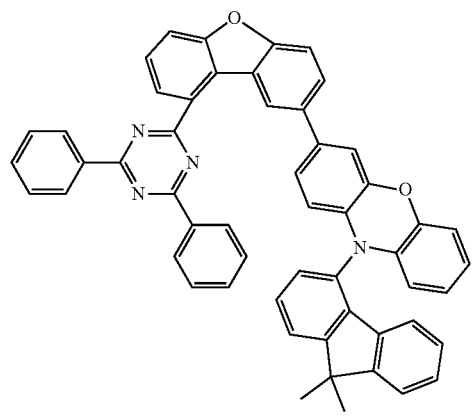
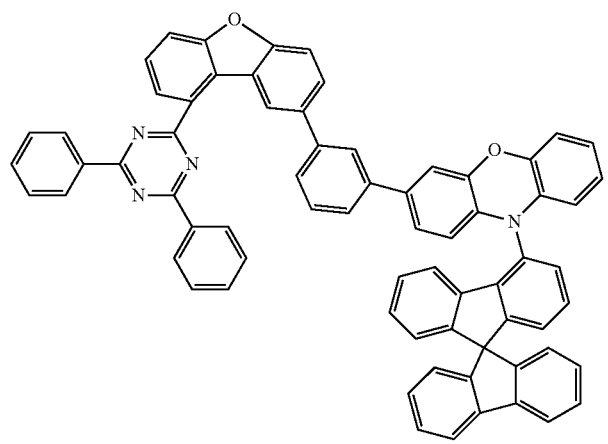
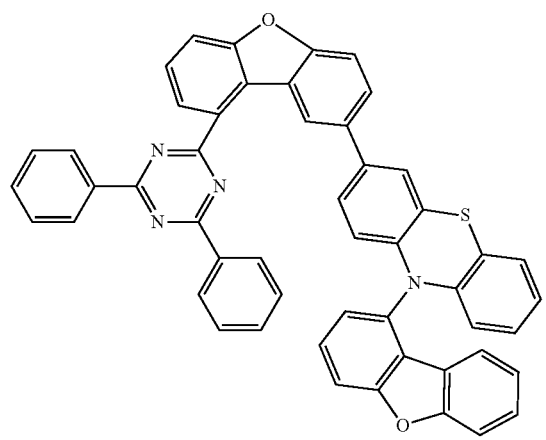
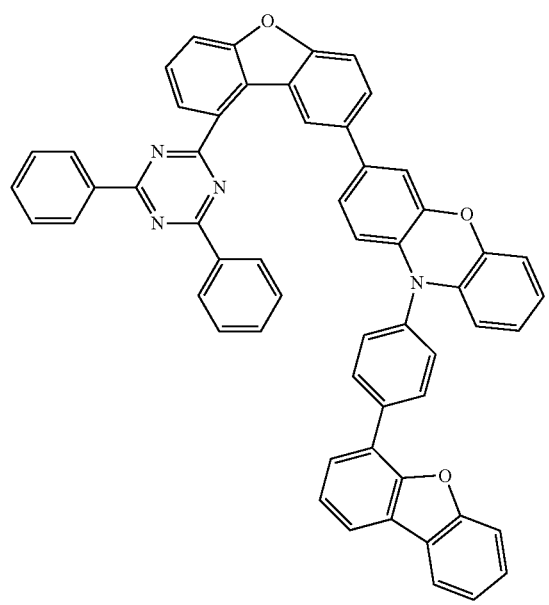
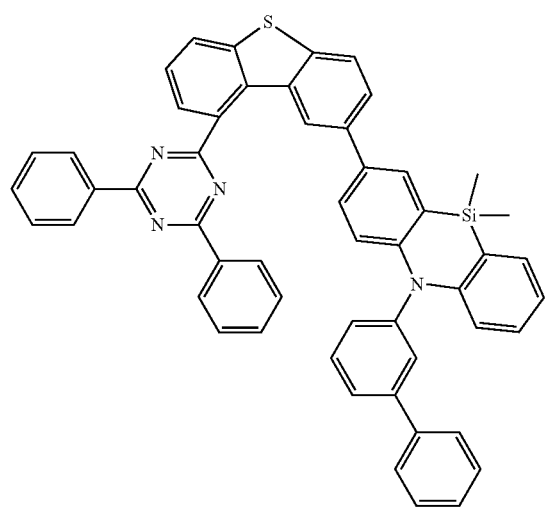
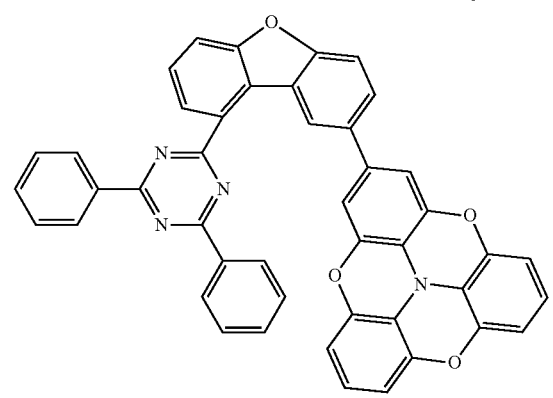

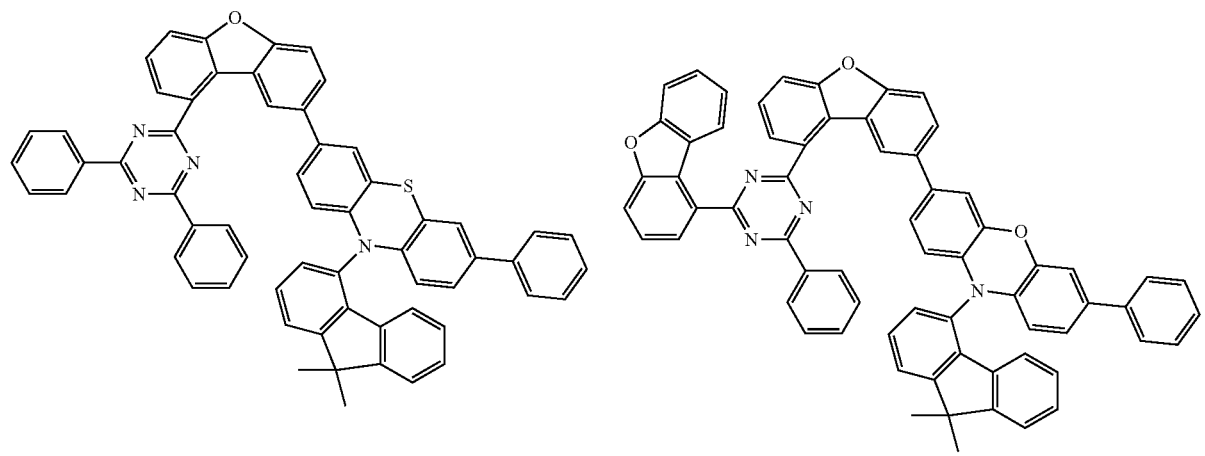
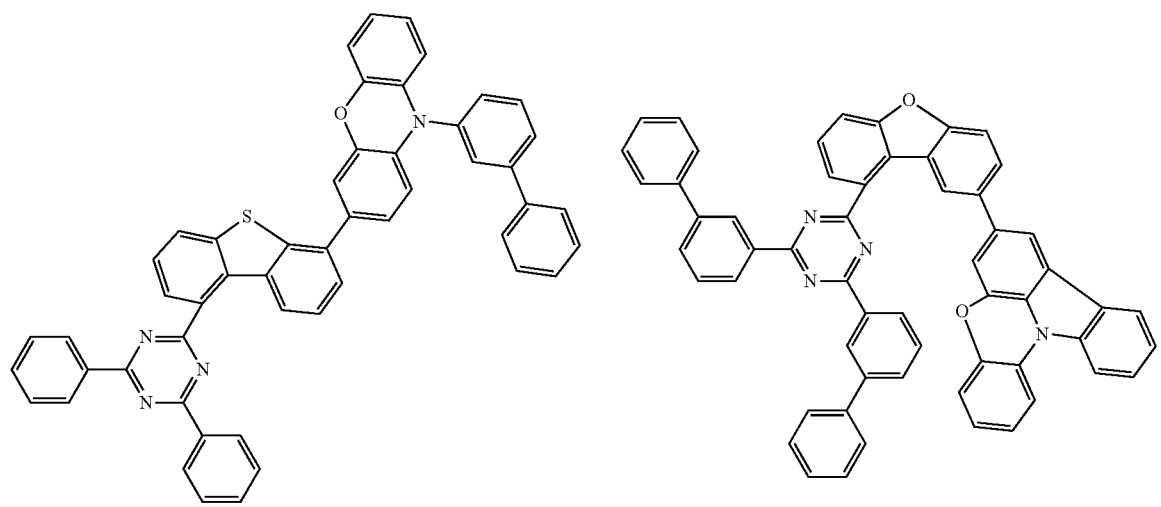
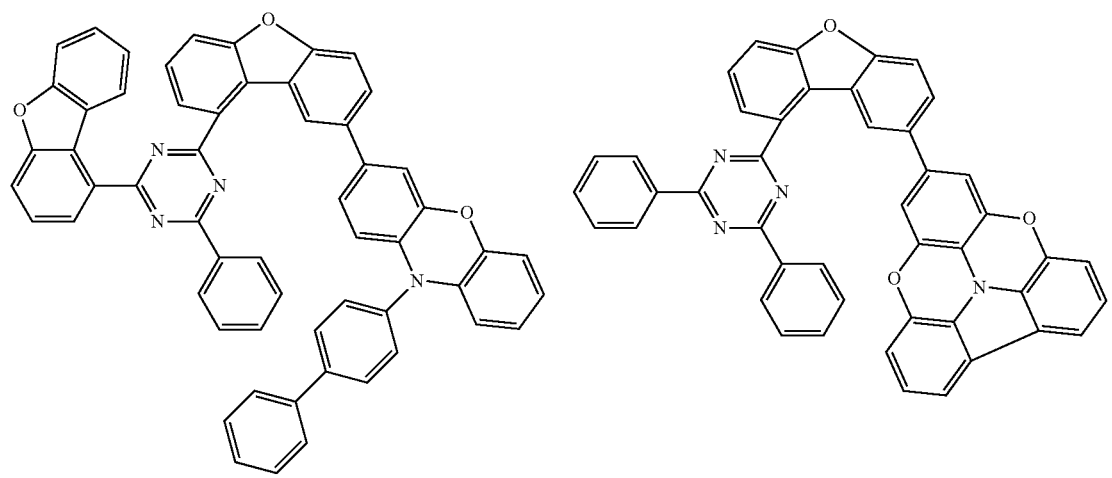

-continued
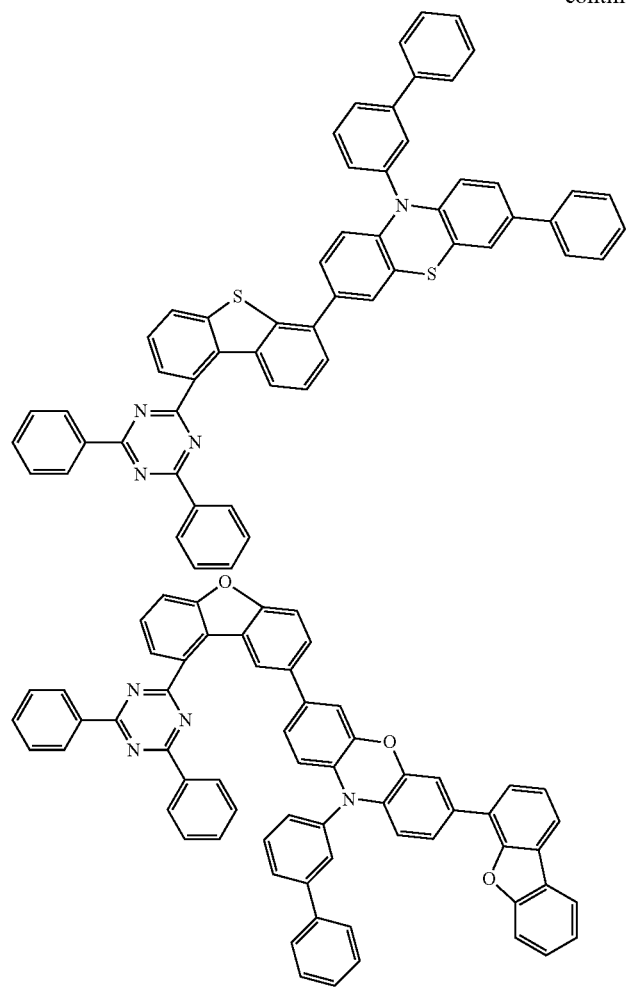
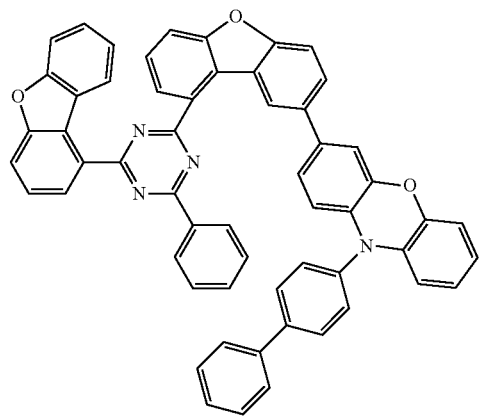
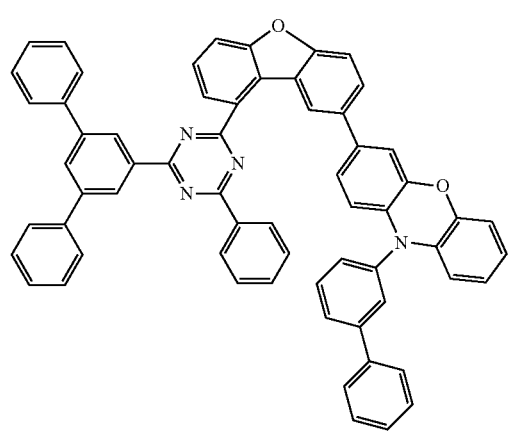
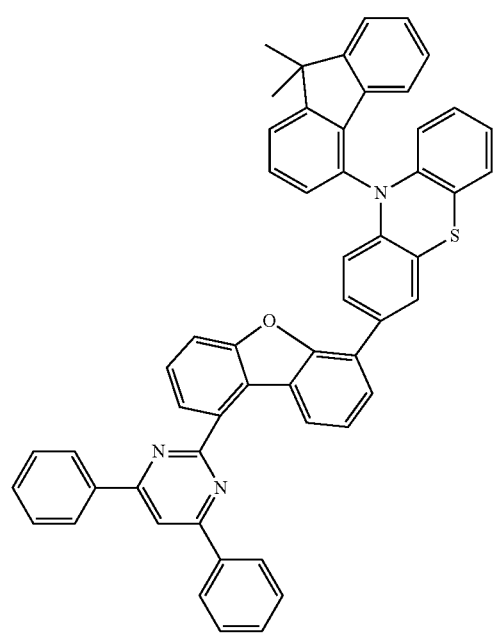
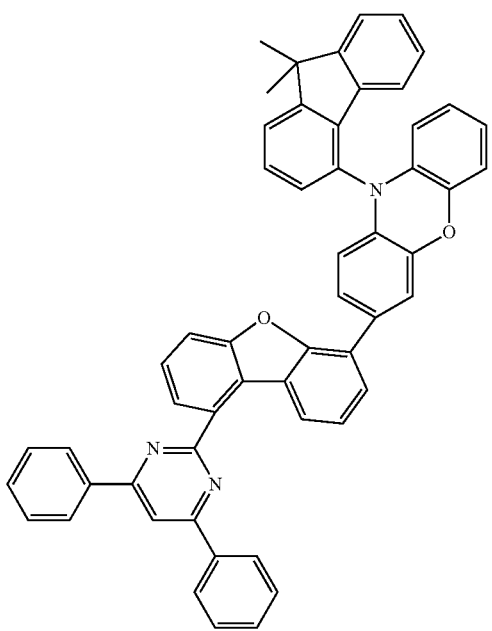

51
52
-continued
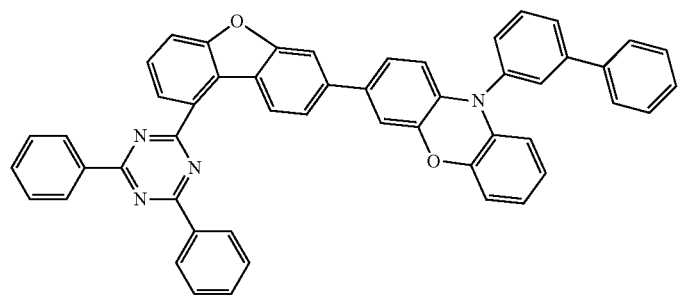
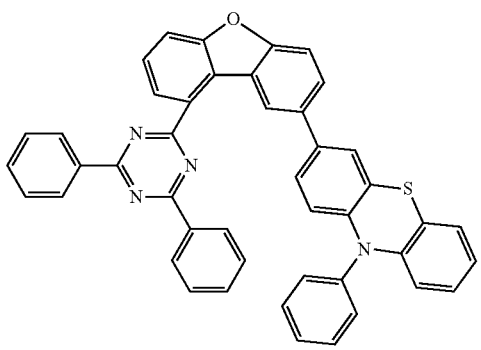
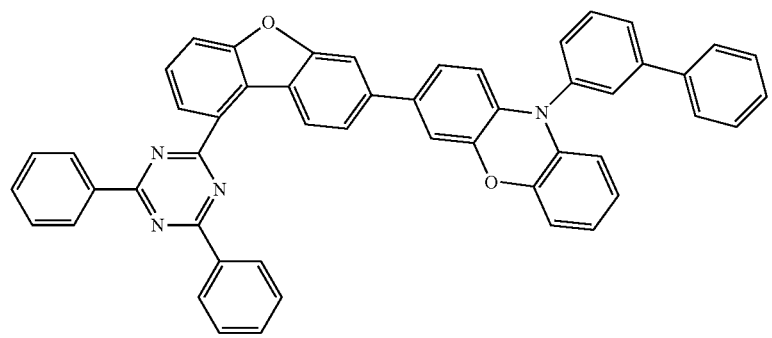
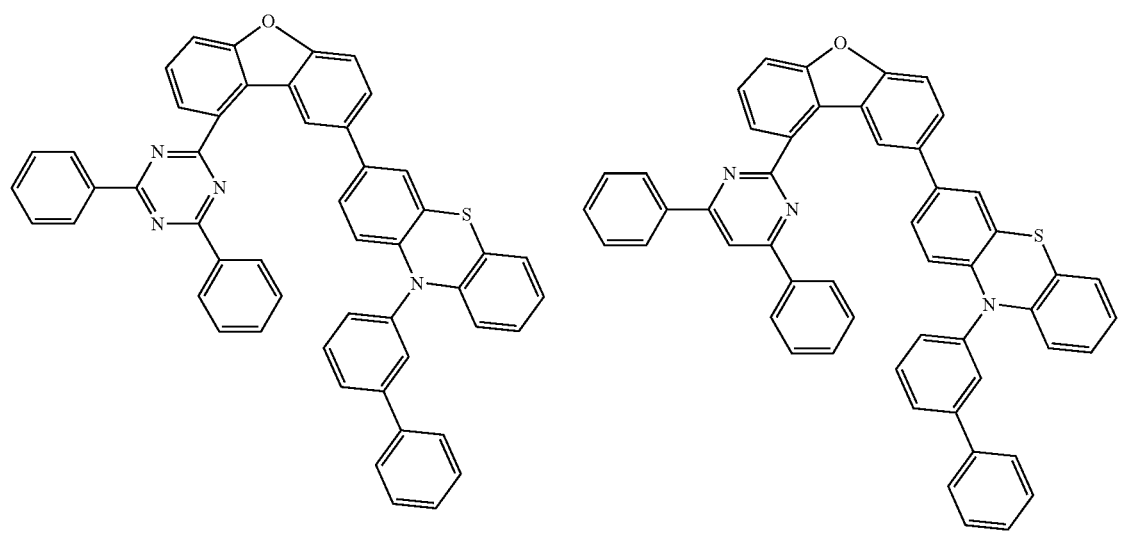
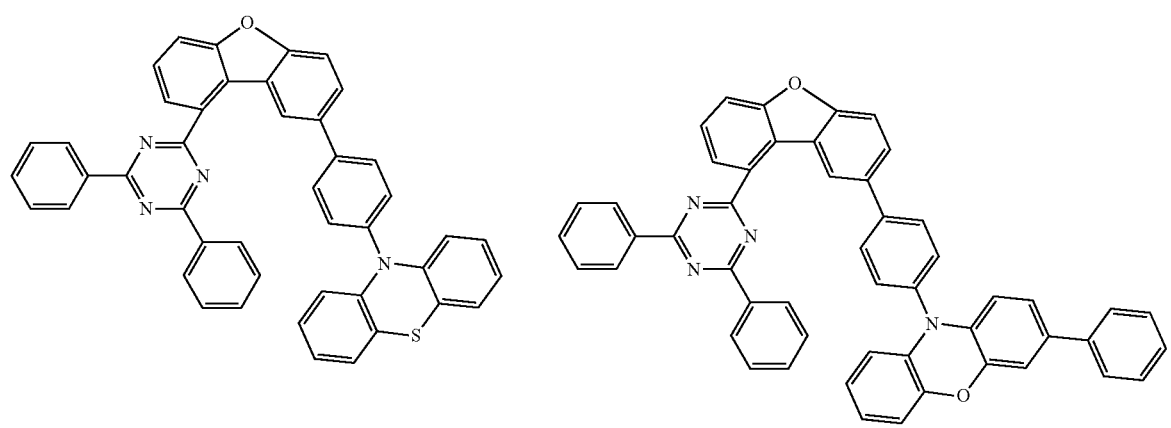

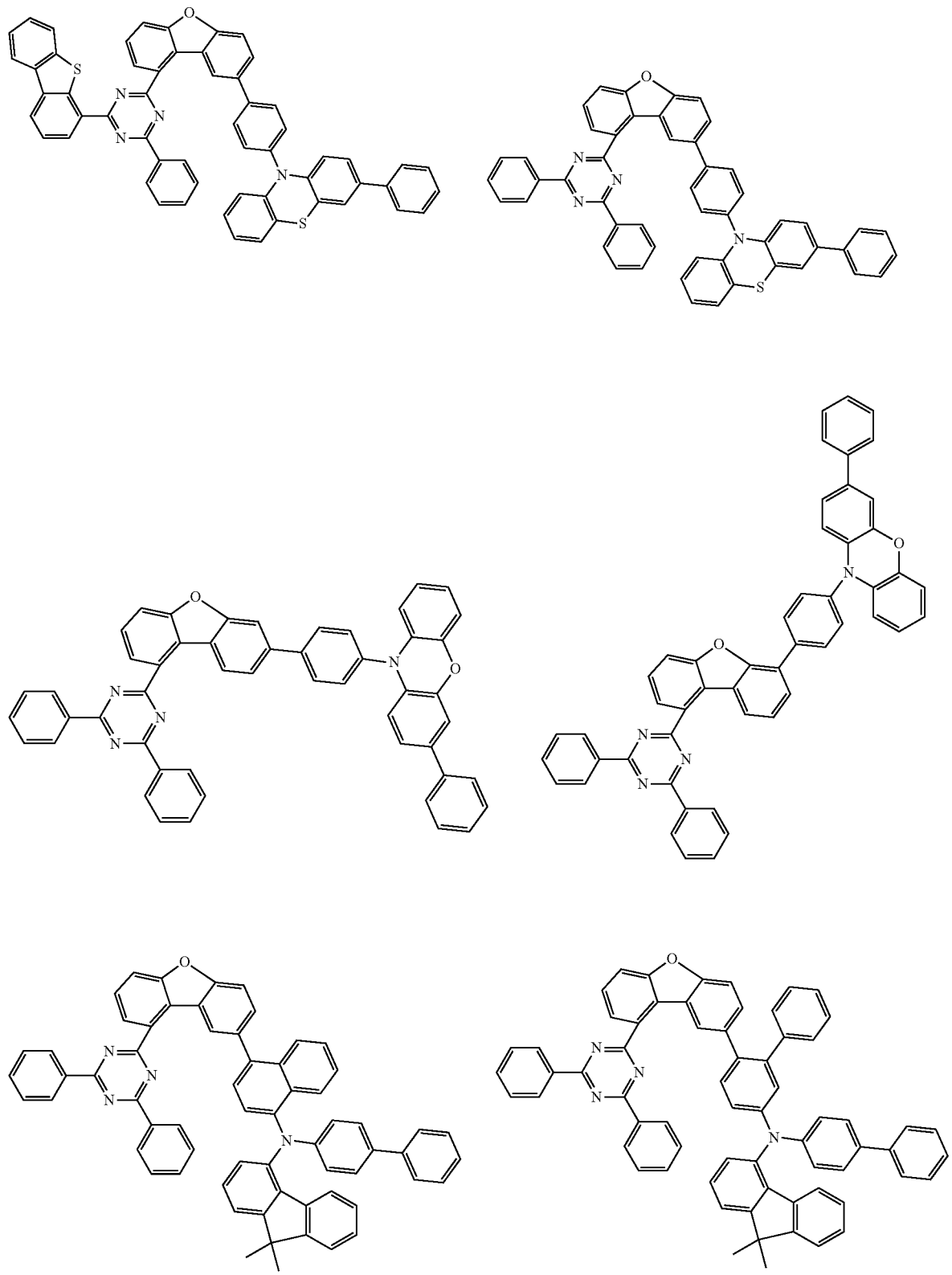

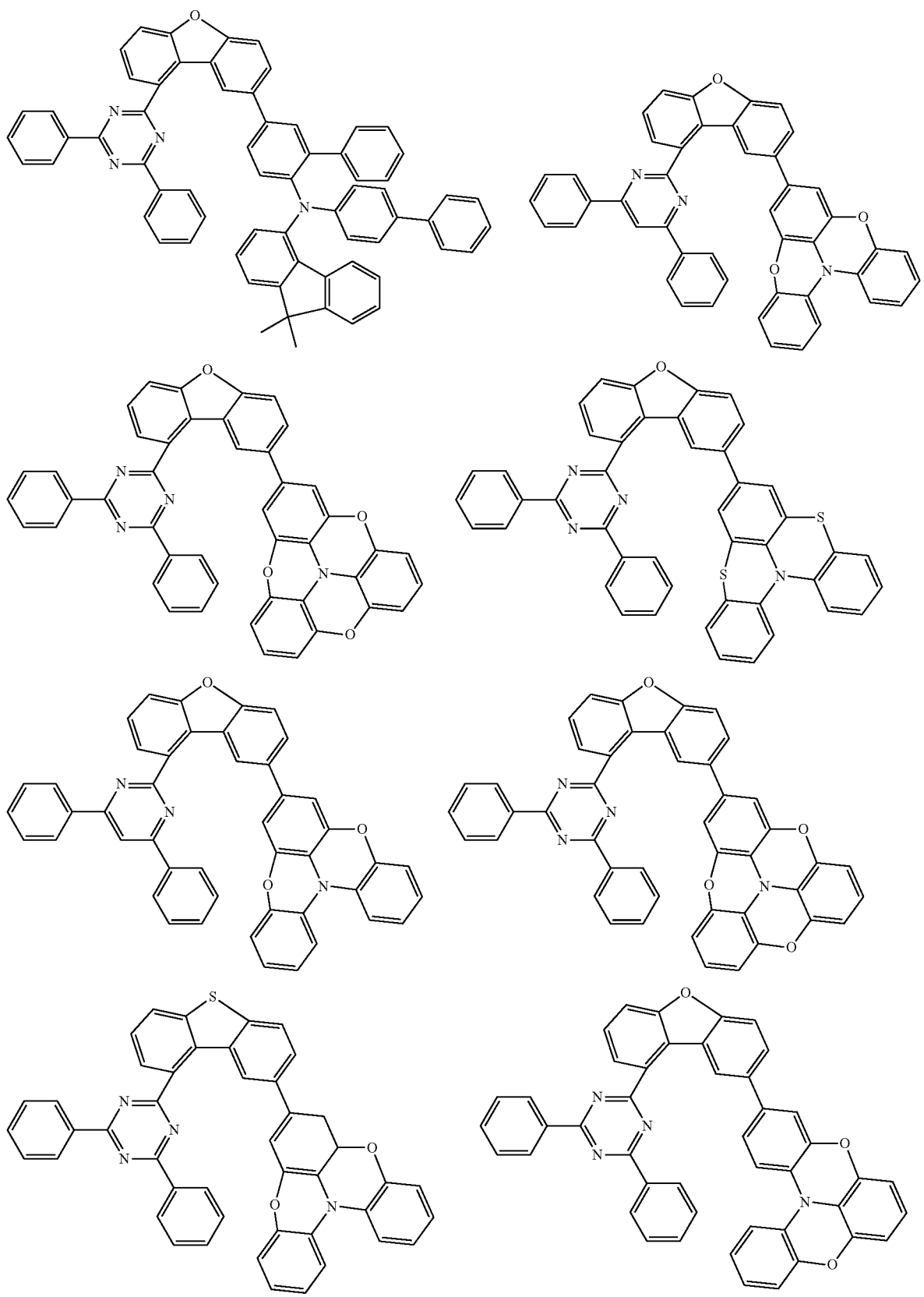

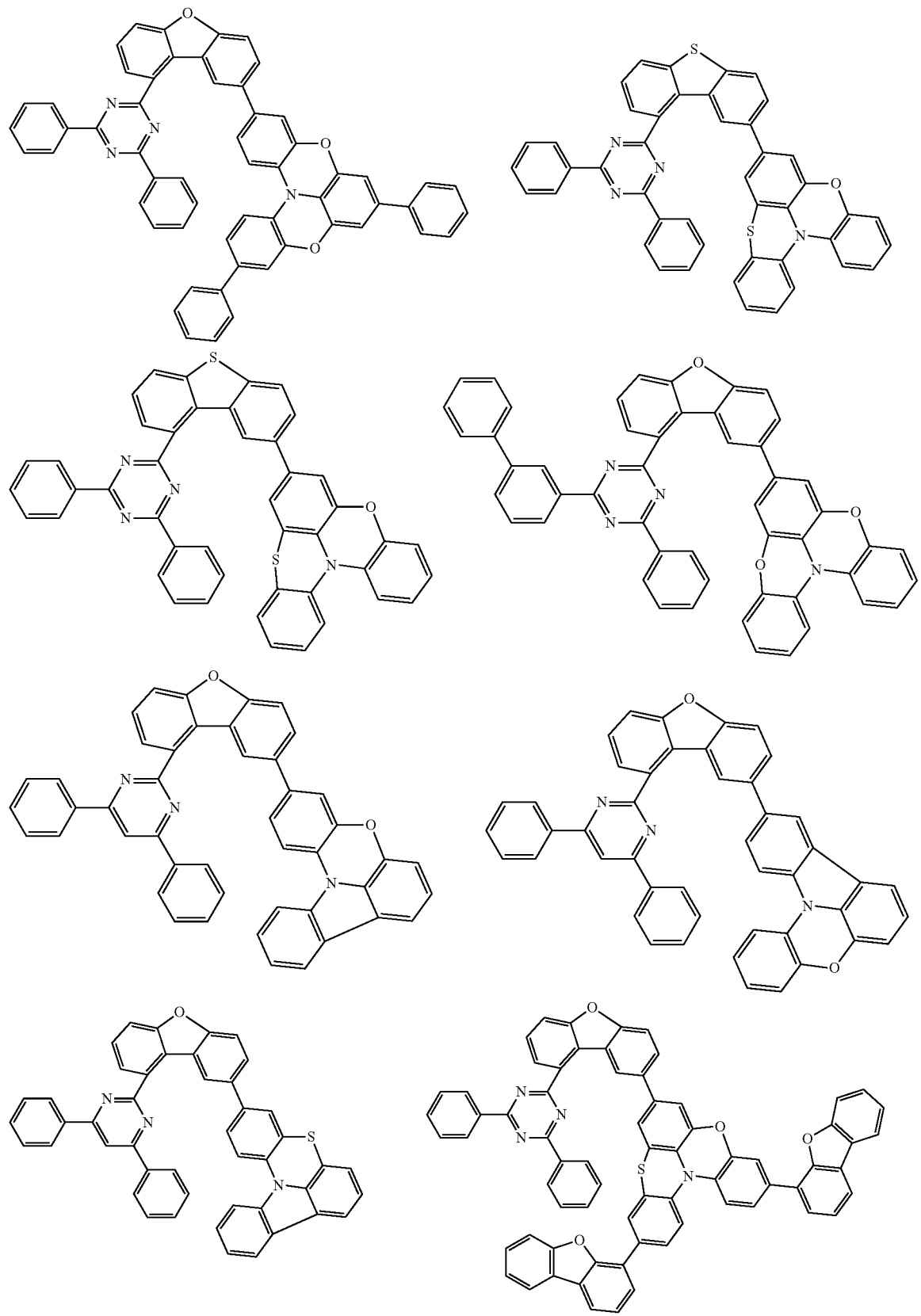

-continued
| 59 | 60 |
|---|---|
| 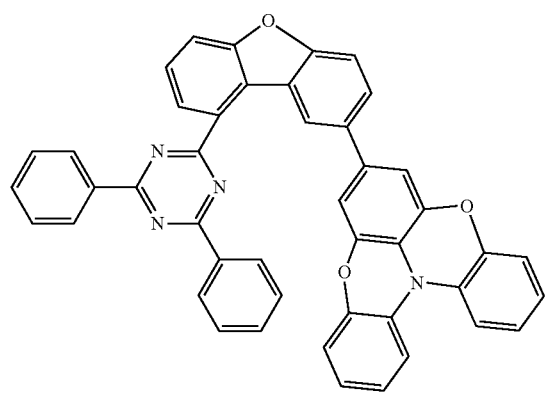 | 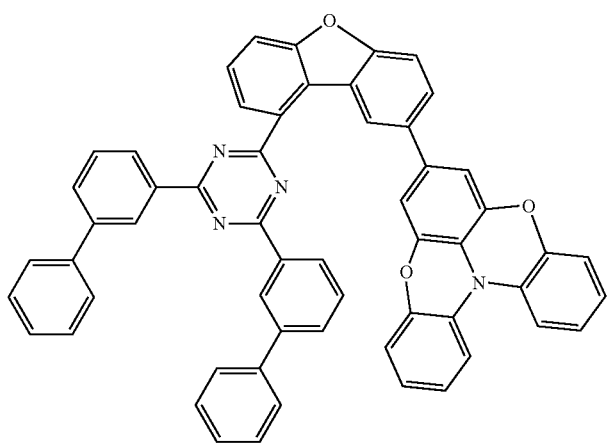 |
| 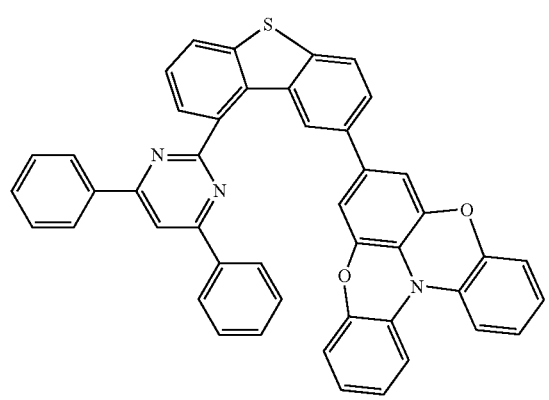 | 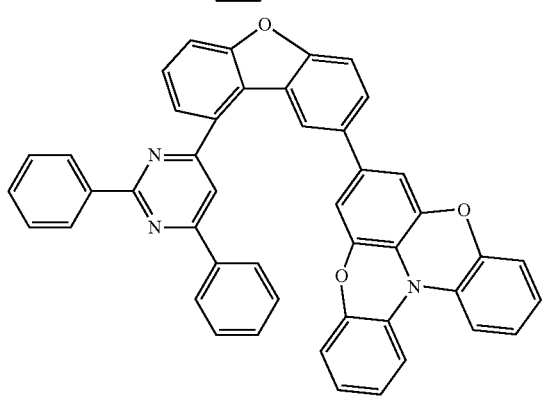 |
| 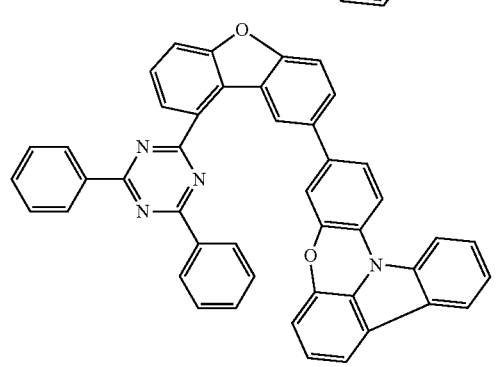 | 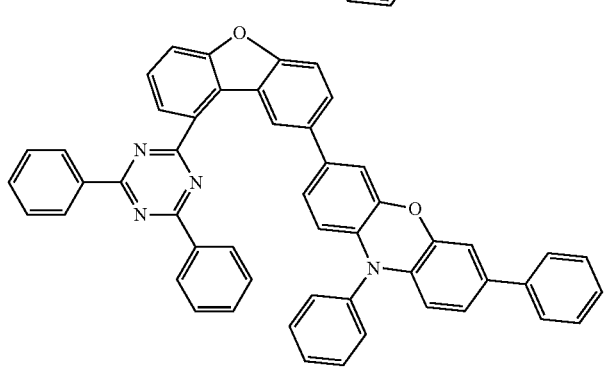 |
| 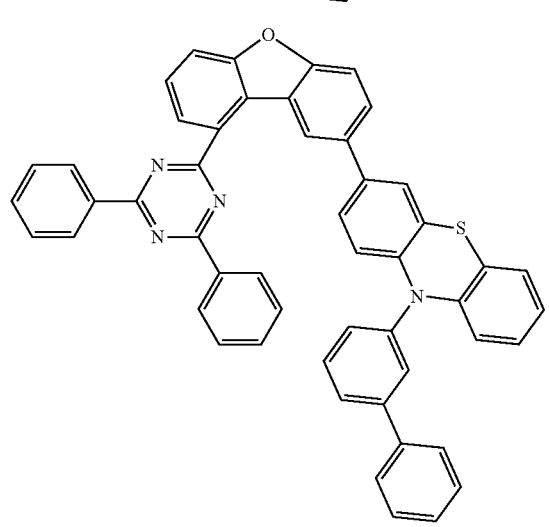 | 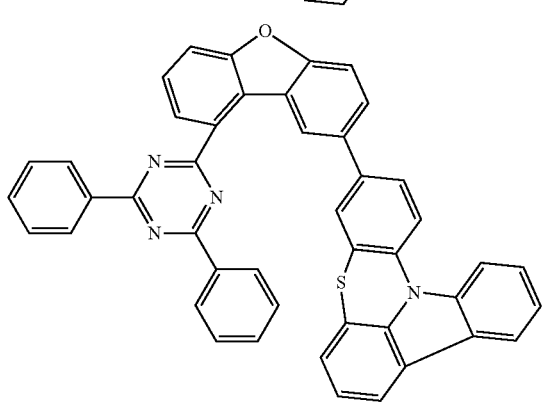 |

-continued
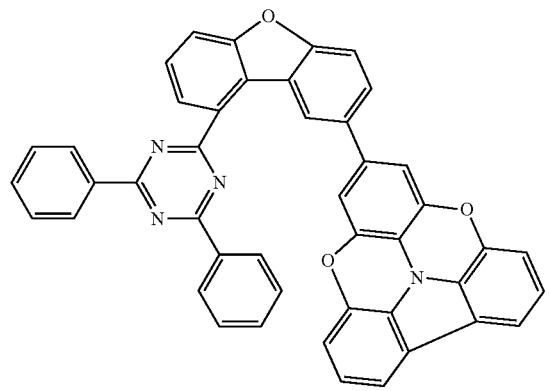
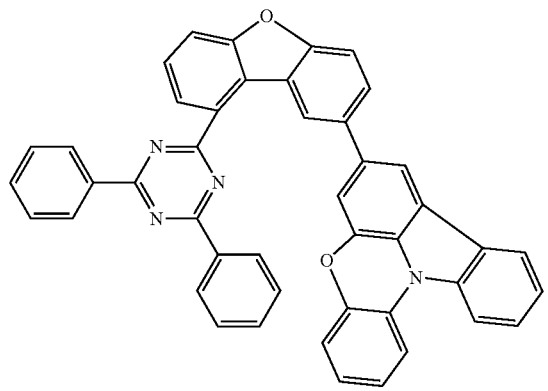
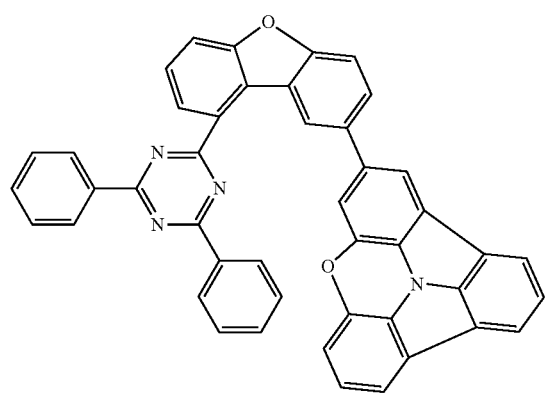
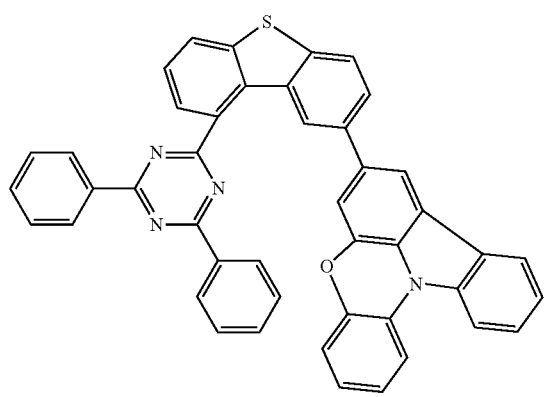
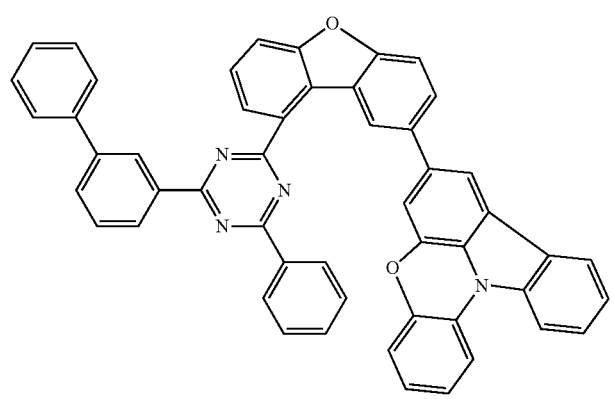
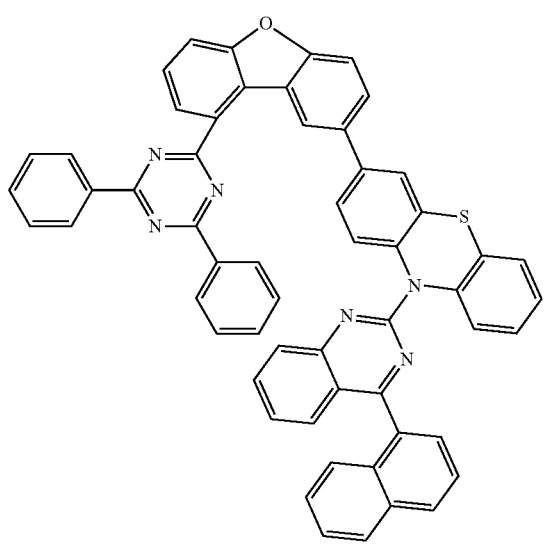

-continued
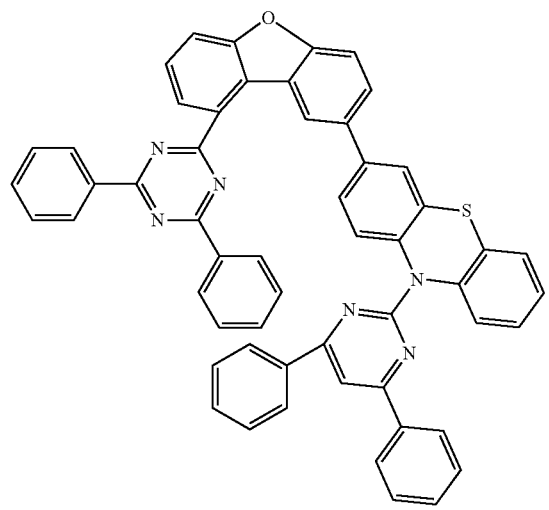
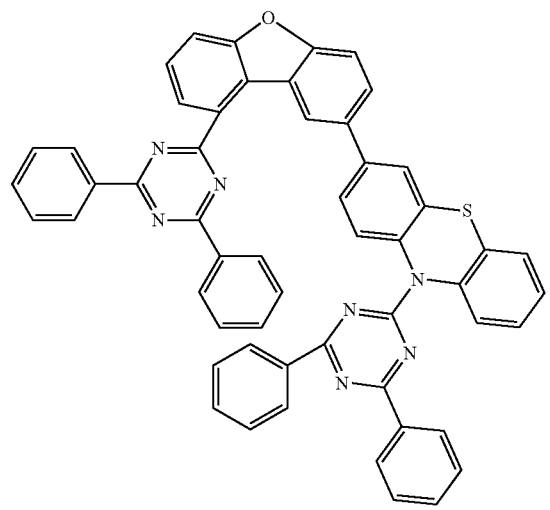
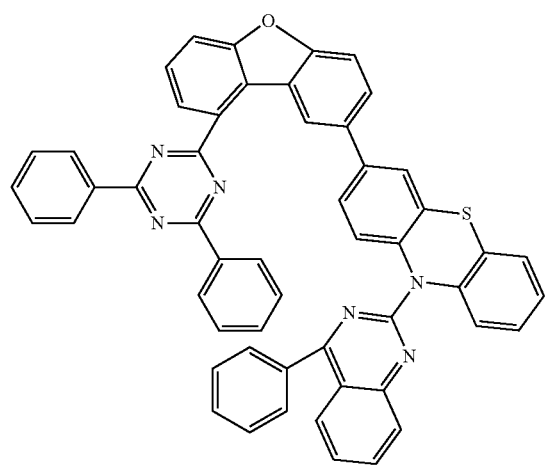
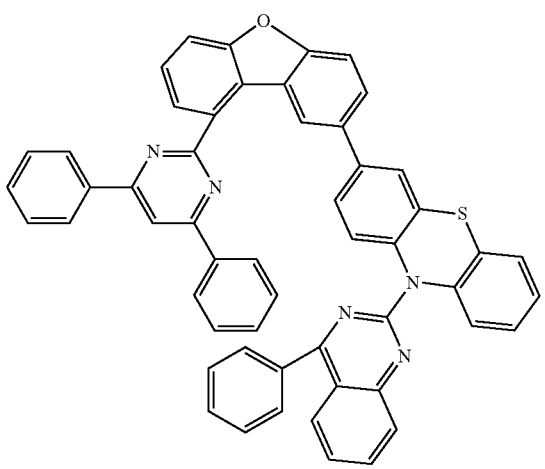
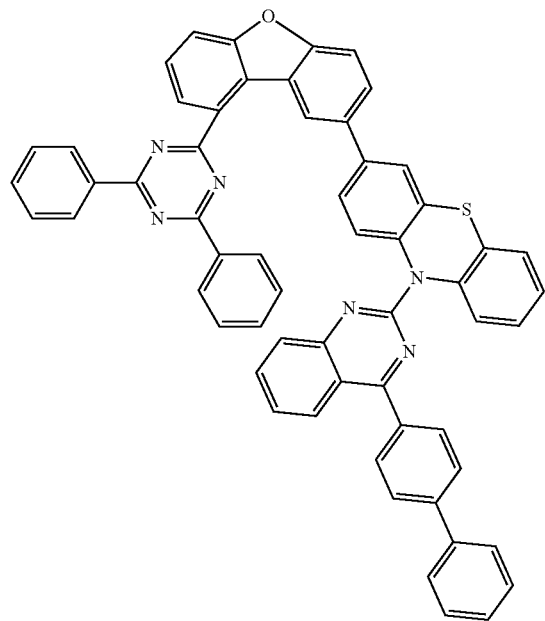
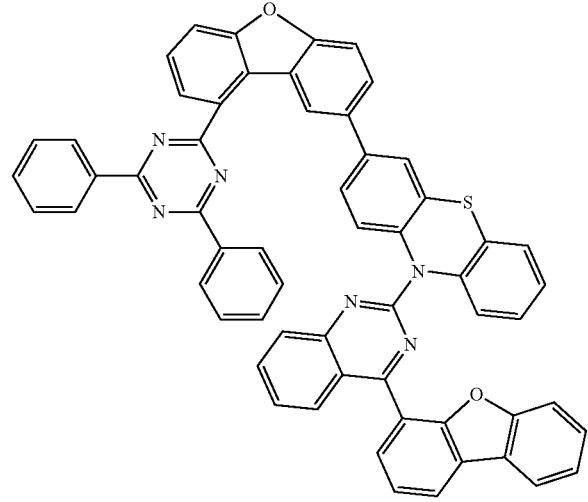

-continued
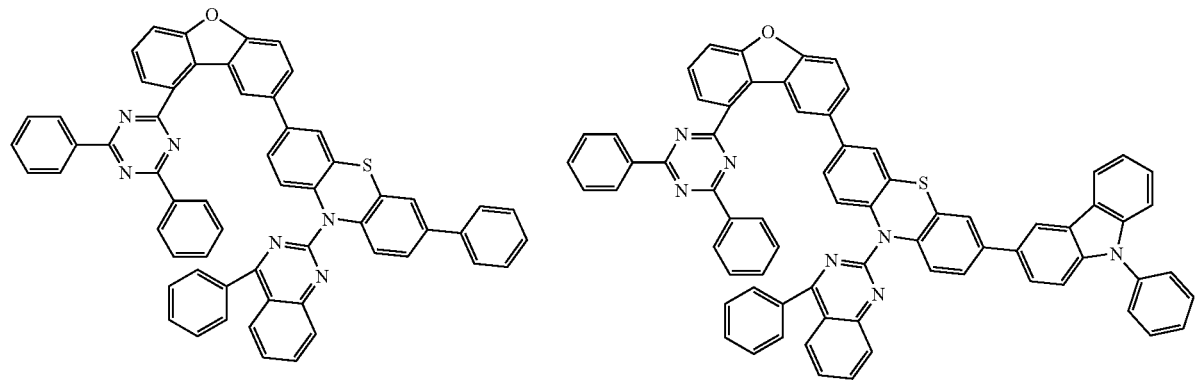
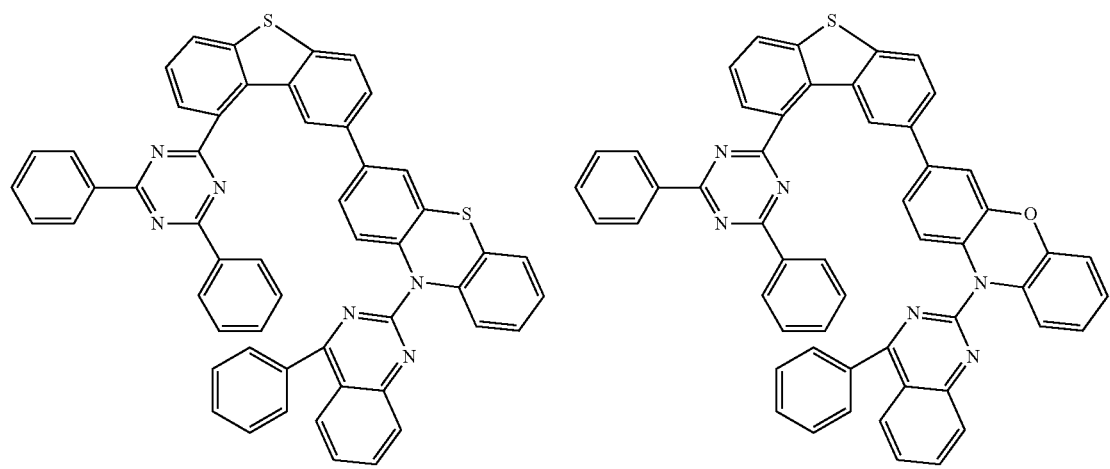
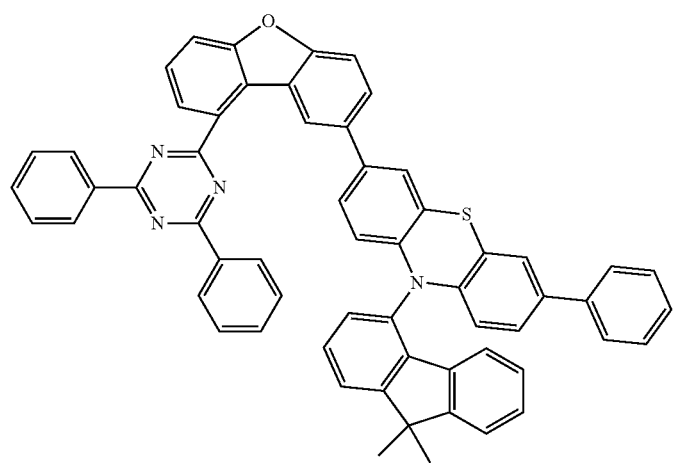

The compounds of the invention can be prepared by synthesis steps known to those skilled in the art, for example bromination, Suzuki coupling, Ullmann coupling, Hartwig-Buchwald coupling, etc.
Suitable synthesis methods are shown in general terms in Schemes 1 to 5 which follow.
Scheme 1
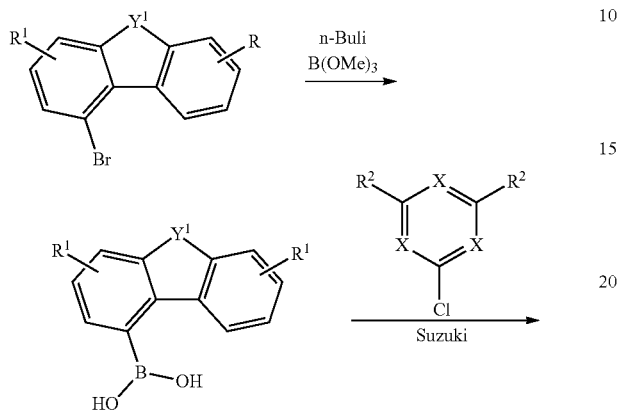
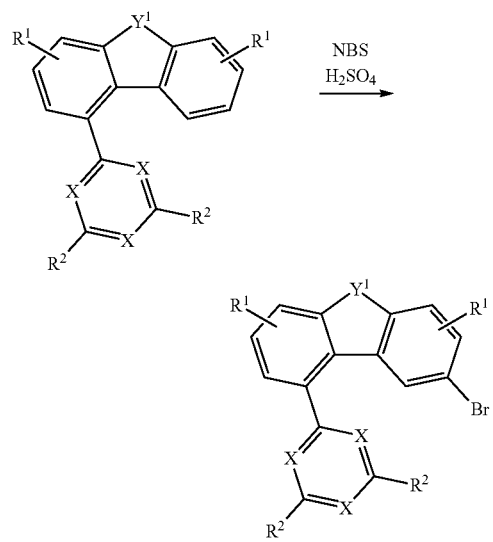
Scheme 2
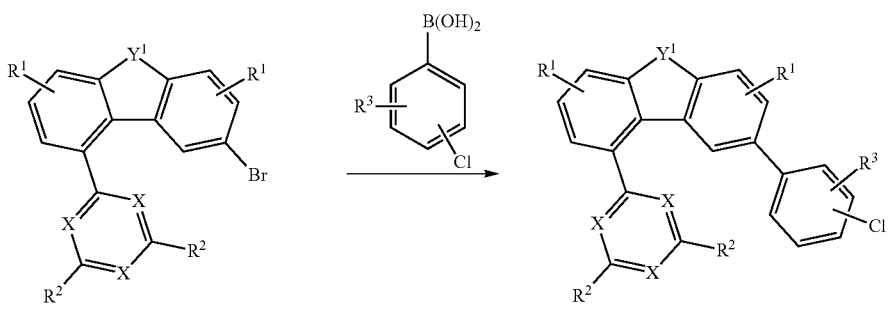
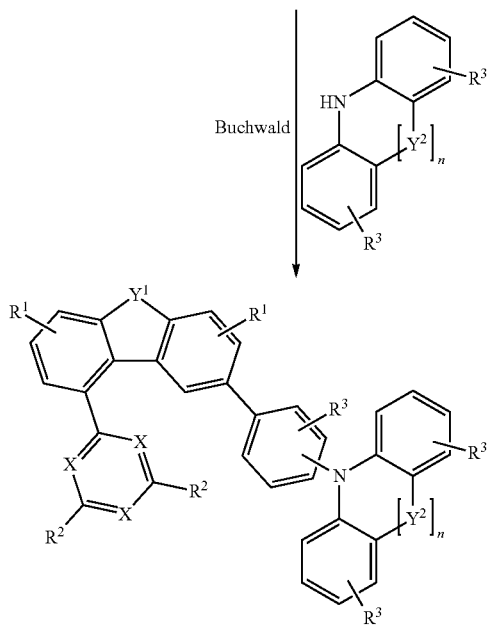

Scheme 3
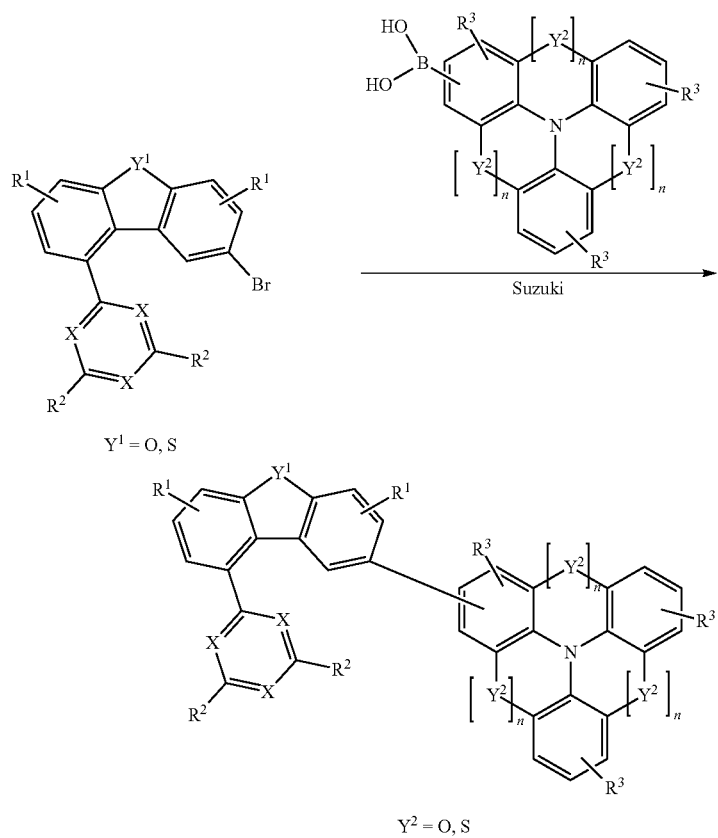
Scheme 4
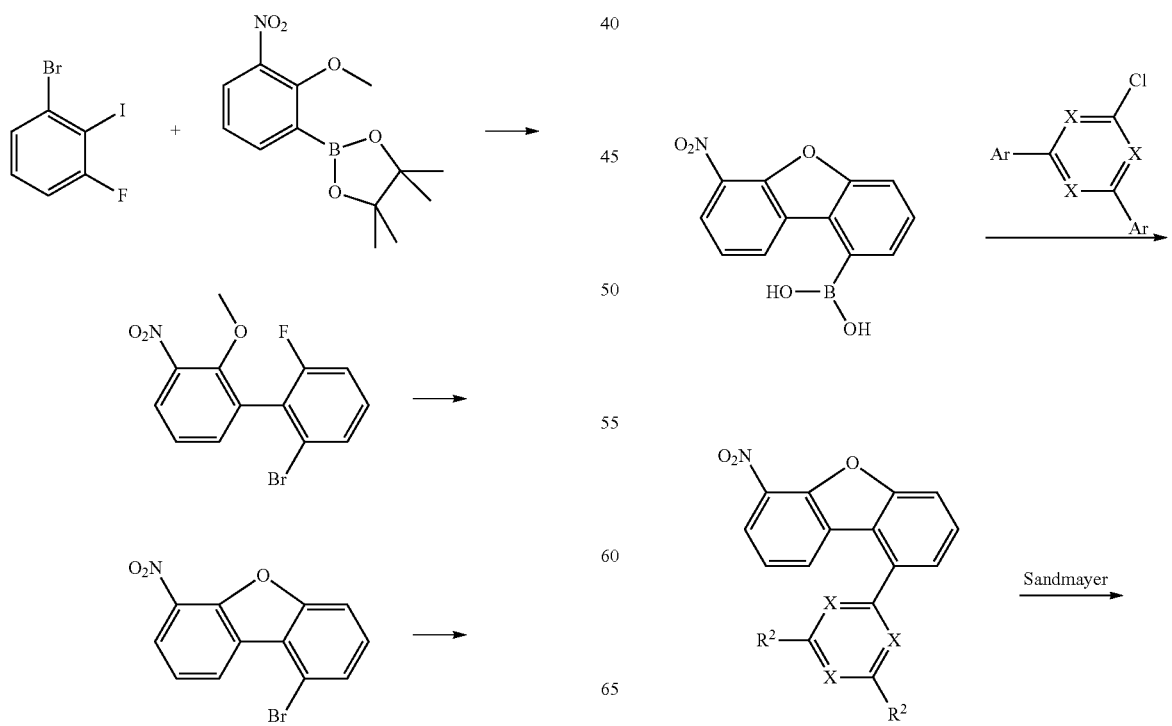

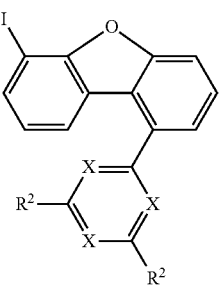

Scheme 5

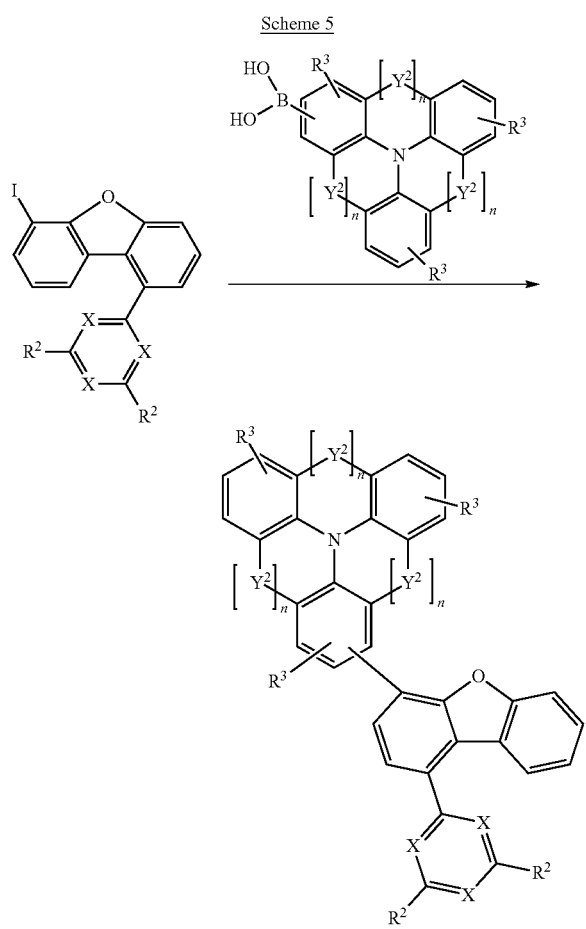

The synthesis proceeds from 1-halodibenzofuran or -dibenzothiophene, which is converted to the corresponding boronic acid or a boronic acid derivative. In the next step, the HetAr group can be introduced by Suzuki coupling. In an analogous manner, it is also possible to introduce an $L^1$-HetAr group. The halogenation, for example with NBS, proceeds selectively in the 8 position of the dibenzofuran or dibenzothiophene. In the last step, it is possible to introduce the N' group in this position, for example by a Hartwig-Buchwald coupling or a Suzuki coupling.

Schemes 4 and 5 show an alternative synthesis method in which the dibenzofuran is constructed in order to be able to introduce the N' group at the 1 position.

The general methods shown for synthesis of the compounds of the invention are illustrative. The person skilled in the art will be able to develop alternative synthesis routes within the scope of his common knowledge in the art.

The present invention further provides a process for synthesizing the compounds of the invention, proceeding from 1-halodibenzofuran or 1-halodibenzothiophene, wherein the halogen is preferably bromine, characterized by the following steps:
(1) optionally converting the halogen group to a boronic acid or boronic acid derivative;
(2) introducing the HetAr or $L^1$-HetAr group by a coupling reaction, especially a Suzuki coupling;
(3) halogenating, especially brominating, the dibenzofuran or dibenzothiophene in the 8 position;
(4) introducing the N' group by a coupling reaction, especially a Hartwig-Buchwald coupling or a Suzuki coupling.

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, 2-methylbiphenyl, 3-methylbiphenyl, 1-methylnaphthalene, 1-ethylnaphthalene, ethyl octanoate, diethyl sebacate, octyl octanoate, heptylbenzene, menthyl isovalerate, cyclohexyl hexanoate or mixtures of these solvents.

The present invention therefore further provides a formulation comprising a compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound, especially a phosphorescent dopant, and/or a further matrix material. Suitable emitting compounds and further matrix materials are listed at the back in connection with the organic electroluminescent device. This further compound may also be polymeric.

The compounds and mixtures of the invention are suitable for use in an electronic device. An electronic device is understood here to mean a device containing at least one layer containing at least one organic compound. The component may, however, also comprise inorganic materials or else layers formed entirely from inorganic materials.

The present invention therefore further provides for the use of the compounds or mixtures of the invention in an electronic device, especially in an organic electroluminescent device.

The present invention still further provides an electronic device comprising at least one of the above-detailed compounds or mixtures of the invention. In this case, the preferences detailed above for the compound also apply to the electronic devices.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitized solar cells, organic optical detectors, organic photoreceptors, organic field-quench devices (O-FQDs), light-emitting electrochemical cells (LECs), organic laser diodes (O-lasers) and organic plasmon emitting devices, preferably organic electroluminescent devices (OLEDs, PLEDs), especially phosphorescent OLEDs.

The organic electroluminescent device comprises cathode, anode and at least one emitting layer. Apart from these layers, it may also comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers show blue, green and orange or red emission (for the basic construction, see, for example, WO 2005/011013). Preference is further given to tandem OLEDs. These may be fluorescent or phosphorescent emission layers or else hybrid systems in which fluorescent and phosphorescent emission layers are combined with one another.

The compound of the invention according to the above-detailed embodiments may be used in different layers, according to the exact structure. Preference is given to an organic electroluminescent device comprising a compound of formula (1) or as per the preferred embodiments as matrix material for fluorescent or phosphorescent emitters or for emitters that exhibit TADF (thermally activated delayed fluorescence), especially for phosphorescent emitters, and/or in an electron transport layer and/or in an electron-blocking or exciton-blocking layer and/or in a hole transport layer, according to the exact substitution. In this context, the above-detailed preferred embodiments also apply to the use of the materials in organic electronic devices.

In a preferred embodiment of the invention, the compound of formula (1) or according to the preferred embodiments is used as matrix material for a fluorescent or phosphorescent compound, especially for a phosphorescent compound, in an emitting layer. In this case, the organic electroluminescent device may contain an emitting layer, or it may contain a plurality of emitting layers, where at least one emitting layer contains at least one compound of the invention as matrix material. It is a particular feature of the compounds of the invention that they have advantageous properties even with phosphorescent emitters containing ketoketonate ligands.

When the compound of formula (1) or according to the preferred embodiments is used as matrix material for an emitting compound in an emitting layer, it is preferably used in combination with one or more phosphorescent materials (triplet emitters). Phosphorescence in the context of this invention is understood to mean luminescence from an excited state having spin multiplicity >1, especially from an excited triplet state.

The mixture of the compound of formula (1) or according to the preferred embodiments and the emitting compound contains between 99% and 1% by volume, preferably between 98% and 10% by volume, more preferably between 97% and 60% by volume and especially between 95% and 80% by volume of the compound of formula (1) or according to the preferred embodiments, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

A further preferred embodiment of the present invention is the use of the compound of formula (1) or according to the preferred embodiments as matrix material for a phosphorescent emitter in combination with a further matrix material. Particularly suitable matrix materials which can be used in combination with the compounds of formula (1) or according to the preferred embodiments are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109 and WO 2011/000455, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, dibenzofuran derivatives, for example according to WO 2017/148564 or WO 2017/148565, or lactams, for example according to WO 2011/116865 or WO 2011/137951. It is likewise possible for a further phosphorescent emitter which emits at a shorter wavelength than the actual emitter to be present as co-host in the mixture.

Preferred co-host materials are triarylamine derivatives, especially monoamines, lactams, carbazole derivatives and indenocarbazole derivatives.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum. In the context of the present invention, all luminescent compounds containing the abovementioned metals are regarded as phosphorescent compounds.

Examples of the above-described emitters can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094962, WO 2014/094961, WO 2014/094960, WO 2015/036074, WO 2015/104045, WO 2015/117718, WO 2016/015815, WO 2016/124304, WO 2017/032439 and the as yet unpublished application EP16179378.1. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In addition, it is possible to use the compounds of the invention in a hole blocker or electron transport layer. These may preferably also be substituted by one or more further electron-transporting groups, for example benzimidazole groups.

In the further layers of the organic electroluminescent device of the invention, it is possible to use any materials as typically used according to the prior art. The person skilled in the art is therefore able, without exercising inventive skill, to use any materials known for organic electroluminescent devices in combination with the inventive compounds of formula (1) or according to the preferred embodiments.

Additionally preferred is an organic electroluminescent device, characterized in that one or more layers are applied by a sublimation process. In this case, the materials are applied by vapour deposition in vacuum sublimation systems at an initial pressure of less than $10^{-5}$ mbar, preferably less than $10^{-6}$ mbar. It is also possible that the initial pressure is even lower or higher, for example less than $10^{-7}$ mbar.

Preference is likewise given to an organic electroluminescent device, characterized in that one or more layers are applied by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured.

Preference is additionally given to an organic electroluminescent device, characterized in that one or more layers are produced from solution, for example by spin-coating, or by any printing method, for example inkjet printing, LITI (light-induced thermal imaging, thermal transfer printing), screen printing, flexographic printing, offset printing or nozzle printing. For this purpose, soluble compounds are needed, which are obtained, for example, through suitable substitution.

In addition, hybrid methods are possible, in which, for example, one or more layers are applied from solution and one or more further layers are applied by vapour deposition. For example, it is possible to apply the emitting layer from solution and to apply the electron transport layer by vapour deposition.

These methods are known in general terms to those skilled in the art and can be applied by those skilled in the art without exercising inventive skill to organic electroluminescent devices comprising the compounds of the invention.

The compounds of the invention generally have very good properties on use in organic electroluminescent devices. Especially in the case of use of the compounds of the invention in organic electroluminescent devices, the lifetime is significantly better compared to similar compounds according to the prior art. At the same time, the further properties of the organic electroluminescent device, especially the efficiency and voltage, are likewise better or at least comparable. In addition, the compounds have a high glass transition temperature and high thermal stability.

The invention is now illustrated in detail by the examples which follow, without any intention of restricting it thereby.

EXAMPLES

Synthesis Examples

The syntheses which follow, unless stated otherwise, are conducted under a protective gas atmosphere in dried solvents. The compounds of the invention can be prepared by means of synthesis methods known to those skilled in the art.

a) Triazine Synthesis: 2,4-Bis(biphenyl-3-yl)-6-chloro[1,3,5]triazine

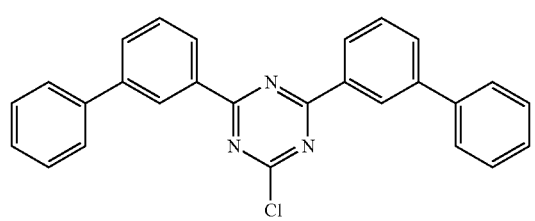 [SMILES: Clc1nc(-c2cccc(-c3ccccc3)c2)nc(-c2cccc(-c3ccccc3)c2)n1]

To an initial charge of 5.2 g of magnesium (0.215 mol) in a 500 ml four-neck flask is slowly added dropwise a solution of 50 g of 3-bromobiphenyl (214 mmol) in 200 ml of THF. The reaction mixture is heated to boiling for 1.5 h and then cooled down to room temperature. An initial charge of cyanuric chloride (17.2 g, 93 mmol) in 150 ml of THF in a second flask is cooled to 0° C. At this temperature, the cooled Grignard reagent is added dropwise and the mixture is stirred at RT for 12 h. After this time, 150 ml of HCl are added to the reaction mixture and the aqueous phase is extracted three times with dichloromethane. The combined organic phases are washed with water, dried over Na$_2$SO$_4$ and concentrated. The residue is recrystallized from EtOH. The yield is 32.8 g (78 mmol, 84%).

b) 2-Biphenyl-3-yl-4,6-dichloro[1,3,5]triazine

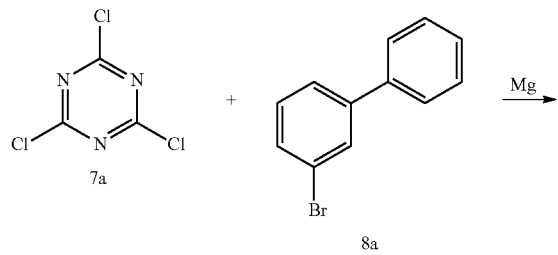

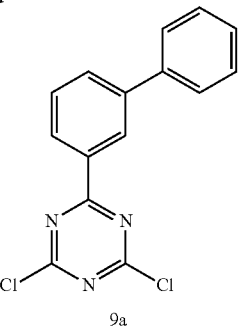

9a

To an initial charge of 7.9 g (330 mmol, 1.2 eq) of magnesium turnings in a 1 l four-neck flask is added a THF solution of 63 g (270 mmol, 1.0 eq) of 3-bromobiphenyl 8a (CAS 2113-57-7) at a sufficiently slow rate to maintain the reflux of the reaction mixture. After the addition has ended, the mixture is heated under reflux for a further 2 h.

In a 2 l four-neck flask, 50 g (270 mmol, 1 eq) of 2,4,6-trichloro-[1,3,5]triazine 7a (CAS 108-77-0) in 500 ml of THF are cooled down to −10° C. At this temperature, the Grignard solution is added dropwise at a sufficiently slow rate that the temperature does not exceed 0° C., and the mixture is finally stirred at room temperature overnight. For workup, 270 ml of 1 N hydrochloric acid are added dropwise and the mixture is stirred for 1 h. Subsequently, the aqueous phase is removed and extracted with diethyl ether. The combined organic phases are dried over sodium sulfate and the solvent is removed on a rotary evaporator. 56 g (69%) of a colourless oil 9a are obtained.

In an analogous manner, it is possible to obtain the following compounds:

| No. | Reactant 7 | Reactant 8 | Product 9 | Yield |
|---|---|---|---|---|
| 1b | Cl–N=N–Cl / N / Cl (triazine) | Br–C$_6$H$_4$–C$_6$H$_5$ (4-bromobiphenyl) 92-66-0 | biphenyl-triazine-Cl$_2$ | 56% |
| 2b | Cl–N=N–Cl / N / Cl (triazine) | 2-bromo-9,9-dimethylfluorene 28320-31-2 | 9,9-dimethylfluorenyl-triazine-Cl$_2$ | 27% |

| No. | Reactant 7 | Reactant 8 | Product 9 | Yield |
|---|---|---|---|---|
| 3b | | 28320-31-2 (use of 2 eq.) | | 48% |
| 4b | | 103068-20-8 | | 71% | c) 2-Biphenyl-3-yl-4-chloro-6-(9,9'-spirobi-9H-fluoren-2-yl)-[1,3,5]triazine

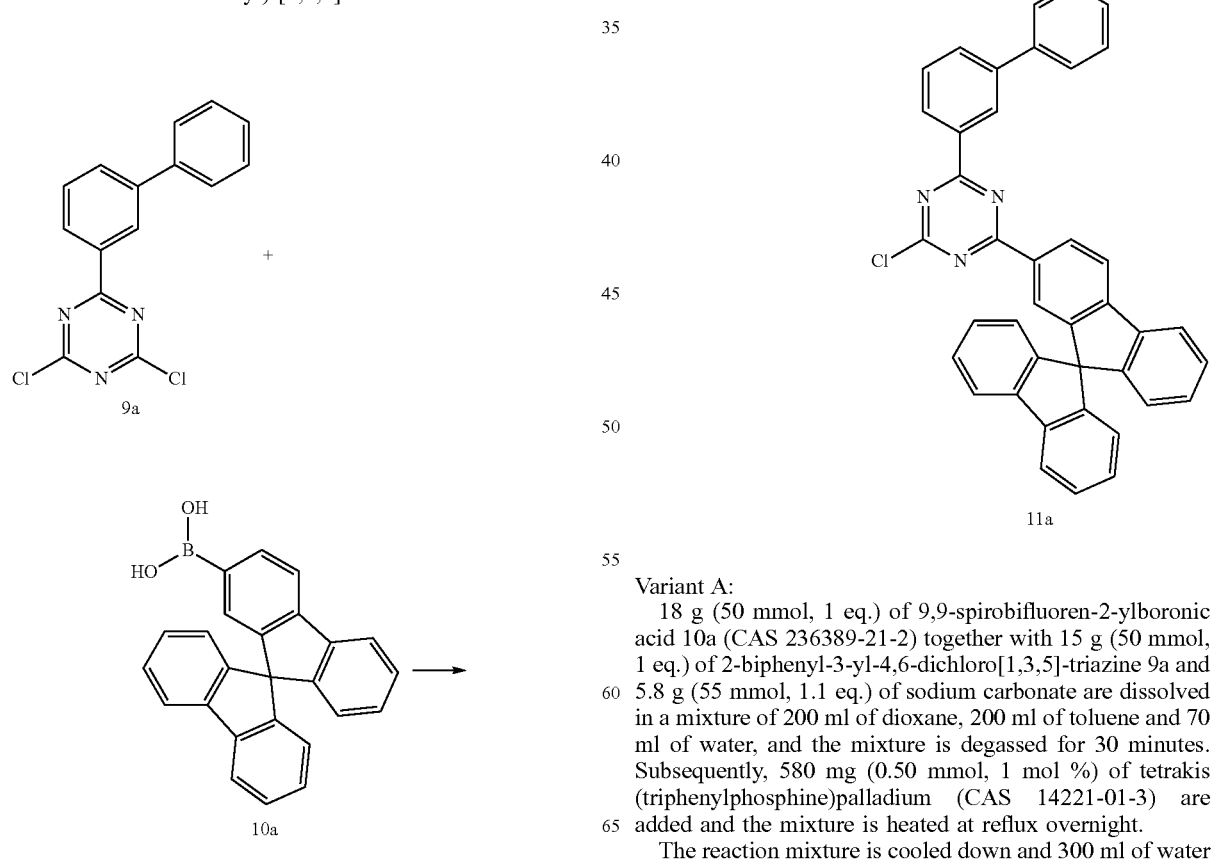

11a

Variant A:

18 g (50 mmol, 1 eq.) of 9,9-spirobifluoren-2-ylboronic acid 10a (CAS 236389-21-2) together with 15 g (50 mmol, 1 eq.) of 2-biphenyl-3-yl-4,6-dichloro[1,3,5]-triazine 9a and 5.8 g (55 mmol, 1.1 eq.) of sodium carbonate are dissolved in a mixture of 200 ml of dioxane, 200 ml of toluene and 70 ml of water, and the mixture is degassed for 30 minutes. Subsequently, 580 mg (0.50 mmol, 1 mol %) of tetrakis(triphenylphosphine)palladium (CAS 14221-01-3) are added and the mixture is heated at reflux overnight.

The reaction mixture is cooled down and 300 ml of water are added. The aqueous phase is extracted three times with ethyl acetate, the organic phases are combined and the solvent is removed on a rotary evaporator. After hot extraction with heptane/toluene 4:1, 15 g (26 mmol, 51%) of a colourless solid are obtained.

Variant B: Analogous to b)

In an analogous manner, it is possible to obtain the following compounds:

| No. | Variant | Reactant 9 | Reactant 10 | Product 11 | Yield |
|-----|---------|------------|-------------|------------|-------|
| 1c | B | | 2113-57-7 | | 68% |
| 2c | A | | 939430-30-5 | | 81% |
| 3c | A | | 100124-06-9 | | 63% |
| 4c | A | | 1421789-05-0 | | 71% |

-continued

| No. | Variant | Reactant 9 | Reactant 10 | Product 11 | Yield |
|---|---|---|---|---|---|
| 5c | A | | 1246022-50-3 | | 53% |
| 8c | A | | 854952-58-2 | | 68% |
| 9c | B | | 103068-20-8 | | 67% | d) 6-Bromo-2-fluoro-2'-methoxybiphenyl

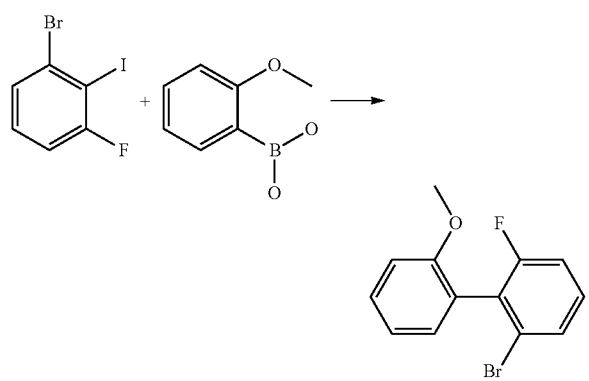

200 g (664 mmol) of 1-bromo-3-fluoro-2-iodobenzene and 101 g (664 mmol) of 2-methoxyphenylboronic acid and 137.5 g (997 mmol) of sodium tetraborate are dissolved in 1000 ml of THF and 600 ml of water, and degassed. 9.3 g (13.3 mmol) of bis(triphenylphosphine)palladium(II) chloride and 1 g (20 mmol) of hydrazinium hydroxide are added. The reaction mixture is then stirred under a protective gas atmosphere at 70° C. for 48 h. The cooled solution is supplemented with toluene, washed repeatedly with water, dried and concentrated. The product is purified via column chromatography on silica gel with toluene/heptane (1:2). Yield: 155 g (553 mmol), 83% of theory.

In an analogous manner, it is possible to obtain the following compounds:

| Reactant 1 | Reactant 2 | Product | Yield |
|---|---|---|---|
| d1 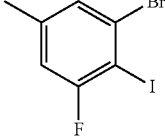 [1000576-09-9] | 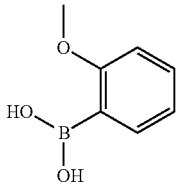 | 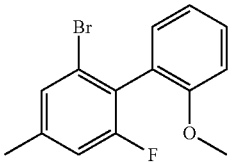 | 77% |
| d2 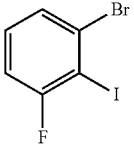 | 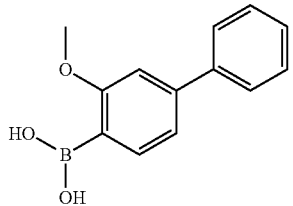 [1379680-54-2] | 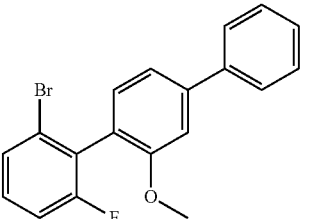 | 74% |
| d3 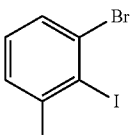 | 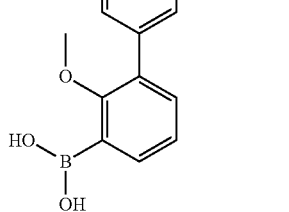 [1199350-14-5] | 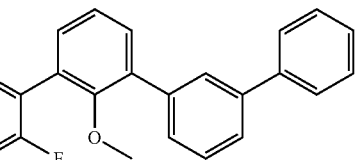 | 76% |
| d4 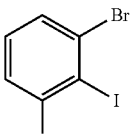 | 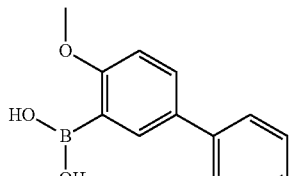 [1114496-44-4] | 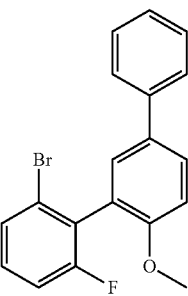 [SMILES: COc1ccc(-c2ccccc2)cc1-c1c(F)cccc1Br] | 71% | e) 6'-Bromo-2'-fluorobiphenyl-2-ol

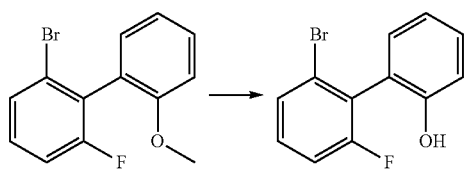 [SMILES: COc1ccccc1-c1c(F)cccc1Br ; Oc1ccccc1-c1c(F)cccc1Br]

112 g (418 mmol) of 6-bromo-2-fluoro-2'-methoxybiphenyl are dissolved in 2 l of dichloromethane and cooled to 5° C. 41.01 ml (431 mmol) of boron tribromide are added dropwise to this solution within 90 min, and stirring of the mixture continues overnight. Water is added gradually to the mixture, and the organic phase is washed three times with water, dried over $Na_2SO_4$, concentrated by rotary evaporation and purified by chromatography. Yield: 104 g (397 mmol), 98% of theory.

In an analogous manner, it is possible to obtain the following compounds:

| | Reactant 1 | Product | Yield |
|---|---|---|---|
| e1 | 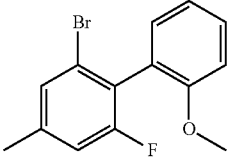 | 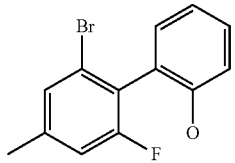 [SMILES: Cc1cc(F)c(-c2ccccc2O)c(Br)c1] | 92% |
| e2 | 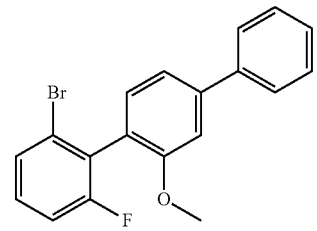 [SMILES: COc1cc(-c2ccccc2)ccc1-c1c(F)cccc1Br] | 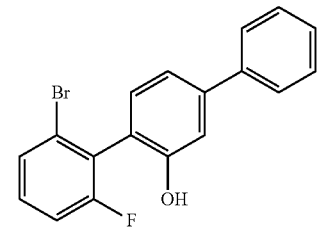 [SMILES: Oc1cc(-c2ccccc2)ccc1-c1c(F)cccc1Br] | 90% |
| e3 | 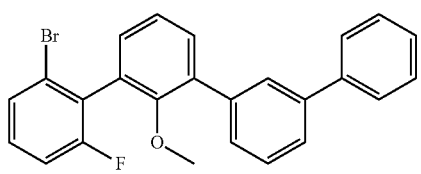 [SMILES: COc1c(-c2cccc(-c3ccccc3)c2)cccc1-c1c(F)cccc1Br] | 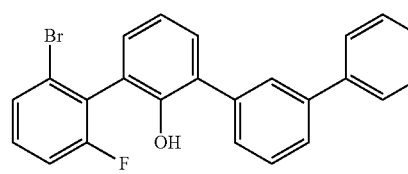 | 93% |
| e4 | 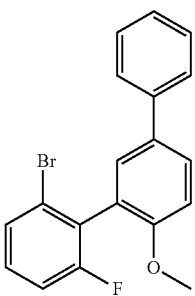 [SMILES: COc1ccc(-c2ccccc2)cc1-c1c(F)cccc1Br] | 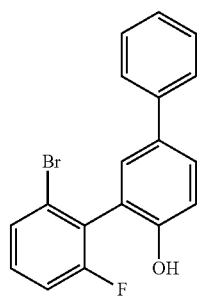 [SMILES: Oc1ccc(-c2ccccc2)cc1-c1c(F)cccc1Br] | 94% | f) 1-Bromodibenzofuran

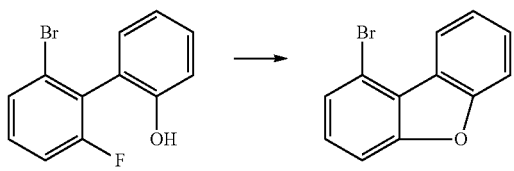 [SMILES: Oc1ccccc1-c1c(F)cccc1Br ; Brc1cccc2oc3ccccc3c12]

111 g (416 mmol) of 6'-bromo-2'-fluorobiphenyl-2-ol are dissolved in 2 l of DMF (max. 0.003% H$_2$O) SeccoSolv® and cooled to 5° C. 20 g (449 mmol) of sodium hydride (60% suspension in paraffin oil) are added to this solution in portions, once the addition has ended the mixture is stirred for 20 min, and then the mixture is heated to 100° C. for 45 min. After cooling, 500 ml of ethanol are added gradually to the mixture, which is concentrated completely by rotary evaporation and then purified by chromatography. Yield: 90 g (367 mmol), 88.5% of theory.

In an analogous manner, it is possible to obtain the following compounds:

| | Reactant 1 | Product | Yield |
|---|---|---|---|
| f1 | 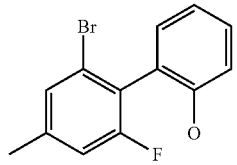 [SMILES: Cc1cc(F)c(-c2ccccc2O)c(Br)c1] | 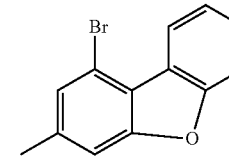 | 81% |

| | Reactant 1 | Product | Yield |
|---|---|---|---|
| f2 | | | 78% |
| f3 | | | 73% |
| f4 | | | 79% | g) Dibenzofuran-1-boronic acid

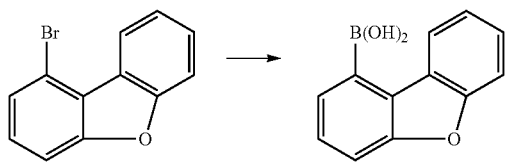 [SMILES: Brc1cccc2oc3ccccc3c12 ; OB(O)c1cccc2oc3ccccc3c12]

180 g (728 mmol) of 1-bromodibenzofuran are dissolved in 1500 ml of dry THF and cooled to −78° C. At this temperature, 305 ml (764 mmol/2.5 M in hexane) of n-butyllithium are added within about 5 min, and then the mixture is stirred at −78° C. for a further 2.5 h. At this temperature, 151 g (1456 mmol) of trimethyl borate are added very rapidly and the reaction is allowed to come gradually to RT (about 18 h). The reaction solution is washed with water and the precipitated solids and the organic phase are subjected to azeotropic drying with toluene. The crude product is extracted while stirring from toluene/methylene chloride at about 40° C. and filtered off with suction. Yield: 146 g (690 mmol), 95% of theory.

In an analogous manner, it is possible to obtain the following compounds:

| | Reactant 1 | Product | Yield |
|---|---|---|---|
| g1 | | | 81% |
| g2 | | | 78% |

| | Reactant 1 | Product | Yield |
|---|---|---|---|
| g3 | | | 73% |
| g4 | | | 79% |
| g5 | [65642-94-6] | | 73% | h) 2-Dibenzofuran-1-yl-4,6-diphenyl[1,3,5]triazine

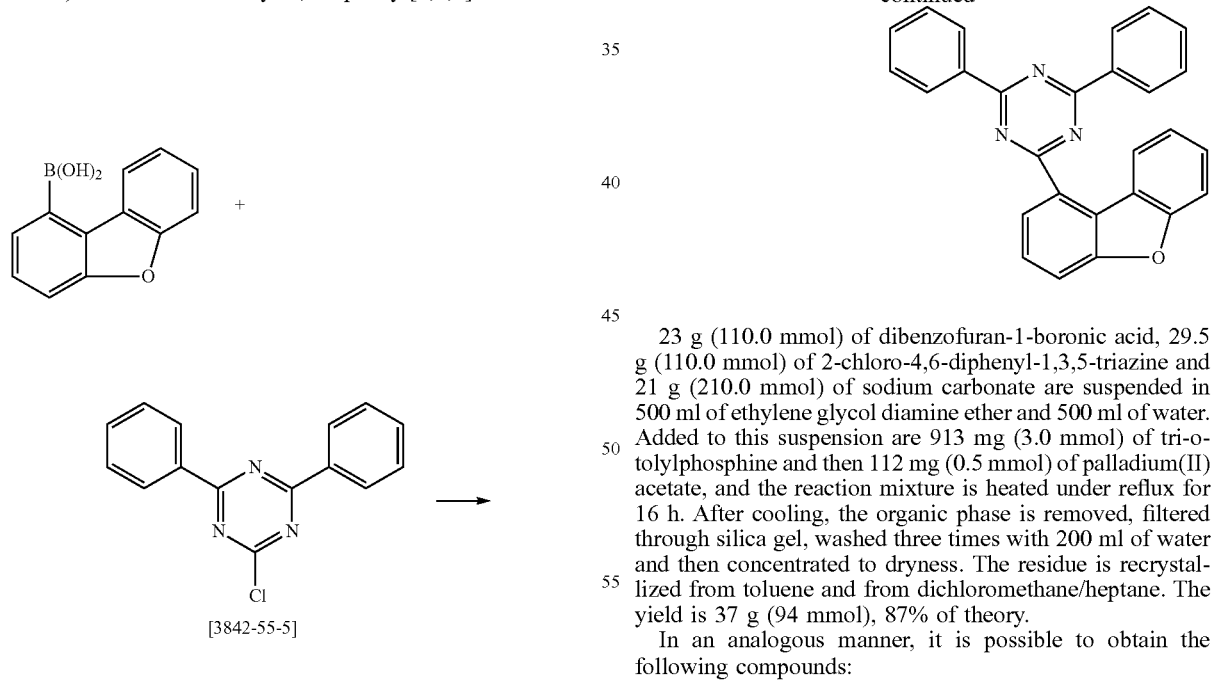

23 g (110.0 mmol) of dibenzofuran-1-boronic acid, 29.5 g (110.0 mmol) of 2-chloro-4,6-diphenyl-1,3,5-triazine and 21 g (210.0 mmol) of sodium carbonate are suspended in 500 ml of ethylene glycol diamine ether and 500 ml of water. Added to this suspension are 913 mg (3.0 mmol) of tri-o-tolylphosphine and then 112 mg (0.5 mmol) of palladium(II) acetate, and the reaction mixture is heated under reflux for 16 h. After cooling, the organic phase is removed, filtered through silica gel, washed three times with 200 ml of water and then concentrated to dryness. The residue is recrystallized from toluene and from dichloromethane/heptane. The yield is 37 g (94 mmol), 87% of theory.

In an analogous manner, it is possible to obtain the following compounds:

| | Reactant 1 | Reactant 2 | Product | Yield |
|---|---|---|---|---|
| h1 | 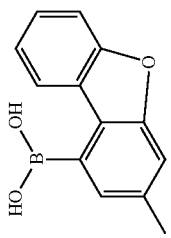 | 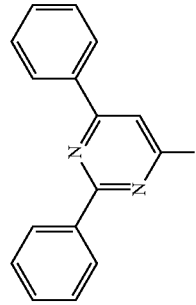  [40734-24-5] | 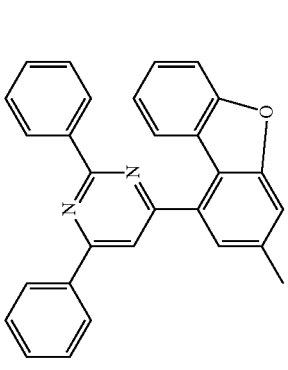 | 73% |
| h2 | 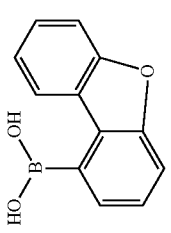 | 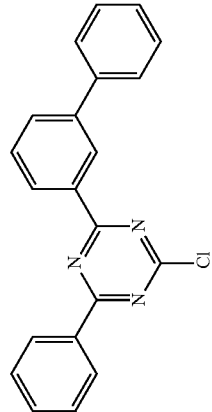 | 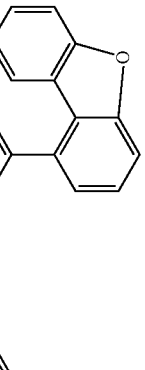 | 82% |
| h3 | 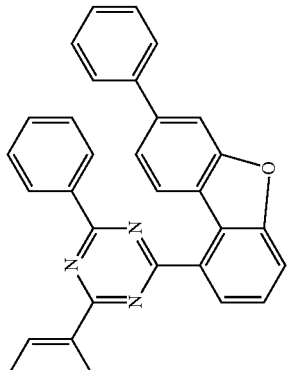 |   [3842-55-5] |  | 73% |

| Reactant 1 | Reactant 2 | Product | Yield |
|---|---|---|---|
| h4 | 40734-4-5 | | 72% |
| h5 | | | 65% |
| h6 | | | 63% |

-continued
| | Reactant 1 | Reactant 2 | Product | Yield |
|---|---|---|---|---|
| h14 | 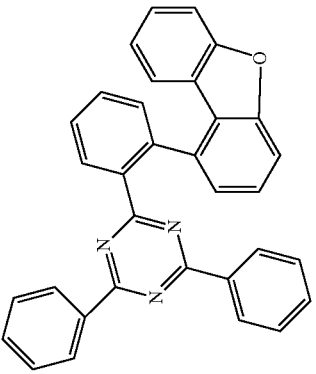 | 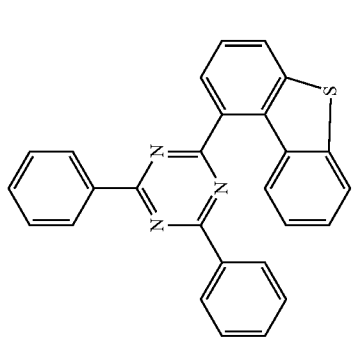 | 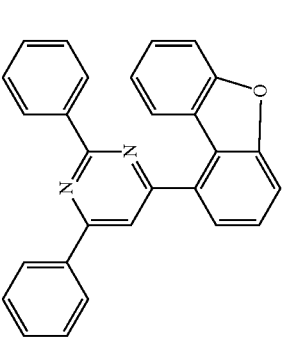 | 77% |
| h15 | 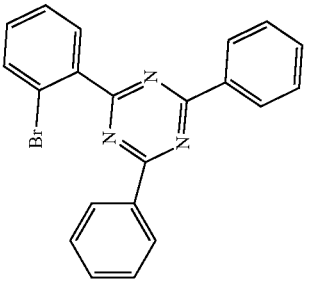 [1434286-69-7] | 77989-15-2 | 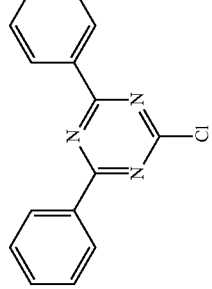 | 76% |
| h16 | 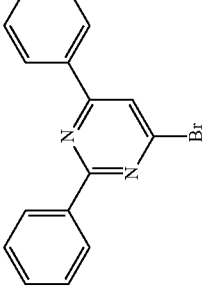 | 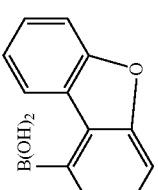 | 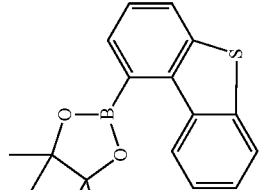 | 68% | i) 2-(8-Bromodibenzofuran-1-yl)-4,6-diphenyl[1,3,5]triazine

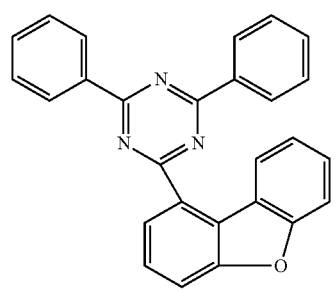 

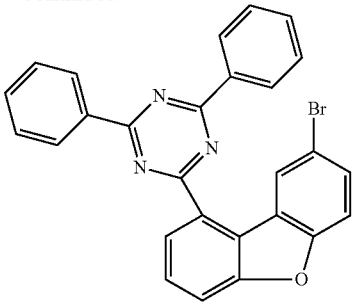

70 g (190.0 mmol) of 2-dibenzofuran-1-yl-4,6-diphenyl[1,3,5]triazine are suspended in 2000 ml of acetic acid (100%) and 2000 ml of sulfuric acid (95-98%). 34 g (190 mmol) of NBS are added to this suspension in portions and the mixture is stirred in the dark for 2 h. Thereafter, water/ice is added and the solids are removed and washed with ethanol. The residue is recrystallized from toluene. The yield is 80 g (167 mmol), 87% of theory.

In an analogous manner, it is possible to obtain the following compounds:

| | Reactant 1 | Product | Yield |
|---|---|---|---|
| i1 | 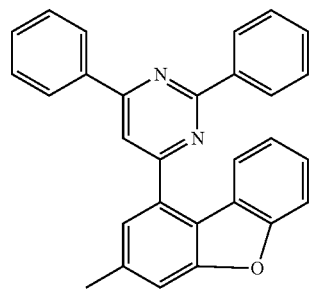 [SMILES: Cc1cc(-c2cc(-c3ccccc3)nc(-c3ccccc3)n2)c2c(c1)oc1ccccc12] | 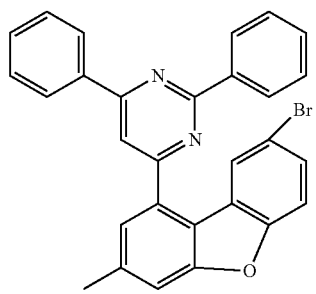 [SMILES: Cc1cc(-c2cc(-c3ccccc3)nc(-c3ccccc3)n2)c2c(c1)oc1ccc(Br)cc12] | 80% |
| i2 | 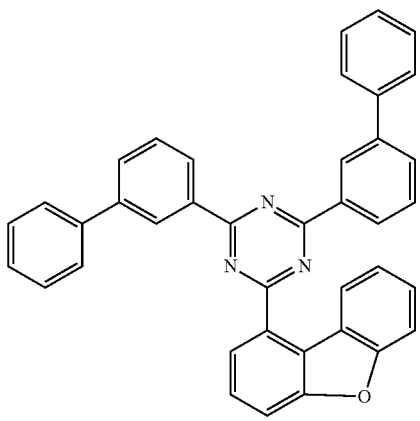 [SMILES: c1ccc(-c2cccc(-c3nc(-c4cccc(-c5ccccc5)c4)nc(-c4cccc5oc6ccccc6c45)n3)c2)cc1] | 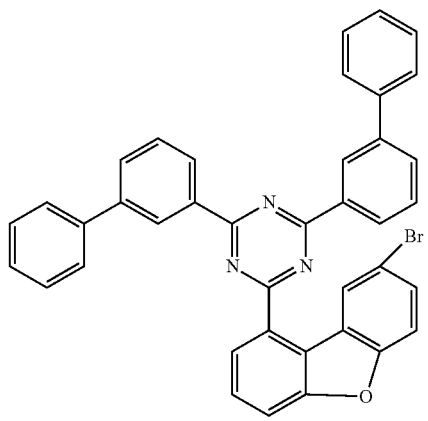 [SMILES: Brc1ccc2oc3cccc(-c4nc(-c5cccc(-c6ccccc6)c5)nc(-c5cccc(-c6ccccc6)c5)n4)c3c2c1] | 41% |

-continued
| | Reactant 1 | Product | Yield |
|---|---|---|---|
| i3 | 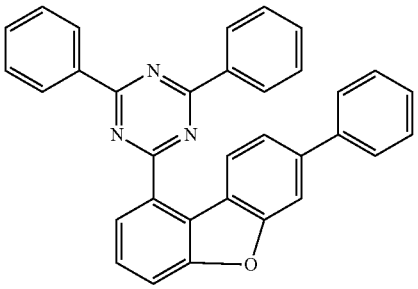 [SMILES: c1ccc(-c2ccc3c(c2)oc2cccc(-c4nc(-c5ccccc5)nc(-c5ccccc5)n4)c23)cc1] | 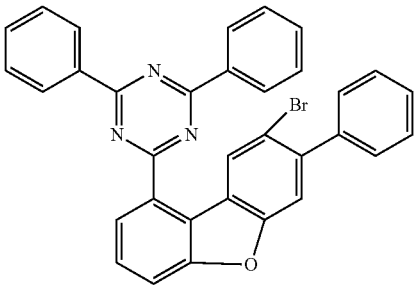 [SMILES: Brc1cc2c(cc1-c1ccccc1)oc1cccc(-c3nc(-c4ccccc4)nc(-c4ccccc4)n3)c12] | 52% |
| i4 | 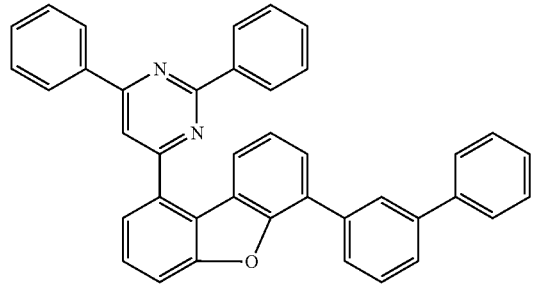 [SMILES: c1ccc(-c2cccc(-c3cccc4c3oc3cccc(-c5cc(-c6ccccc6)nc(-c6ccccc6)n5)c34)c2)cc1] | 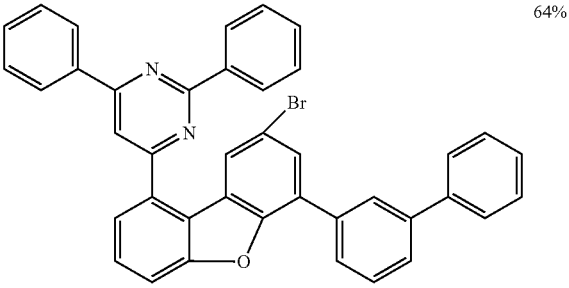 | 64% |
| i5 | 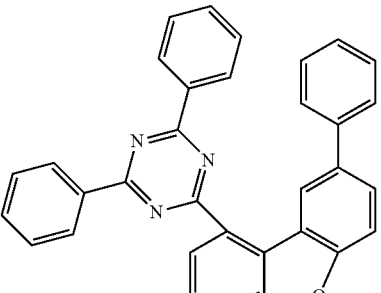 | 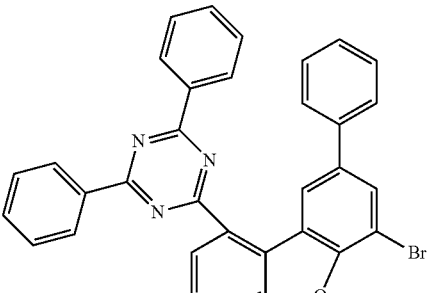 | 33% |
| i6 | 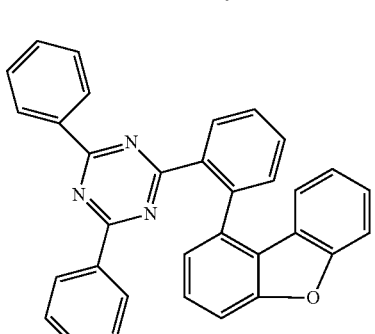 | 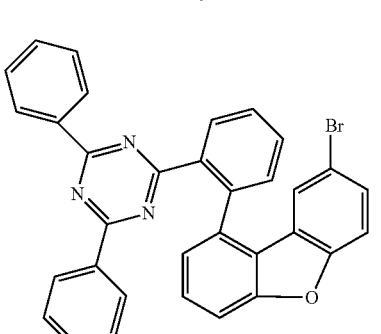 | 41% |
| i7 | 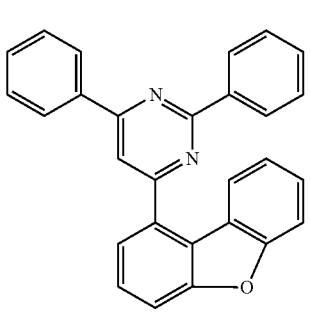 [SMILES: c1ccc(-c2cc(-c3cccc4oc5ccccc5c34)nc(-c3ccccc3)n2)cc1] | 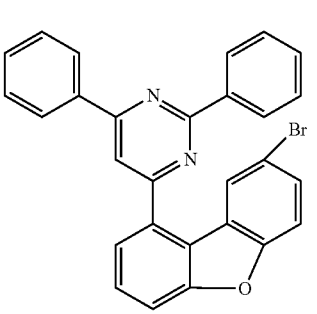 | 58% |

In the case of thiophene derivatives, nitrobenzene is used rather than sulfuric acid and elemental bromine in place of NBS:

| i8 | | 55% |
|---|---|---|

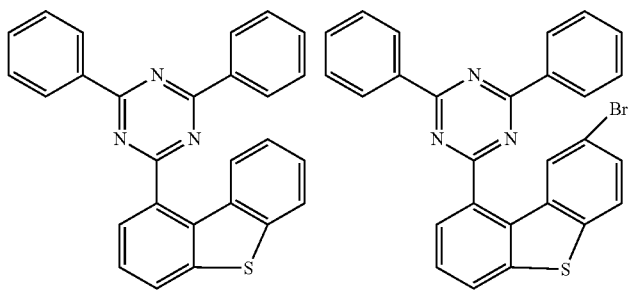

k) 2,4-Diphenyl-6-[8-(4,4,5,5-tetramethyl[1,3,2]dioxaborolan-2-yl)-dibenzofuran-1-yl][1,3,5]triazine

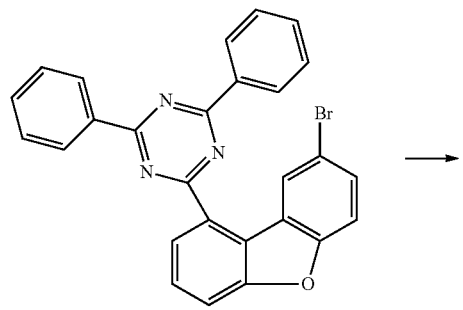 → 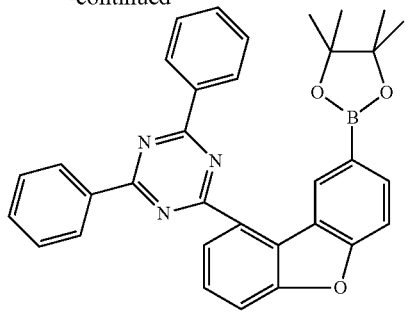

In a 500 ml flask, under protective gas, 13.3 g (28 mmol) of 2-(8-bromodibenzofuran-1-yl)-4,6-diphenyl[1,3,5]triazine and 8.5 g (34 mmol, 1.2 eq) of bis(pinacolato)diborane (CAS 73183-34-3) are dissolved in 120 ml of dry DMF and the mixture is degassed for 30 minutes. Subsequently, 8.2 g (84 mmol, 3.0 eq.) of potassium acetate and 690 mg (0.84 mmol, 3 mol %) of [1,1'-bis(diphenylphosphino)ferrocene]dichloropalladium(II) complex with dichloromethane (CAS 95464-05-4) are added, and the mixture is heated to 90° C. overnight. After the reaction has ended, the mixture is diluted with 300 ml of toluene and extracted with water. The residue is recrystallized from heptane. The yield is 15 g (24 mmol), 88% of theory.

In an analogous manner, it is possible to obtain the following compounds:

| | Reactant 1 | Product | Yield |
|---|---|---|---|
| k1 | | | 80% |

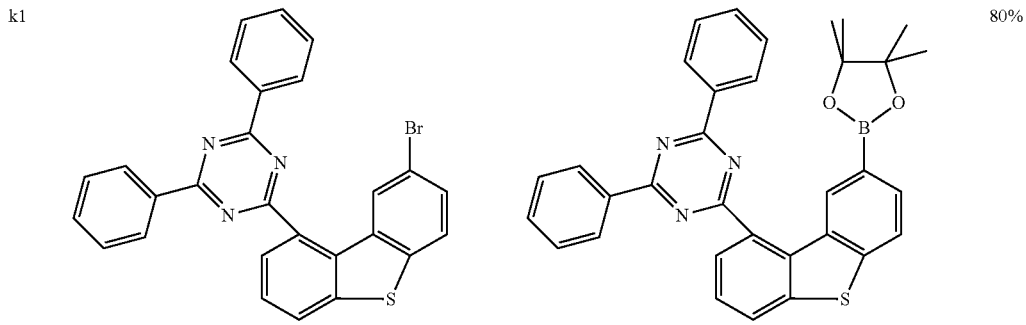

-continued

| Reactant 1 | Product | Yield |
|---|---|---|
| k2 | | 64% |
| k3 | | 63% |
| k4 | | 67% |
| k5 [1416903-68-8] | | 65% |

-continued

| Reactant 1 | Product | Yield |
|---|---|---|
| k6 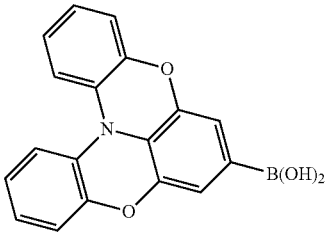 [SMILES: OB(O)c1cc2c3c(c1)Oc1ccccc1N3c1ccccc1O2] [1333316-19-0] | 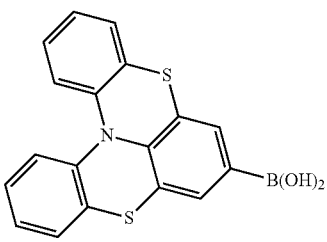 [SMILES: OB(O)c1cc2c3c(c1)Sc1ccccc1N3c1ccccc1S2] | 67% |
| k7 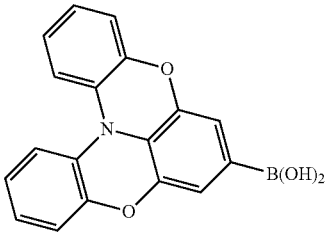 [SMILES: OB(O)c1cc2c3c(c1)Oc1ccccc1N3c1ccccc1O2] [1333316-19-0] | | 60% | l) 2-[8-(4-Chlorophenyl)dibenzothiophen-1-yl]-4,6-diphenyl[1,3,5]triazine

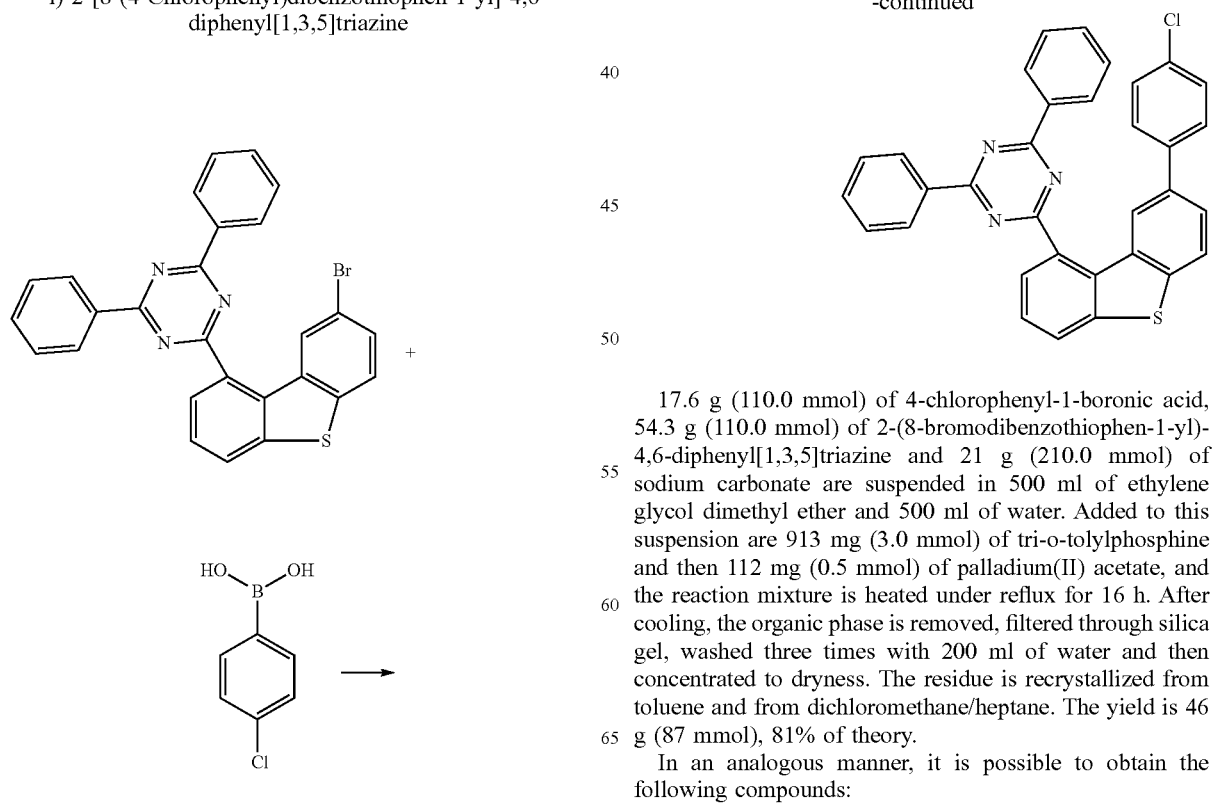

17.6 g (110.0 mmol) of 4-chlorophenyl-1-boronic acid, 54.3 g (110.0 mmol) of 2-(8-bromodibenzothiophen-1-yl)-4,6-diphenyl[1,3,5]triazine and 21 g (210.0 mmol) of sodium carbonate are suspended in 500 ml of ethylene glycol dimethyl ether and 500 ml of water. Added to this suspension are 913 mg (3.0 mmol) of tri-o-tolylphosphine and then 112 mg (0.5 mmol) of palladium(II) acetate, and the reaction mixture is heated under reflux for 16 h. After cooling, the organic phase is removed, filtered through silica gel, washed three times with 200 ml of water and then concentrated to dryness. The residue is recrystallized from toluene and from dichloromethane/heptane. The yield is 46 g (87 mmol), 81% of theory.

In an analogous manner, it is possible to obtain the following compounds:

| Reactant 1 | Reactant 2 | Product | Yield |
|---|---|---|---|
| 11 | | | 73% |
| 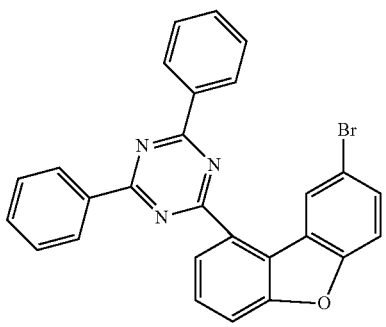 [SMILES: Brc1ccc2oc3cccc(-c4nc(-c5ccccc5)nc(-c5ccccc5)n4)c3c2c1] | 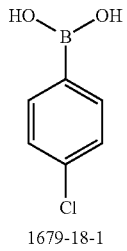
1679-18-1 | | |
| 21 | | | 82% |
| 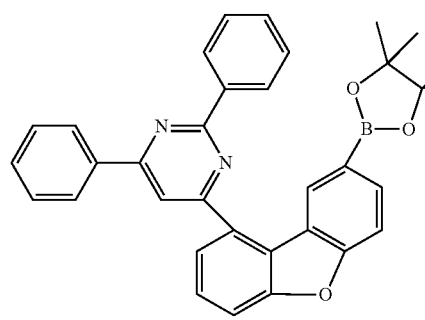 | 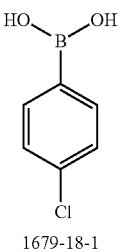
1679-18-1 | | | m)
Biphenyl-4-yl(9,9-dimethyl-9H-fluoren-2-yl)amine

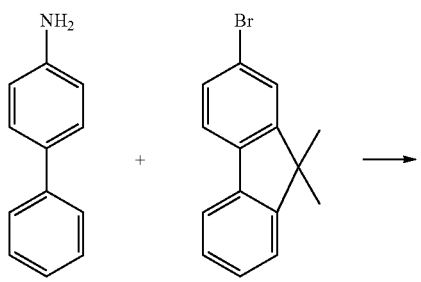

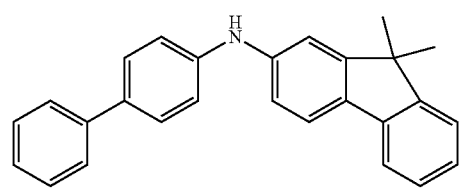

24.0 g (142 mmol, 1.2 eq.) of 4-aminobiphenyl (CAS 92-67-1) and 32.0 g (117 mmol, 1.0 eq.) of 2-bromo-9,9'-dimethylfluorene (CAS 28320-31-2) are initially charged in 950 ml of toluene and saturated with argon for 30 minutes. Subsequently, 1.0 g (1.8 mmol, 0.02 eq.) of 1,1'-bis(diphenylphosphino)ferrocene (CAS 12150-46-8), 350 mg (1.6 mmol, 0.01 eq.) of palladium(II) acetate (CAS 3375-31-3) and 29 g (300 mmol, 2.6 eq.) of sodium tert-butoxide (CAS 865-48-5) are added and the mixture is heated under reflux overnight. After the reaction has ended, the mixture is diluted with 300 ml of toluene and extracted with water. The organic phase is dried over sodium sulfate and the solvent is removed on a rotary evaporator. 50 ml of ethyl acetate are added to the brown oil, which is added to a mixture of heptane/ethyl acetate 20:1. The solids formed are filtered off with suction and washed with heptane. The yield is 29 g (80 mmol), 69% of theory.

In an analogous manner, it is possible to obtain the following compounds:

| | Reactant 1 | Reactant 2 | Product | Yield |
|---|---|---|---|---|
| 1m | 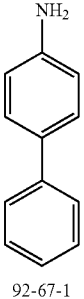 [SMILES: Nc1ccc(-c2ccccc2)cc1]<br>92-67-1 | 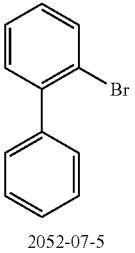 [SMILES: Brc1ccccc1-c1ccccc1]<br>2052-07-5 | 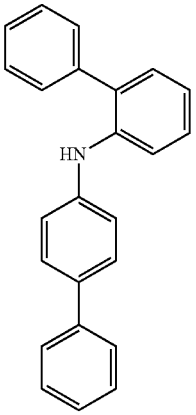 [SMILES: c1ccc(-c2ccc(Nc3ccccc3-c3ccccc3)cc2)cc1] | 71% |
| 2m | <br>92-67-1 | 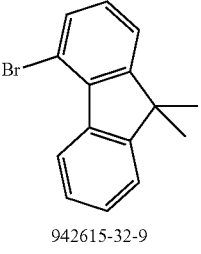 [SMILES: CC1(C)c2ccccc2-c2c(Br)cccc21]<br>942615-32-9 | 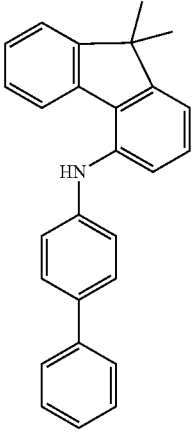 [SMILES: CC1(C)c2ccccc2-c2c(Nc3ccc(-c4ccccc4)cc3)cccc21] | 61% |
| 3m | 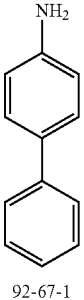 [SMILES: Nc1ccc(-c2ccccc2)cc1]<br>92-67-1 | 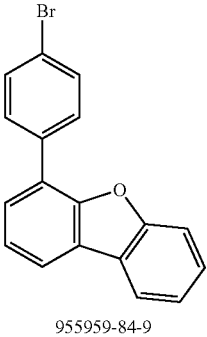 [SMILES: Brc1ccc(-c2cccc3c2oc2ccccc23)cc1]<br>955959-84-9 | 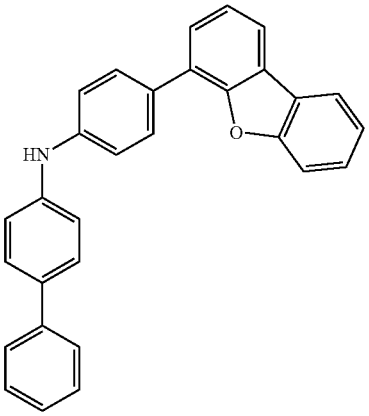 [SMILES: c1ccc(-c2ccc(Nc3ccc(-c4cccc5c4oc4ccccc45)cc3)cc2)cc1] | 78% |
| 4m | 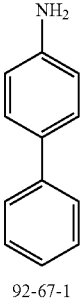 [SMILES: Nc1ccc(-c2ccccc2)cc1]<br>92-67-1 | 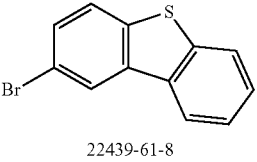 [SMILES: Brc1ccc2sc3ccccc3c2c1]<br>22439-61-8 | 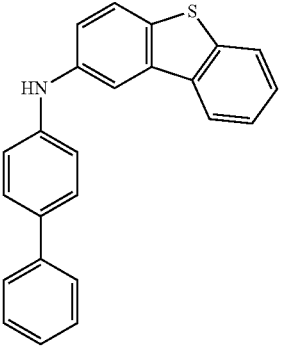 [SMILES: c1ccc(-c2ccc(Nc3ccc4sc5ccccc5c4c3)cc2)cc1] | 82% |

-continued
| Reactant 1 | Reactant 2 | Product | Yield |
|---|---|---|---|
| 5m 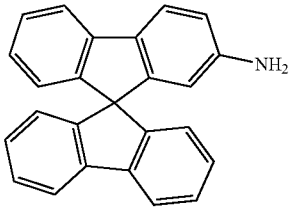 118951-68-1 | 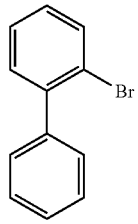 2052-07-5 | 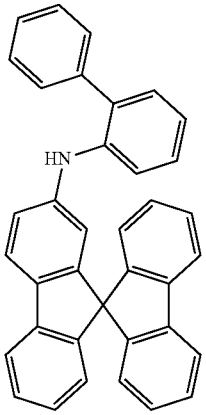 [SMILES: c1ccc(-c2ccccc2Nc2ccc3c(c2)C2(c4ccccc4-c4ccccc42)c2ccccc2-3)cc1] | 62% |
| 6m 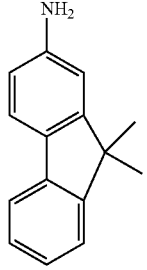 108714-73-4 | 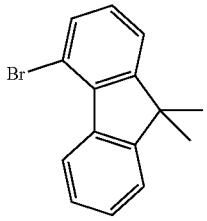 942615-32-9 | 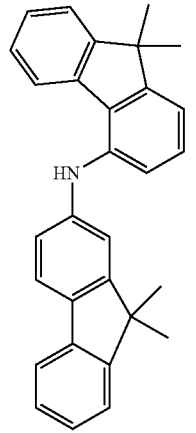 [SMILES: CC1(C)c2ccccc2-c2ccc(Nc3cccc4c3-c3ccccc3C4(C)C)cc21] | 47% |
| 7m 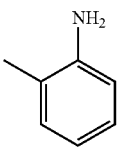 | 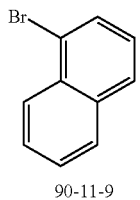 90-11-9 | 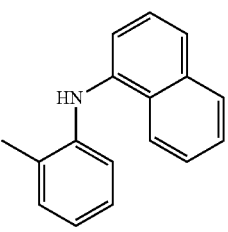 [SMILES: Cc1ccccc1Nc1cccc2ccccc12] | 92% |

-continued
| Reactant 1 | Reactant 2 | Product | Yield |
|---|---|---|---|
| 8m | | | 75% |
| 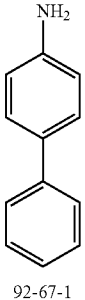 [SMILES: Nc1ccc(-c2ccccc2)cc1] 92-67-1 | 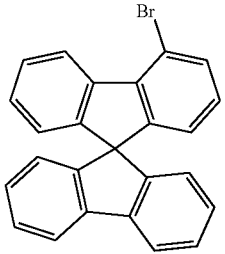 171408-76-7 | 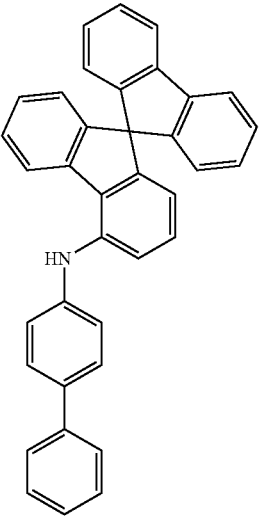 [SMILES: c1ccc(-c2ccc(Nc3cccc4c3-c3ccccc3C43c4ccccc4-c4ccccc43)cc2)cc1] | |
| 9m | | | 84% |
| 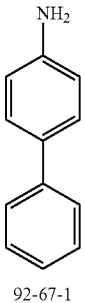 [SMILES: Nc1ccc(-c2ccccc2)cc1] 92-67-1 | 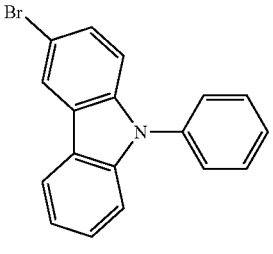 1153-85-1 | 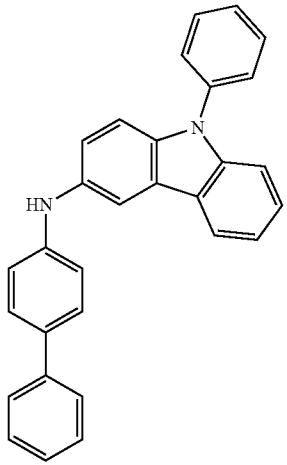 [SMILES: c1ccc(-c2ccc(Nc3ccc4c(c3)c3ccccc3n4-c3ccccc3)cc2)cc1] | |
| 10m | | | 62% |
| 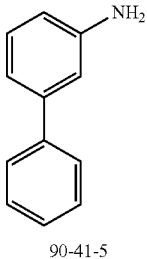 90-41-5 | 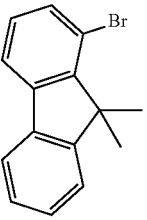 1225053-54-2 | 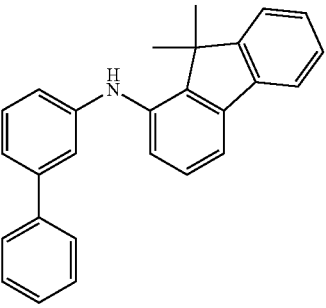 [SMILES: CC1(C)c2ccccc2-c2cccc(Nc3cccc(-c4ccccc4)c3)c21] | |

-continued
| | Reactant 1 | Reactant 2 | Product | Yield |
|---|---|---|---|---|
| 11m | 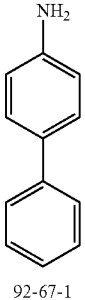 [SMILES: Nc1ccc(-c2ccccc2)cc1]<br>92-67-1 | 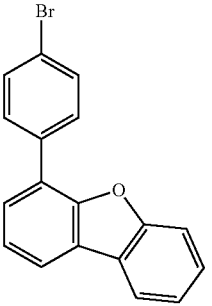<br>1028647-93-9 | 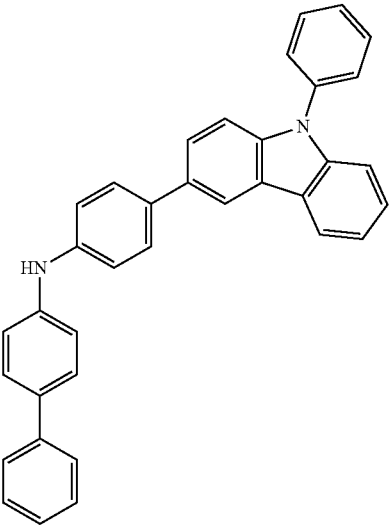 [SMILES: c1ccc(-c2ccc(Nc3ccc(-c4ccc5c(c4)c4ccccc4n5-c4ccccc4)cc3)cc2)cc1] | 78% |
| 12m | 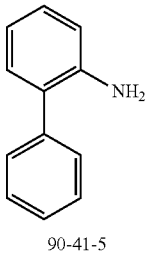 [SMILES: Nc1ccccc1-c1ccccc1]<br>90-41-5 | 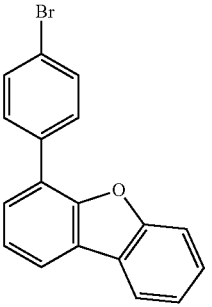<br>955959-84-9 | 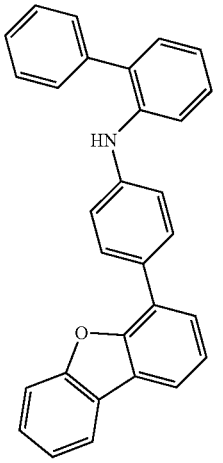 [SMILES: c1ccc(-c2ccccc2Nc2ccc(-c3cccc4c3oc3ccccc34)cc2)cc1] | 62% |
n) Biphenyl-4-yl-(9,9-dimethyl-9H-fluoren-2-yl)-{4-[9-(4,6-diphenyl-[1,3,5]triazin-2-yl)dibenzofuran-2-yl]phenyl}amine
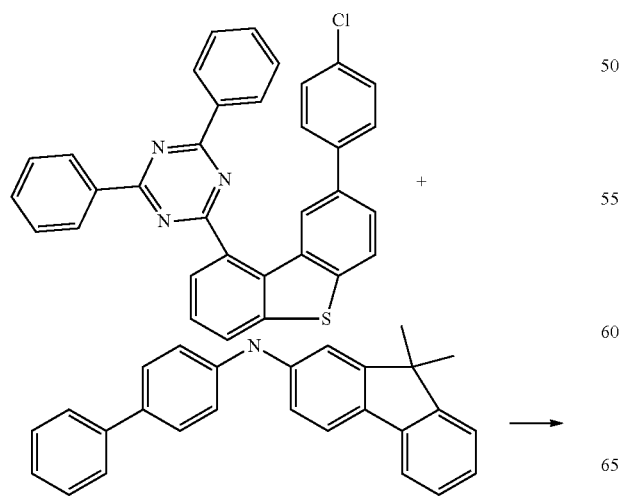

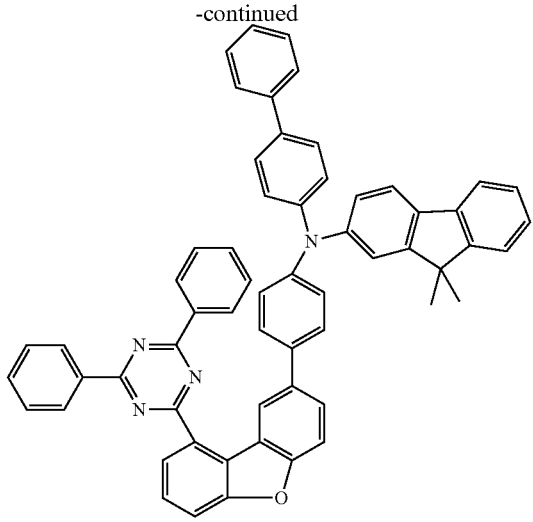

27.8 g (80 mmol, 1.0 eq.) of biphenyl-4-yl(9,9-dimethyl-9H-fluoren-2-yl)amine and 42 g (80 mmol, 1.0 eq.) of 2-[8-(4-chlorophenyl)dibenzofuran-1-yl]-4,6-diphenyl[1,3,5]triazine are dissolved in 600 ml of toluene and degassed for 30 minutes. Subsequently, 45 g (240 mmol, 3.0 eq.) of sodium tert-butoxide, 890 mg (0.40 mmol, 0.050 eq.) of palladium(II) acetate and 8 ml (8.0 mmol, 0.10 eq.) of a 1M tri-tert-butylphosphine solution are added. The mixture is heated under reflux overnight and, after the reaction has ended, filtered twice through alumina with toluene. After the solvent has been removed on a rotary evaporator, the oil is dissolved in a little THF and introduced into heptane. The residue is recrystallized from toluene and from heptane/toluene 1:1 and finally sublimed under high vacuum ($p=5\times 10^{-5}$ mbar, T=350° C.). The yield is 50 g (59 mmol), 75% of theory.

In an analogous manner, it is possible to obtain the following compounds:

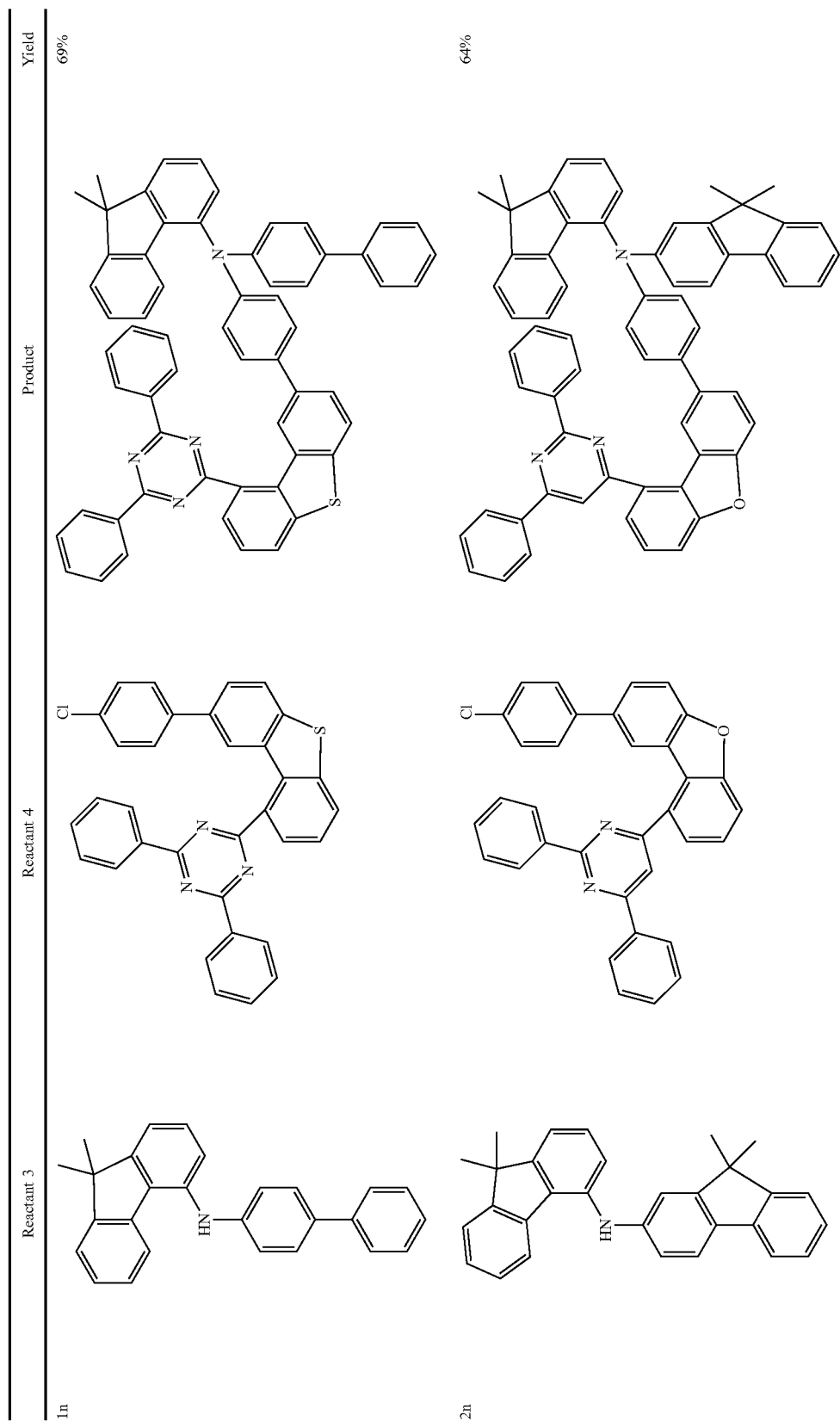

-continued

| | Reactant 3 | Reactant 4 | Product | Yield |
|---|---|---|---|---|
| 3n | | | | 59% |
| 4n | | | | 61% |

-continued
| | Reactant 3 | Reactant 4 | Product | Yield |
|---|---|---|---|---|
| 5n | 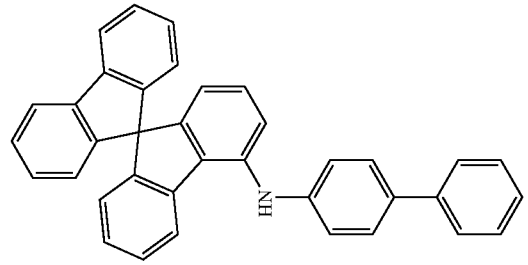 | 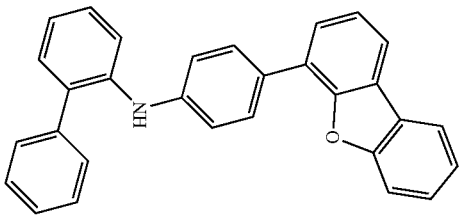 | 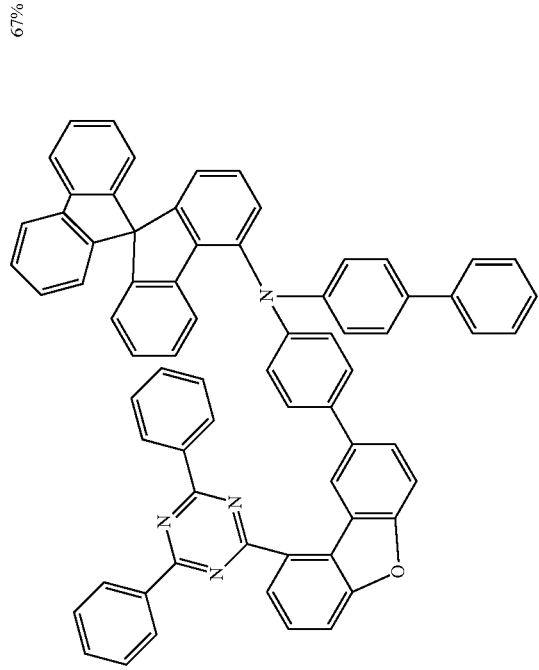 | 67% |
| 6n | 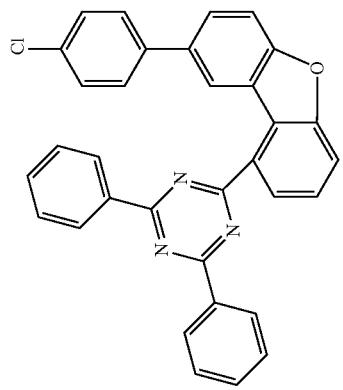 | 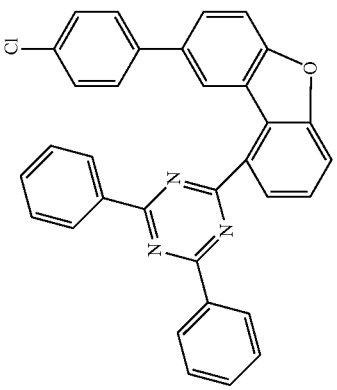 | 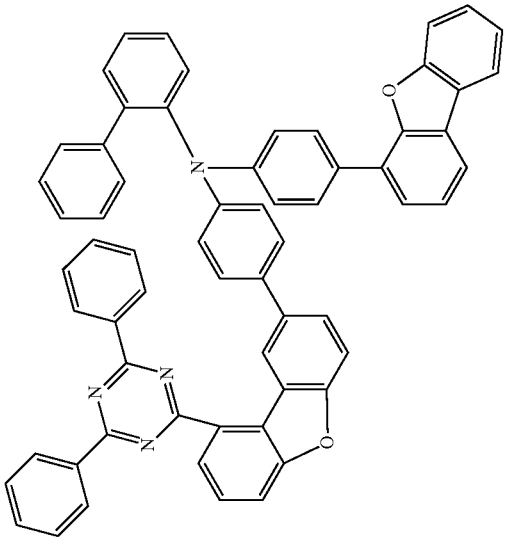 | 60% |

| | Reactant 3 | Reactant 4 | Product | Yield |
|---|---|---|---|---|
| 7n | | | | 72% |

In an analogous manner, it is possible to obtain the following compounds:
| | Reactant 3 | Reactant 4 | Product | Yield |
|---|---|---|---|---|
| 8n | 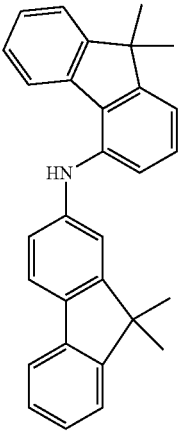 [SMILES: CC1(C)c2ccccc2-c2ccc(Nc3cccc4c3-c3ccccc3C4(C)C)cc21] | 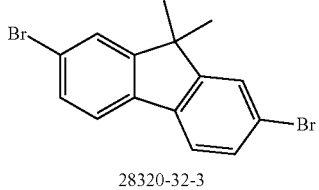 [SMILES: CC1(C)c2cc(Br)ccc2-c2ccc(Br)cc21]  28320-32-3 | 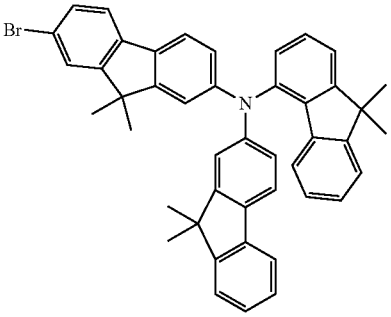 [SMILES: CC1(C)c2ccccc2-c2ccc(N(c3ccc4c(c3)C(C)(C)c3cc(Br)ccc3-4)c3cccc4c3-c3ccccc3C4(C)C)cc21] | 51% |
| 9n | 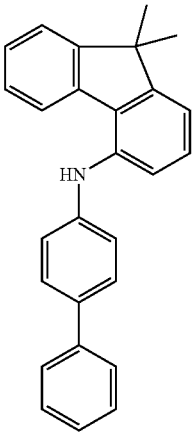 [SMILES: CC1(C)c2ccccc2-c2c(Nc3ccc(-c4ccccc4)cc3)cccc21] | 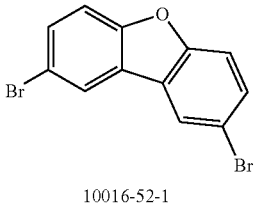 [SMILES: Brc1ccc2oc3ccc(Br)cc3c2c1]  10016-52-1 | 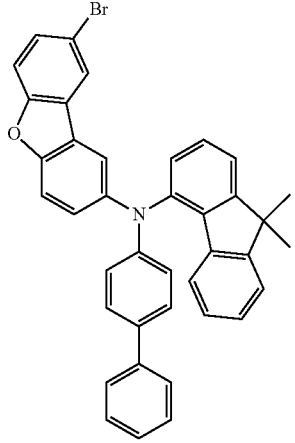 [SMILES: CC1(C)c2ccccc2-c2c(N(c3ccc(-c4ccccc4)cc3)c3ccc4oc5ccc(Br)cc5c4c3)cccc21] | 37% |
| 10n | 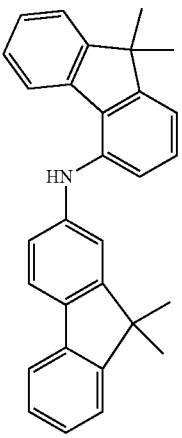 [SMILES: CC1(C)c2ccccc2-c2ccc(Nc3cccc4c3-c3ccccc3C4(C)C)cc21] | 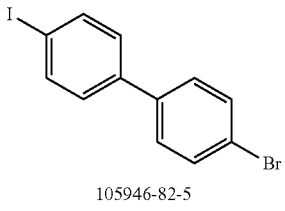 [SMILES: Brc1ccc(-c2ccc(I)cc2)cc1]  105946-82-5 | 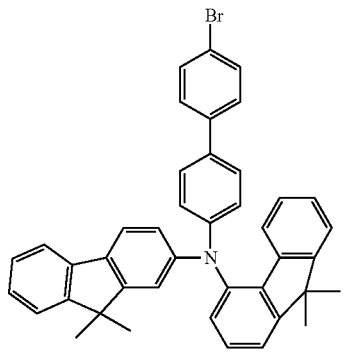 [SMILES: CC1(C)c2ccccc2-c2ccc(N(c3ccc(-c4ccc(Br)cc4)cc3)c3cccc4c3-c3ccccc3C4(C)C)cc21] | 80% |

-continued

| | Reactant 3 | Reactant 4 | Product | Yield |
|---|---|---|---|---|
| 11n | | 201138-91-2 | | 36% |
| 12n | | | | 48% |
| 13n | | | | 50% |
| 14n | | | | 47% | o) (9,9-Dimethyl-9H-fluoren-4-yl)-(9,9-dimethyl-9H-fluoren-2-yl){7-[9-(4,6-diphenyl[1,3,5]triazin-2-yl)dibenzofuran-2-yl]-9,9-dimethyl-9H-fluoren-2-yl}amine

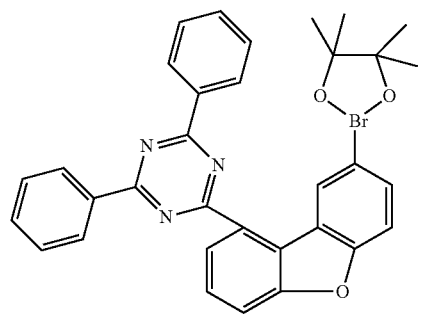

+

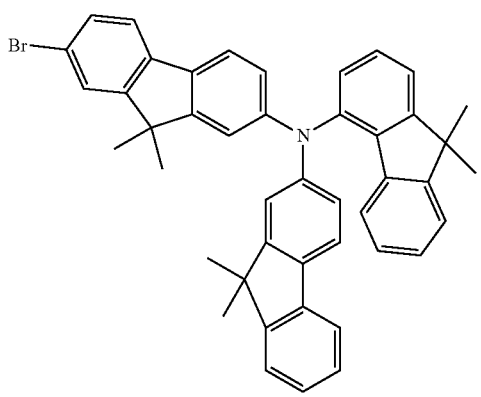

→

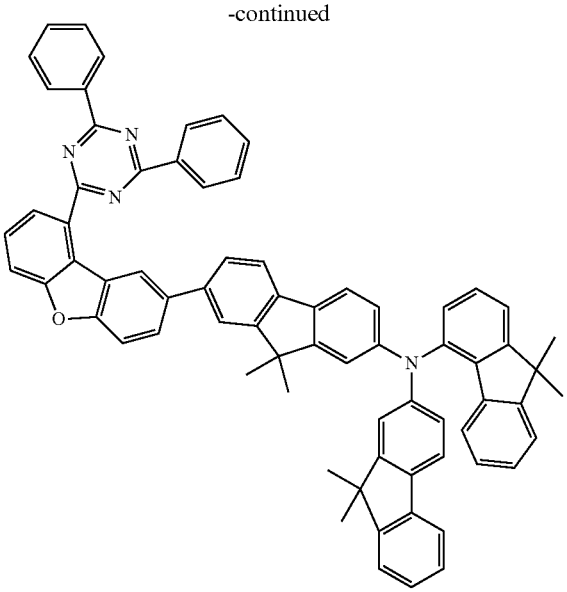

84 g (125 mmol, 1.0 eq.) of (7-bromo-9,9-dimethyl-9H-fluoren-2-yl)-(9,9-dimethyl-9H-fluoren-4-yl)-(9,9-dimethyl-9H-fluoren-2-yl)amine and 72 g (125 mmol, 1.0 eq) of 2,4-diphenyl-6-[8-(4,4,5,5-tetramethyl-[1,3,2]dioxaborolan-2-yl)dibenzofuran-1-yl][1,3,5]triazine are initially charged in a mixture of 400 ml of water, 400 ml of dioxane and 400 ml of toluene, and degassed for 30 minutes. After addition of 280 mg (1.25 mmol, 1 mol %) of palladium(II) acetate and 1.14 g (3.75 mmol, 3 mol %) of tri-o-tolylphoshine, the mixture is heated under reflux overnight and, after the reaction has ended, a little water is added. The organic phase is removed and extracted twice with water. After the organic phase is dried over sodium sulfate, the residue is recrystallized from heptane/toluene. The residue is recrystallized from toluene and from heptane/toluene 1:1 and finally sublimed under high vacuum (p=5×10⁻⁵ mbar, T=350° C.). 96 g (96 mmol, 80%) of a beige solid are obtained.

In an analogous manner, it is possible to obtain the following compounds:

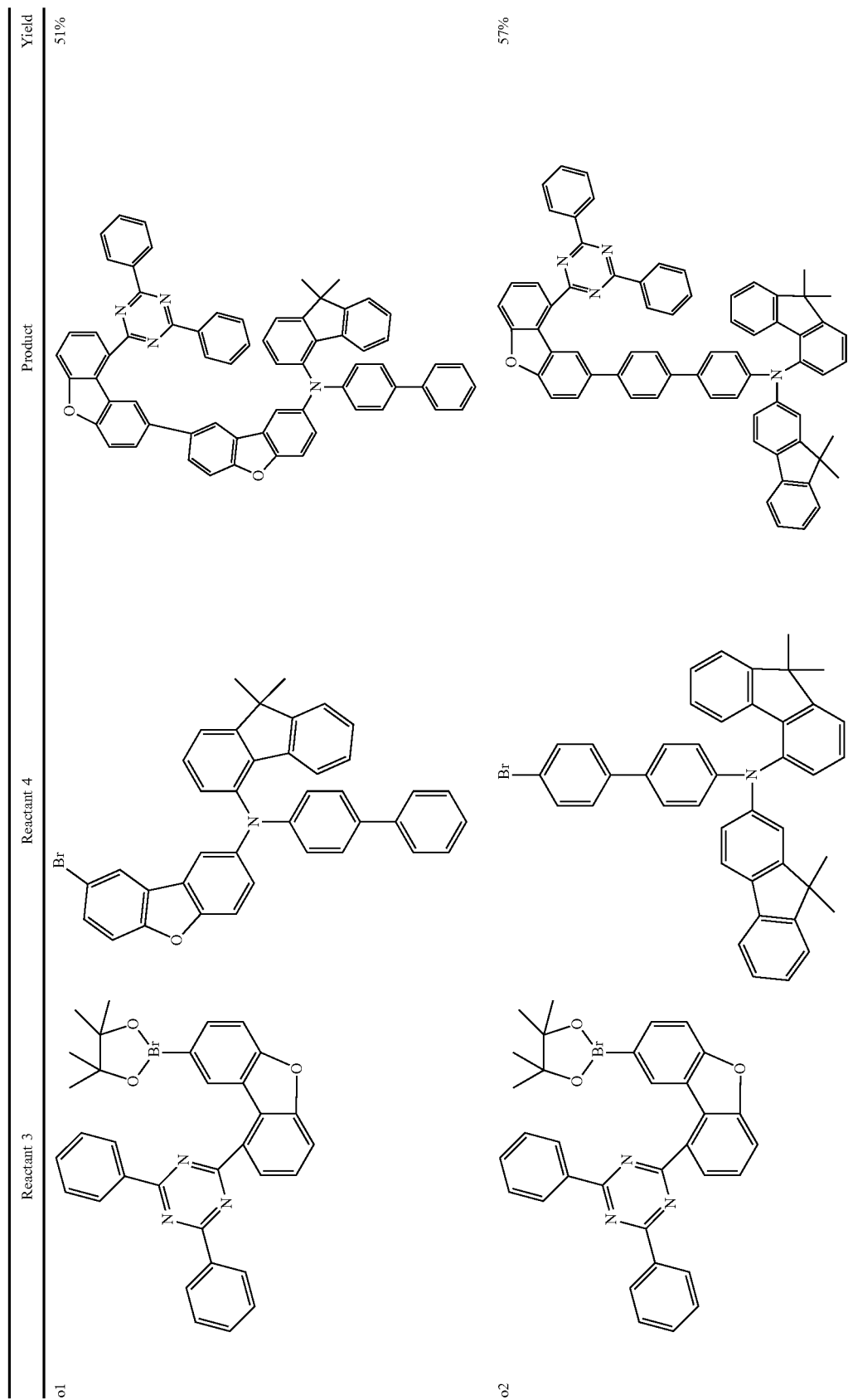

-continued

| | Reactant 3 | Reactant 4 | Product | Yield |
|---|---|---|---|---|
| o3 | | | | 56% |
| o4 | | | | 61% |

-continued

| | Reactant 3 | Reactant 4 | Product | Yield |
|---|---|---|---|---|
| o5 | | | | 63% |
| o6 | | | | 57% |

| | Reactant 3 | Reactant 4 | Product | Yield |
|---|---|---|---|---|
| o7 | | | | 62% |
| o8 | | | | 63% |

| | Reactant 3 | Reactant 4 | Product | Yield |
|---|---|---|---|---|
| o9 | | | | 64% |
| o10 | | | | 60% |

Production of the OLEDs

Examples I1 to I12 which follow (see Table 1) present the use of the materials of the invention in OLEDs.

Pretreatment for Examples I1-I12: Glass plaques coated with structured ITO (indium tin oxide) of thickness 50 nm are treated prior to coating with an oxygen plasma, followed by an argon plasma. These plasma-treated glass plaques form the substrates to which the OLEDs are applied.

The OLEDs basically have the following layer structure: substrate/hole injection layer (HIL)/hole transport layer (HTL)/electron blocker layer (EBL)/emission layer (EML)/optional hole blocker layer (HBL)/electron transport layer (ETL)/optional electron injection layer (EIL) and finally a cathode. The cathode is formed by an aluminium layer of thickness 100 nm. The exact structure of the OLEDs can be found in Table 1. The materials required for production of the OLEDs are shown in Table 2.

All materials are applied by thermal vapour deposition in a vacuum chamber. In this case, the emission layer always consists of at least one matrix material (host material) and an emitting dopant (emitter) which is added to the matrix material(s) in a particular proportion by volume by co-evaporation. Details given in such a form as EG3:IC1:TEG1 (59%:29%:12%) mean here that the material EG3 is present in the layer in a proportion by volume of 59%, IC1 in a proportion of 29% and TEG1 in a proportion of 12%. Analogously, the electron transport layer may also consist of a mixture of two materials.

The OLEDs are characterized in a standard manner. For this purpose, the electroluminescence spectra, the current efficiency (measured in cd/A) and the external quantum efficiency (EQE, measured in percent) are determined as a function of luminance, calculated from current-voltage-luminance characteristics (IUL characteristics) assuming Lambertian emission characteristics. The voltage, current efficiency and external quantum efficiency are reported for a luminance of 1000 cd/m$^2$. The electroluminescence spectra are determined at a luminance of 1000 cd/m$^2$, and the CIE 1931 x and y colour coordinates are calculated therefrom.

The lifetime LT_L1 is defined as the time after which the luminance drops from the starting luminance to a certain proportion L1 in the course of operation with constant current. LD_80 is thus the time within which the luminance drops to 80% of its starting value in operation. In the examples listed below, a current density of 40 mA/cm$^2$ is used as an operating condition.

Use of Materials of the Invention in OLEDs

The inventive compounds EG1 to EG12 are used in Examples I1 to I12 as matrix material in the emission layer. The colour coordinates of the electroluminescence spectra of the OLEDs from these experiments are CIEx=0.3 and CIEy=0.6. The materials are thus suitable for use in the emission layer of phosphorescent green OLEDs.

With the OLED of the invention in Example I1, the following device data are obtained:
Voltage: 3.2 V
Current efficiency: 62 cd/A
EQE: 17%
LD_80: 160 h Comparable device data are obtained with the OLEDs of the invention in examples I2 to I12.

TABLE 1

Structure of the OLEDs

| Ex. | HIL thickness | HTL thickness | EBL thickness | EML thickness | HBL | ETL thickness |
|---|---|---|---|---|---|---|
| I1 | HATCN 5 nm | SpMA1 230 nm | SpMA3 20 nm | EG3:IC1:TEG1 (59%:29%:12%) 30 nm | — | ETM1:LiQ (50%:50%) 40 nm |
| I2 | HATCN 5 nm | SpMA1 230 nm | SpMA3 20 nm | EG1:TEG1 (95%:5%) 30 nm | — | ETM1:LiQ (50%:50%) 40 nm |
| I3 | HATCN 5 nm | SpMA1 230 nm | SpMA3 20 nm | EG2:TEG1 (95%:5%) 30 nm | — | ETM1:LiQ (50%:50%) 40 nm |
| I4 | HATCN 5 nm | SpMA1 230 nm | SpMA3 20 nm | EG3:TEG1 (95%:5%) 30 nm | — | ETM1:LiQ (50%:50%) 40 nm |
| I5 | HATCN 5 nm | SpMA1 230 nm | SpMA3 20 nm | EG4:TEG1 (95%:5%) 30 nm | — | ETM1:LiQ (50%:50%) 40 nm |
| I6 | HATCN 5 nm | SpMA1 230 nm | SpMA3 20 nm | EG5:TEG1 (95%:5%) 30 nm | — | ETM1:LiQ (50%:50%) 40 nm |
| I7 | HATCN 5 nm | SpMA1 230 nm | SpMA3 20 nm | EG6:TEG1 (95%:5%) 30 nm | — | ETM1:LiQ (50%:50%) 40 nm |
| I8 | HATCN 5 nm | SpMA1 230 nm | SpMA3 20 nm | EG7:TEG1 (95%:5%) 30 nm | — | ETM1:LiQ (50%:50%) 40 nm |
| I9 | HATCN 5 nm | SpMA1 230 nm | SpMA3 20 nm | EG8:TEG1 (95%:5%) 30 nm | — | ETM1:LiQ (50%:50%) 40 nm |
| I10 | HATCN 5 nm | SpMA1 230 nm | SpMA3 20 nm | EG9:TEG1 (95%:5%) 30 nm | — | ETM1:LiQ (50%:50%) 40 nm |
| I11 | HATCN 5 nm | SpMA1 230 nm | SpMA3 20 nm | EG10:TEG1 (95%:5%) 30 nm | — | ETM1:LiQ (50%:50%) 40 nm |

TABLE 1-continued
| | | | Structure of the OLEDs | | | |
|---|---|---|---|---|---|---|
| Ex. | HIL thickness | HTL thickness | EBL thickness | EML thickness | HBL | ETL thickness |
| I12 | HATCN 5 nm | SpMA1 230 nm | SpMA3 20 nm | EG11:TEG1 (95%:5%) 30 nm | — | ETM1:LiQ (50%:50%) 40 nm |
TABLE 2
Structural formulae of the materials for the OLEDs
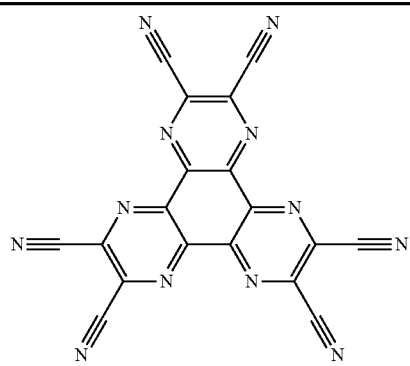
HATCN
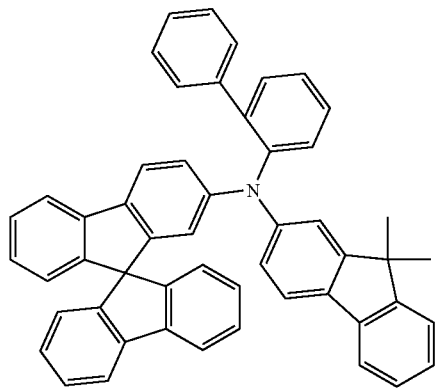
SpMA1
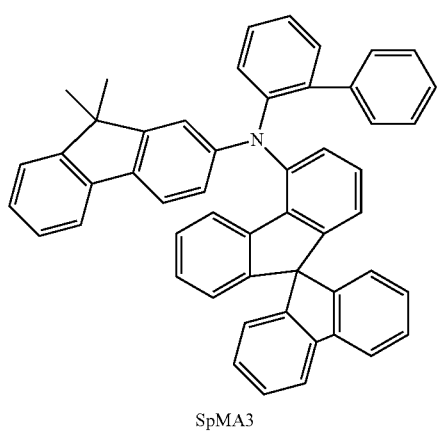 [SMILES: CC1(C)c2ccccc2-c2ccc(N(c3ccccc3-c3ccccc3)c3cccc4c3-c3ccccc3C43c4ccccc4-c4ccccc43)cc21]
SpMA3

TABLE 2-continued
Structural formulae of the materials for the OLEDs
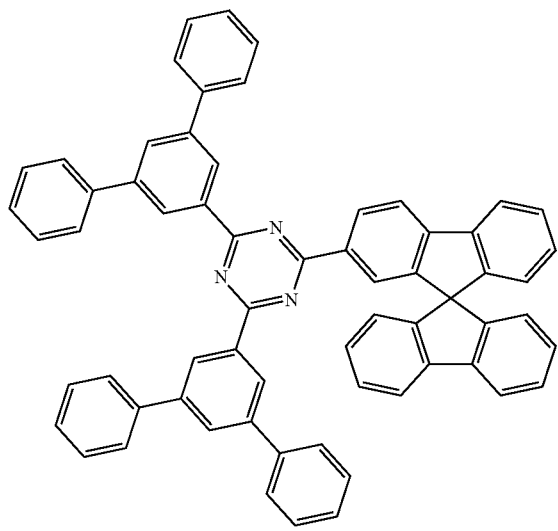
ETM1
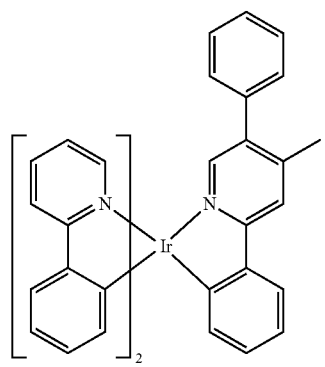
TEG1
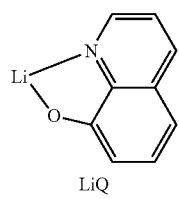
LiQ
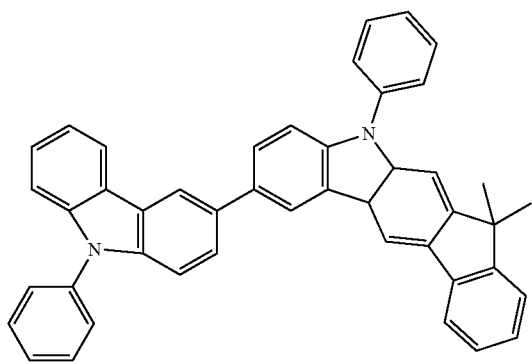
IC1

TABLE 2-continued
Structural formulae of the materials for the OLEDs
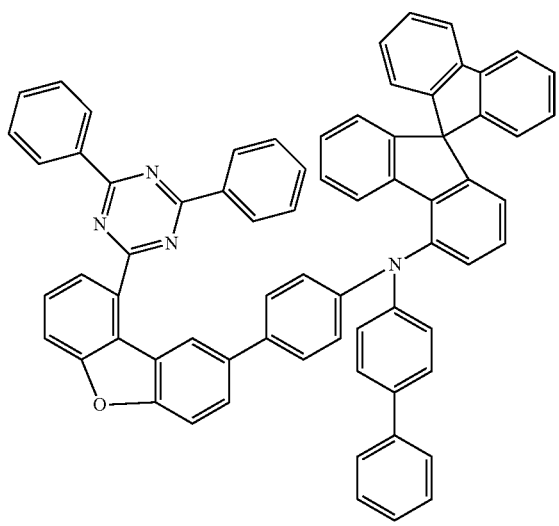
EG1
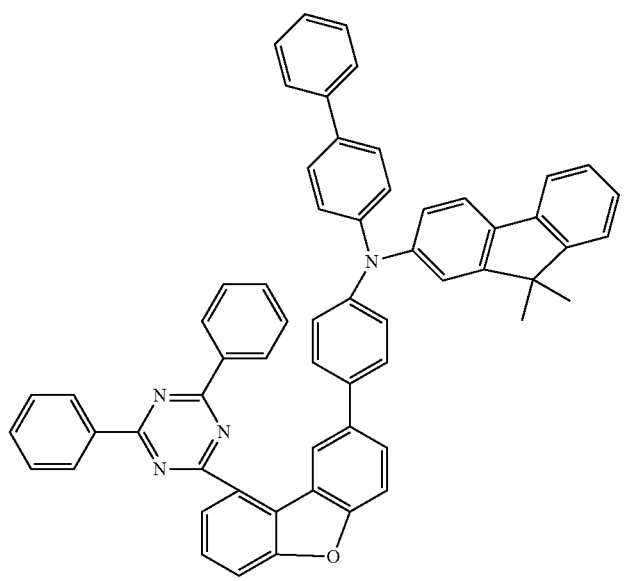
EG2

TABLE 2-continued
Structural formulae of the materials for the OLEDs
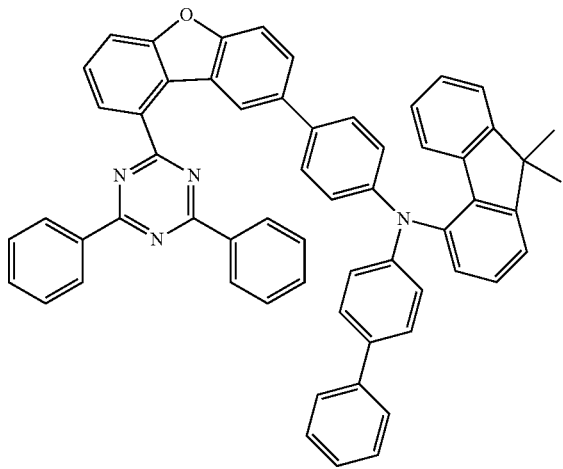
EG3
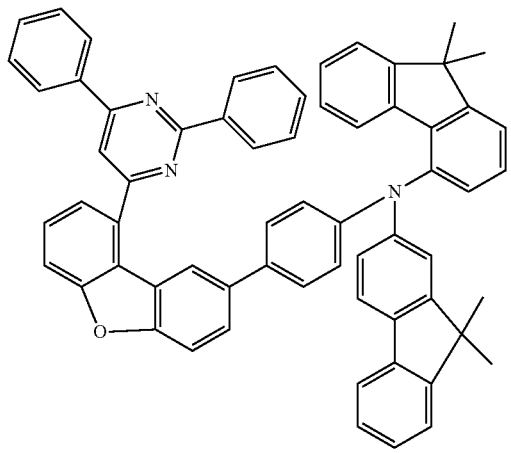
EG4

TABLE 2-continued
Structural formulae of the materials for the OLEDs
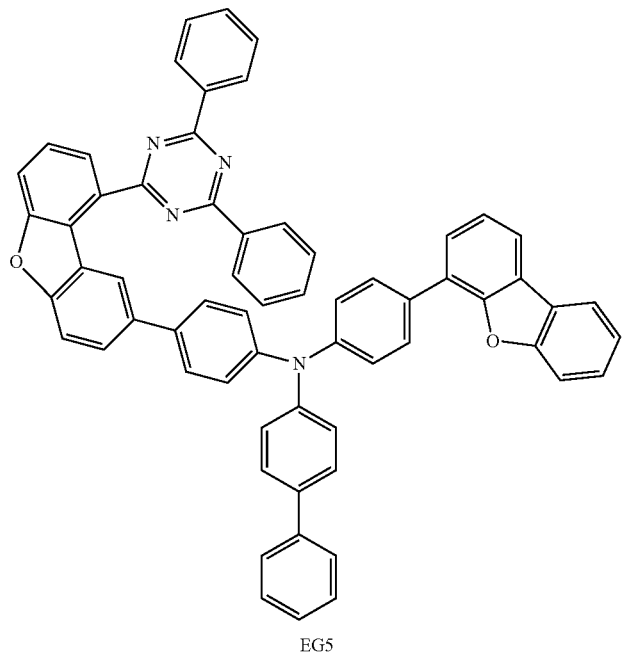 [SMILES: c1ccc(-c2ccc(N(c3ccc(-c4ccc5oc6cccc(-c7nc(-c8ccccc8)nc(-c8ccccc8)n7)c6c5c4)cc3)c3ccc(-c4cccc5c4oc4ccccc45)cc3)cc2)cc1]
EG5
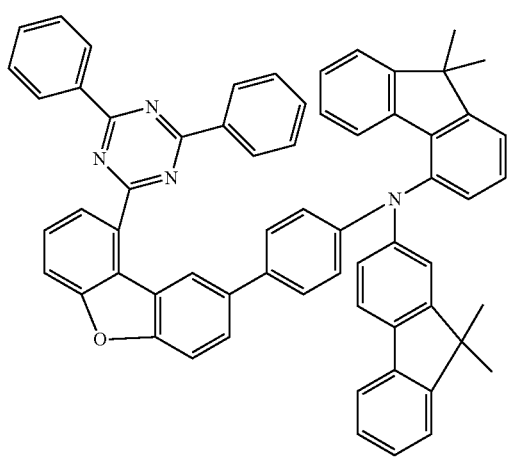
EG6

TABLE 2-continued
Structural formulae of the materials for the OLEDs
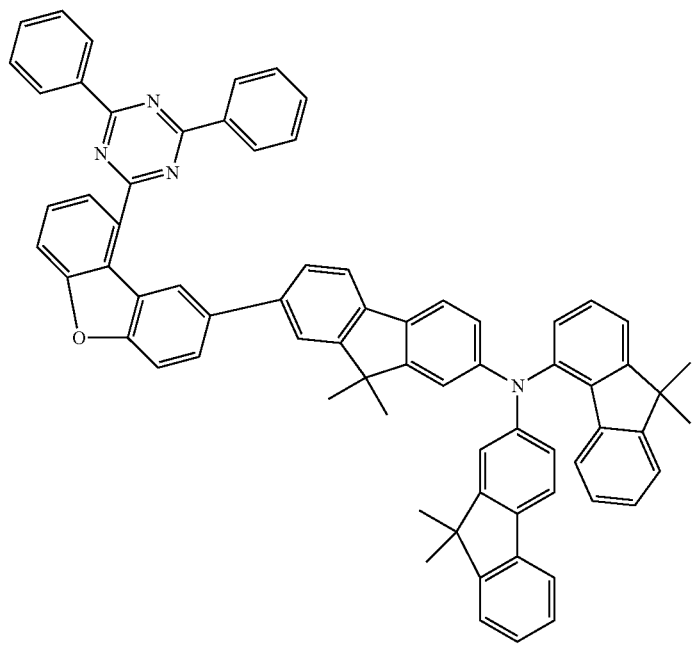
EG7
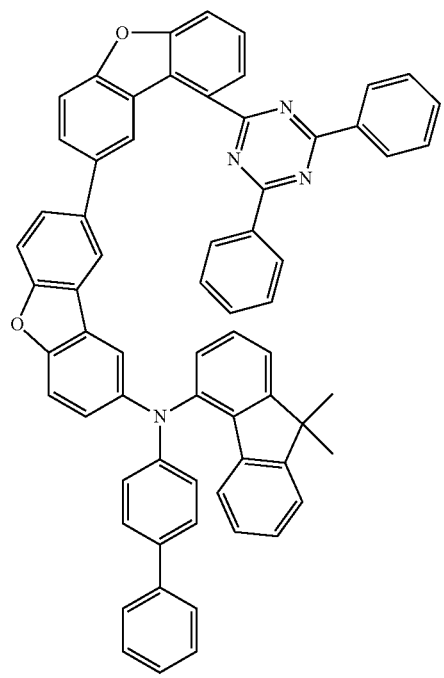
EG8

TABLE 2-continued
Structural formulae of the materials for the OLEDs
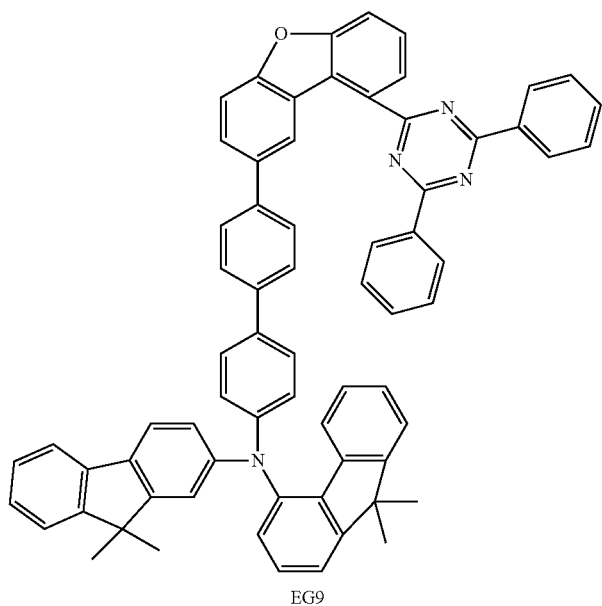 [SMILES: CC1(C)c2ccccc2-c2ccc(N(c3ccc(-c4ccc(-c5ccc6oc7cccc(-c8nc(-c9ccccc9)nc(-c9ccccc9)n8)c7c6c5)cc4)cc3)c3cccc4c3-c3ccccc3C4(C)C)cc21]
EG9
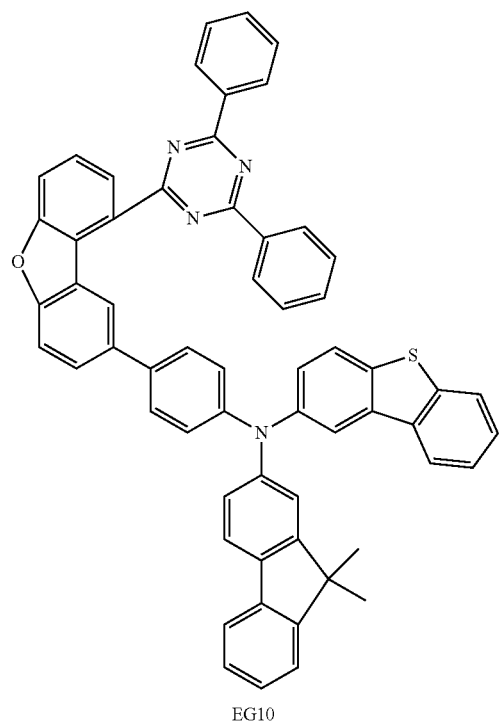 [SMILES: CC1(C)c2ccccc2-c2ccc(N(c3ccc(-c4ccc5oc6cccc(-c7nc(-c8ccccc8)nc(-c8ccccc8)n7)c6c5c4)cc3)c3ccc4sc5ccccc5c4c3)cc21]
EG10

TABLE 2-continued

Structural formulae of the materials for the OLEDs

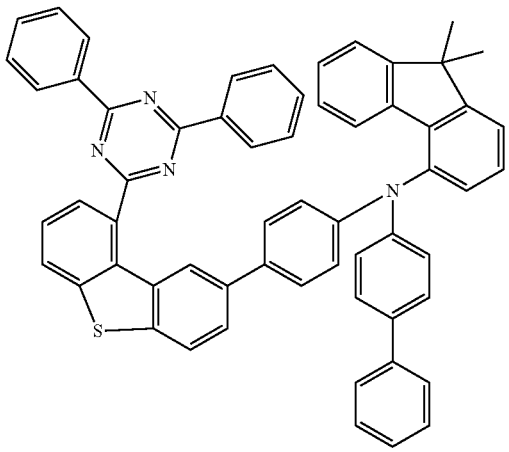

EG11

The invention claimed is:
1. A compound of formula (1d)

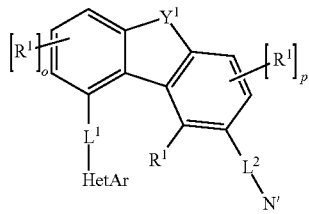

Formula (1d)

where the symbols used are as follows:
$Y^1$ is O, S, or NR, where the R radical bonded to N is not H or D;
$L^1$ is a single bond;
$L^2$ is a single bond;
o is 0, 1, 2 or 3;
p is 0, 1 or 2;
N' is a group of the formula (L-1)

Formula (L-1)

where the dotted bond represents the linkage to $L^2$;
$Y^2$ is the same or different at each instance and is selected from a single bond, $C(R)_2$, O, S, NR, where the R radical bonded to N is not H or D;
n is the same or different at each instance and is 0 or 1, where, when at least one $Y^2$ is a single bond, at least two n are 1;
Ar is the same or different at each instance and is an aromatic ring system which has 6 to 18 aromatic ring atoms and may be substituted by one or more $R^3$ radicals, or a dibenzofuranyl or dibenzothienyl group, each of which may be substituted by one or more $R^3$ radicals;

HetAr is a group of one of the formulae (2-1), to (4-1)

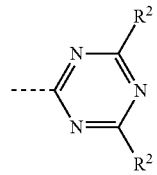

Formula (2-1)

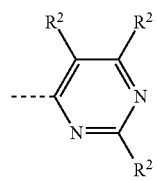

Formula (2-2)

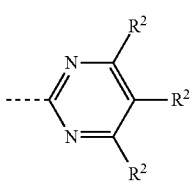

Formula (2-3)

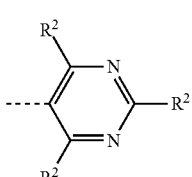

Formula (2-4)

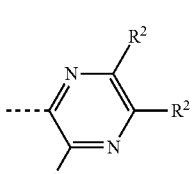

Formula (2-5)

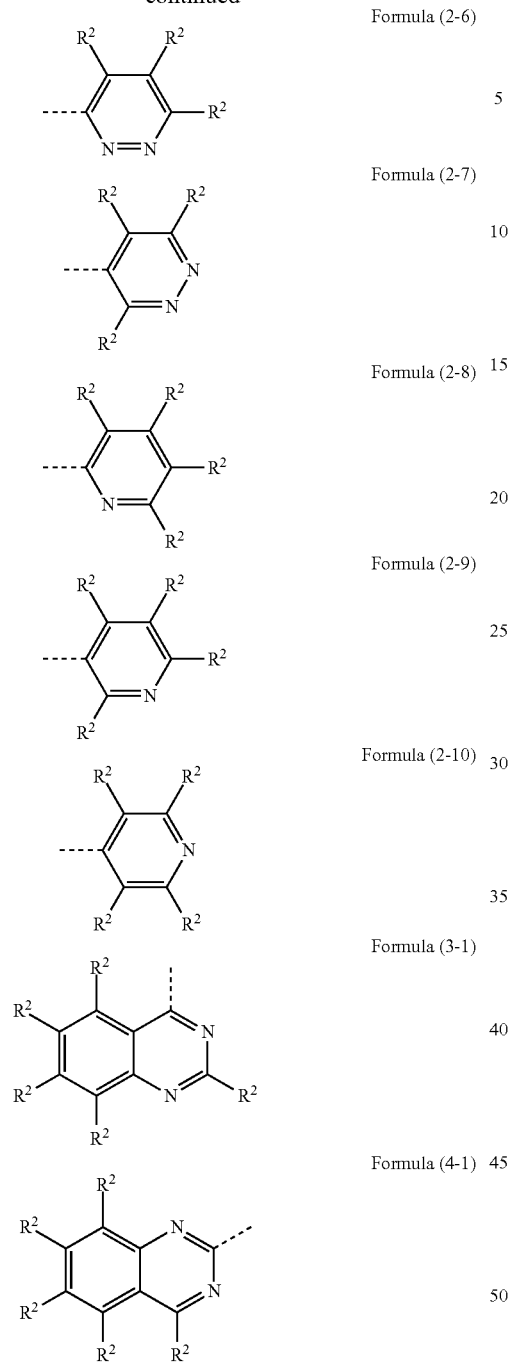

where the dotted bond represents the linkage of this group;

X is the same or different at each instance and is $CR^2$ or N, with the proviso that at least one X symbol is N;

R, $R^1$, $R^2$, $R^3$ is the same or different at each instance and is selected from the group consisting of H, D, F, CN, $N(Ar^1)_2$, $N(R^4)_2$, a straight-chain alkyl or alkoxy group having 1 to 10 carbon atoms or a branched or cyclic alkyl or alkoxy group having 3 to 10 carbon atoms, each of which may be substituted by one or more $R^4$ radicals, where one or more nonadjacent $CH_2$ groups may be replaced by O, and where one or more hydrogen atoms may be replaced by D or F, an aromatic or heteroaromatic ring system which has 5 to 24 aromatic ring atoms and may be substituted in each case by one or more $R^4$ radicals, and an aralkyl or heteroaralkyl group which has 5 to 25 aromatic ring atoms and may be substituted by one or more $R^4$ radicals; at the same time, it is optionally possible for two adjacent R substituents, or two adjacent $R^1$ substituents, or two adjacent $R^2$ substituents, or two adjacent $R^3$ substituents to form an aliphatic, heteroaliphatic, aromatic or heteroaromatic ring system which may be substituted by one or more $R^4$ radicals;

where $R^1$, if $Y^1$ is O or S and if connected to the 9-position of the resultant dibenzofuran or dibenzothiophene, or if $Y^1$ is NR and if connected to the 5-position of the resultant carbazole, is H;

$Ar^1$ is the same or different at each instance and is an aromatic or heteroaromatic ring system which has 5 to 30 aromatic ring atoms and may be substituted by one or more nonaromatic $R^4$ radicals; at the same time, two $Ar^1$ radicals bonded to the same nitrogen atom, phosphorus atom or boron atom may also be bridged to one another by a single bond or a bridge selected from $N(R^4)$, $C(R^4)_2$, O and S;

$R^4$ is the same or different at each instance and is selected from the group consisting of H, D, F, CN, $N(R^5)_2$, a straight-chain alkyl, or alkoxy group having 1 to 10 carbon atoms or a branched or cyclic alkyl, or alkoxy group having 3 to 10 carbon atoms, each of which may be substituted by one or more $R^5$ radicals, where one or more nonadjacent $CH_2$ groups may be replaced O, and where one or more hydrogen atoms may be replaced by D or F, an aromatic or heteroaromatic ring system which has 5 to 24 aromatic ring atoms and may be substituted in each case by one or more $R^5$ radicals, at the same time, it is optionally possible for two adjacent $R^4$ substituents to form an aliphatic or aromatic or heteroaromatic ring system which may be substituted by one or more $R^5$ radicals;

$R^5$ is the same or different at each instance and is selected from the group consisting of H, D, F, CN, an aliphatic hydrocarbyl radical having 1 to 10 carbon atoms, and an aromatic or heteroaromatic ring system having 5 to 13 aromatic ring atoms in which one or more hydrogen atoms may be replaced by D or F, and which may be substituted by one or more alkyl groups each having 1 to 4 carbon atoms; at the same time, it is possible for two or more adjacent $R^5$ substituents together to form an aliphatic ring system;

excluding the following compounds:

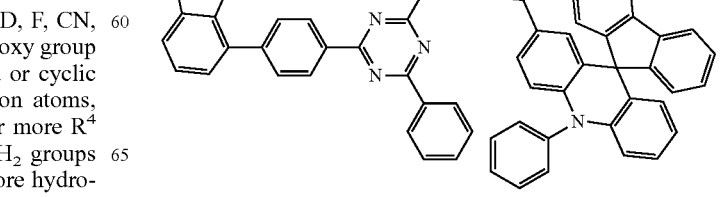

2. The compound according to claim 1, wherein the N' group is a group of the formulae (L-2) to (L-7)

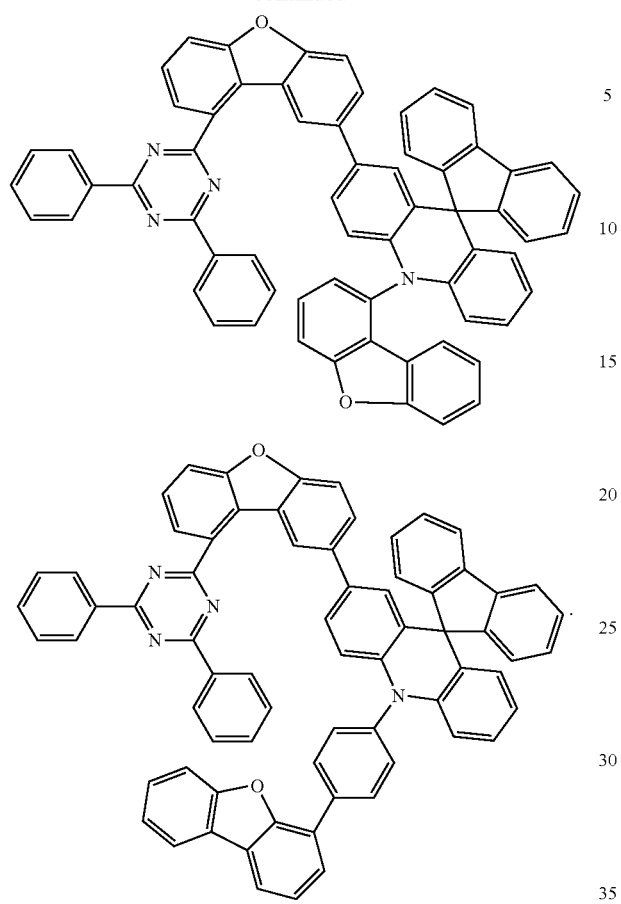

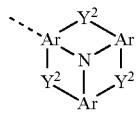 Formula (L-2)

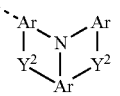 Formula (L-3)

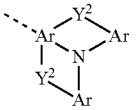 Formula (L-4)

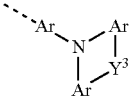 Formula (L-5)

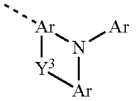 Formula (L-6)

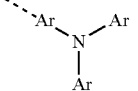 Formula (L-7)

where the symbols that occur have the definitions given in claim 1 and in addition:

$Y^3$ is the same or different at each instance and is selected from $C(R)_2$, O, S, NR, where the R radical bonded to N is not H or D.

3. The compound according to claim 2, wherein the N' group is a group of the formula (L-7).

4. The compound according to claim 2, wherein $Y^3$ is the same or different at each instance and is selected from O, S, NR, where the R radical bonded to N is not H or D.

5. The compound according to claim 1, wherein $Y^1$ is O or S.

6. A formulation comprising at least one compound according to claim 1 and at least one solvent.

7. An electronic device comprising at least one compound according to claim 1.

8. An organic electroluminescent device, wherein the compound according to claim 1 is used as matrix material for fluorescent or phosphorescent emitters and/or in an electron transport layer and/or in an electron-blocking or exciton-blocking layer and/or in a hole transport layer.

* * * * *